US008057788B2

(12) United States Patent
Hariri

(10) Patent No.: US 8,057,788 B2
(45) Date of Patent: *Nov. 15, 2011

(54) PLACENTAL STEM CELL POPULATIONS

(75) Inventor: Robert J. Hariri, Bernardsville, NJ (US)

(73) Assignee: Anthrogenesis Corporation, Warren, NJ (US)

( * ) Notice: Subject to any disclaimer, the term of this patent is extended or adjusted under 35 U.S.C. 154(b) by 164 days.

This patent is subject to a terminal disclaimer.

(21) Appl. No.: 11/648,813

(22) Filed: Dec. 28, 2006

(65) Prior Publication Data

US 2007/0275362 A1    Nov. 29, 2007

Related U.S. Application Data

(60) Continuation-in-part of application No. 10/640,428, filed on Aug. 12, 2003, now Pat. No. 7,255,879, which is a division of application No. 10/076,180, filed on Feb. 13, 2002, now abandoned, which is a continuation-in-part of application No. 10/004,942, filed on Dec. 5, 2001, now Pat. No. 7,045,148, application No. 11/648,813, which is a continuation-in-part of application No. 10/074,976, filed on Feb. 13, 2002, now Pat. No. 7,311,904, and a continuation-in-part of application No. 10/366,671, filed on Feb. 13, 2003, now Pat. No. 7,311,905.

(60) Provisional application No. 60/268,560, filed on Feb. 14, 2001, provisional application No. 60/251,900, filed on Dec. 6, 2000, provisional application No. 60/268,560, filed on Feb. 14, 2001, provisional application No. 60/754,968, filed on Dec. 29, 2005, provisional application No. 60/846,641, filed on Sep. 22, 2006.

(51) Int. Cl.
*A01N 63/00* (2006.01)
*C12N 5/00* (2006.01)
(52) U.S. Cl. ....................... 424/93.1; 435/325
(58) Field of Classification Search ........................ None
See application file for complete search history.

(56) References Cited

U.S. PATENT DOCUMENTS

| | | |
|---|---|---|
| 3,862,002 A | 1/1975 | Sanders |
| 4,829,000 A | 5/1989 | Kleinman et al. |
| 5,004,681 A | 4/1991 | Boyse et al. |
| 5,192,553 A | 3/1993 | Boyse et al. |
| 5,197,985 A | 3/1993 | Caplan et al. |
| 5,226,914 A | 7/1993 | Caplan et al. |
| 5,272,071 A | 12/1993 | Chappel |
| 5,284,766 A | 2/1994 | Okano et al. |
| 5,356,373 A | 10/1994 | Dracker et al. |
| 5,372,581 A | 12/1994 | Anderson |
| 5,415,665 A | 5/1995 | Hessel et al. |
| 5,437,994 A | 8/1995 | Emerson et al. |
| 5,443,950 A | 8/1995 | Naughton et al. |
| 5,460,964 A | 10/1995 | McGlave et al. |
| 5,464,764 A | 11/1995 | Capecchi et al. |
| 5,486,359 A | 1/1996 | Caplan et al. |
| 5,487,992 A | 1/1996 | Capecchi et al. |
| 5,516,532 A | 5/1996 | Atala et al. |
| 5,591,625 A | 1/1997 | Gerson et al. |
| 5,605,822 A | 2/1997 | Emerson et al. |
| 5,627,059 A | 5/1997 | Capecchi et al. |
| 5,635,386 A | 6/1997 | Palsson et al. |
| 5,635,387 A | 6/1997 | Fei et al. |
| 5,643,741 A | 7/1997 | Tsukamoto et al. |
| 5,646,043 A | 7/1997 | Emerson et al. |
| 5,654,186 A | 8/1997 | Cerami et al. |
| 5,654,381 A | 8/1997 | Hrkach et al. |
| 5,665,557 A | 9/1997 | Murray et al. |
| 5,668,104 A | 9/1997 | Nakahata et al. |
| 5,670,147 A | 9/1997 | Emerson et al. |
| 5,670,351 A | 9/1997 | Emerson et al. |
| 5,672,346 A | 9/1997 | Srour et al. |
| 5,677,139 A | 10/1997 | Johnson |
| 5,709,854 A | 1/1998 | Griffith-Cima et al. |
| 5,716,616 A | 2/1998 | Prockop et al. |
| 5,716,794 A | 2/1998 | Tjota et al. |
| 5,716,827 A | 2/1998 | Tsukamoto |
| 5,733,541 A | 3/1998 | Taichman et al. |
| 5,733,542 A | 3/1998 | Haynesworth et al. |
| 5,736,396 A | 4/1998 | Bruder et al. |
| 5,744,361 A | 4/1998 | Hoffman et al. |
| 5,750,397 A | 5/1998 | Tsukamoto et al. |
| 5,763,197 A | 6/1998 | Tsukamoto et al. |
| 5,763,266 A | 6/1998 | Palsson et al. |
| 5,807,686 A | 9/1998 | Wagner et al. |
| 5,811,094 A | 9/1998 | Caplan et al. |
| 5,827,735 A | 10/1998 | Young et al. |
| 5,827,740 A | 10/1998 | Pittenger |
| 5,827,742 A | 10/1998 | Scadden |

(Continued)

FOREIGN PATENT DOCUMENTS

CN     1407088     4/2003

(Continued)

OTHER PUBLICATIONS

Huss, Stem Cells 2000;18:1-9.*
Moreau et al. Blood 1993;82:2396-2405.*
Barry et al. Biochem Biophys Res Com 1999;265:134-9.*
Sherley, Stem Cell 2002;20:561-72.*
Pittenger et al. Science 1999;284:143-7.*
Weiss et al. Stem Cells 2006;24:781-792.*
Weissman et al. Annu Rev Cell Dev Biol 2001;17:387-403.*
Barlow et al. Stem Cells Dev 2008;17:1095-1108.*
Pittenger, et al., "Multilineage Potential of Adult Human Mesenchymal Stem Cells." Science, American Association of Science, vol. 284, No. 5411, Apr. 2, 1999, pp. 143-147.

(Continued)

Primary Examiner — Q. Janice Li
(74) Attorney, Agent, or Firm — Jones Day

(57) ABSTRACT

The present invention provides placental stem cells and placental stem cell populations, and methods of culturing, proliferating and expanding the same. The invention also provides methods of differentiating the placental stem cells. The invention further provides methods of using the placental stem cells in assays and for transplanting.

24 Claims, 13 Drawing Sheets

U.S. PATENT DOCUMENTS

Figure 1:
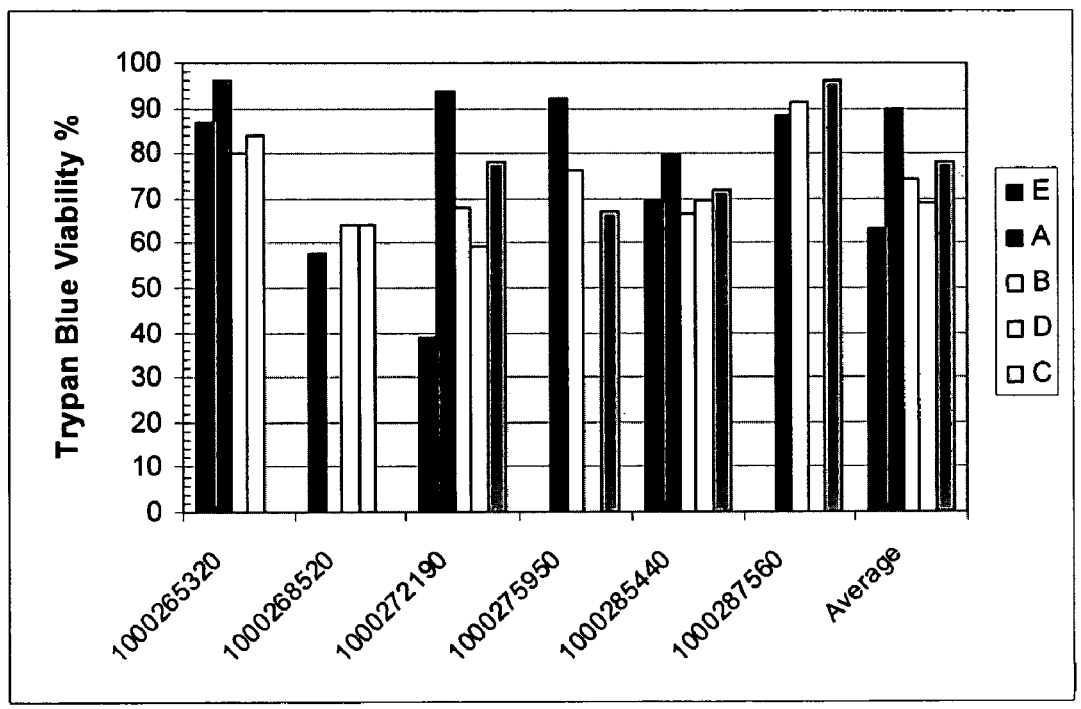

| | | | |
|---|---|---|---|
| 5,837,539 A | 11/1998 | Caplan et al. |
| 5,849,553 A | 12/1998 | Anderson et al. |
| 5,851,984 A | 12/1998 | Matthews et al. |
| 5,855,619 A | 1/1999 | Caplan et al. |
| 5,858,782 A | 1/1999 | Long et al. |
| 5,866,414 A | 2/1999 | Badylak et al. |
| 5,874,301 A | 2/1999 | Keller et al. |
| 5,877,299 A | 3/1999 | Thomas et al. |
| 5,879,318 A | 3/1999 | Van Der Heiden et al. |
| 5,879,940 A | 3/1999 | Torok-Storb et al. |
| 5,902,741 A | 5/1999 | Purchio et al. |
| 5,905,041 A | 5/1999 | Beug et al. |
| 5,906,934 A | 5/1999 | Grande et al. |
| 5,908,782 A | 6/1999 | Marshak et al. |
| 5,908,784 A | 6/1999 | Johnstone et al. |
| 5,914,108 A | 6/1999 | Tsukamoto et al. |
| 5,914,268 A | 6/1999 | Keller et al. |
| 5,916,202 A | 6/1999 | Haswell |
| 5,919,176 A | 7/1999 | Kuypers et al. |
| 5,919,702 A | 7/1999 | Purchio et al. |
| 5,922,597 A | 7/1999 | Verfaillie et al. |
| 5,925,567 A | 7/1999 | Kraus et al. |
| 5,928,214 A | 7/1999 | Rubinstein et al. |
| 5,928,947 A | 7/1999 | Anderson et al. |
| 5,942,225 A | 8/1999 | Bruder et al. |
| 5,942,496 A | 8/1999 | Bonadio et al. |
| 5,958,767 A | 9/1999 | Snyder et al. |
| 5,962,325 A | 10/1999 | Naughton et al. |
| 5,968,829 A | 10/1999 | Carpenter |
| 5,969,105 A | 10/1999 | Feng et al. |
| 5,993,429 A | 11/1999 | Kuypers et al. |
| 5,997,860 A | 12/1999 | Brauer et al. |
| 6,001,654 A | 12/1999 | Anderson et al. |
| 6,010,696 A | 1/2000 | Caplan et al. |
| 6,011,000 A | 1/2000 | Perrine et al. |
| 6,020,469 A | 2/2000 | Hershenson |
| 6,022,540 A | 2/2000 | Bruder et al. |
| 6,022,743 A | 2/2000 | Naughton et al. |
| 6,022,848 A | 2/2000 | Kozlov et al. |
| 6,030,836 A | 2/2000 | Thiede |
| 6,057,123 A | 5/2000 | Craig et al. |
| 6,059,968 A | 5/2000 | Wolf, Jr. |
| 6,077,708 A | 6/2000 | Collins et al. |
| 6,087,113 A | 7/2000 | Caplan et al. |
| 6,093,531 A | 7/2000 | Bjornson et al. |
| 6,110,739 A | 8/2000 | Keller et al. |
| 6,127,135 A | 10/2000 | Hill et al. |
| 6,146,888 A | 11/2000 | Smith et al. |
| 6,174,333 B1 | 1/2001 | Kadiyala et al. |
| 6,179,819 B1 | 1/2001 | Haswel |
| 6,184,035 B1 | 2/2001 | Csete et al. |
| 6,190,368 B1 | 2/2001 | Kuypers et al. |
| 6,214,369 B1 | 4/2001 | Grande et al. |
| 6,224,860 B1 | 5/2001 | Brown |
| 6,225,119 B1 | 5/2001 | Qasba et al. |
| 6,227,202 B1 | 5/2001 | Mataparkar |
| 6,231,880 B1 | 5/2001 | Perrine |
| 6,239,157 B1 | 5/2001 | Mbalaviele et al. |
| 6,248,587 B1 | 6/2001 | Rodgers et al. |
| 6,251,383 B1 | 6/2001 | Upadhyay et al. |
| 6,255,112 B1 | 7/2001 | Thiede et al. |
| 6,261,549 B1 | 7/2001 | Fernandez et al. |
| 6,280,718 B1 | 8/2001 | Kaufman et al. |
| 6,281,012 B1 | 8/2001 | McIntosh et al. |
| 6,300,314 B1 | 10/2001 | Wallnet et al. |
| 6,306,575 B1 | 10/2001 | Thomas et al. |
| 6,312,950 B1 | 11/2001 | Ohmura et al. |
| 6,322,784 B1 | 11/2001 | Pittenger et al. |
| 6,326,019 B1 | 12/2001 | Tseng |
| 6,326,198 B1 | 12/2001 | Emerson et al. |
| 6,328,765 B1 | 12/2001 | Hardwick et al. |
| 6,328,960 B1 | 12/2001 | McIntosh et al. |
| 6,333,029 B1 | 12/2001 | Vyakamam et al. |
| 6,335,195 B1 | 1/2002 | Rodgers et al. |
| 6,337,387 B1 | 1/2002 | Sakano et al. |
| 6,338,942 B2 | 1/2002 | Kraus et al. |
| 6,355,239 B1 | 3/2002 | Bruder et al. |
| 6,368,636 B1 | 4/2002 | McIntosh et al. |
| 6,379,953 B1 | 4/2002 | Bruder et al. |
| 6,387,367 B1 | 5/2002 | Davis-Sproul et al. |
| 6,387,369 B1 | 5/2002 | Pittenger et al. |
| 6,461,645 B1 | 10/2002 | Boyse et al. |
| 6,497,875 B1 | 12/2002 | Sorrell et al. |
| 6,534,084 B1 | 3/2003 | Vyakamam et al. |
| 6,541,024 B1 | 4/2003 | Kadiyala et al. |
| 6,548,299 B1 | 4/2003 | Pykett |
| 6,685,936 B2 | 2/2004 | McIntosh et al. |
| 6,709,864 B1 | 3/2004 | Pittenger et al. |
| 6,797,269 B2 | 9/2004 | Mosca et al. |
| 6,835,377 B2 | 12/2004 | Goldberg et al. |
| 6,863,900 B2 | 3/2005 | Kadiyala et al. |
| 6,875,430 B2 | 4/2005 | McIntosh et al. |
| 6,875,607 B1 | 4/2005 | Reubinoff et al. |
| 7,029,666 B2 | 4/2006 | Bruder et al. |
| 7,045,148 B2 | 5/2006 | Hariri |
| 7,091,353 B2 | 8/2006 | Robarge et al. |
| 7,147,626 B2 | 12/2006 | Goodman et al. |
| 7,244,759 B2 | 7/2007 | Muller et al. |
| 7,255,879 B2 | 8/2007 | Hariri |
| 7,311,904 B2 | 12/2007 | Hariri |
| 7,311,905 B2 | 12/2007 | Hariri |
| 7,468,276 B2 * | 12/2008 | Hariri .......................... 435/325 |
| 7,498,171 B2 | 3/2009 | Hariri et al. |
| 7,638,141 B2 | 12/2009 | Hariri |
| 7,642,091 B2 | 1/2010 | Lee et al. |
| 7,682,803 B2 | 3/2010 | Paludan et al. |
| 7,700,090 B2 | 4/2010 | Heidaran et al. |
| 2001/0005591 A1 | 6/2001 | Qasba et al. |
| 2001/0038836 A1 | 11/2001 | During et al. |
| 2002/0102239 A1 | 8/2002 | Koopmans |
| 2002/0123141 A1 | 9/2002 | Hariri |
| 2002/0132343 A1 | 9/2002 | Lum |
| 2002/0160510 A1 | 10/2002 | Hariri |
| 2003/0007954 A1 | 1/2003 | Naughton et al. |
| 2003/0032179 A1 | 2/2003 | Hariri |
| 2003/0044977 A1 | 3/2003 | Sakuragawa et al. |
| 2003/0045552 A1 | 3/2003 | Robarge et al. |
| 2003/0096841 A1 | 5/2003 | Robarge et al. |
| 2003/0161818 A1 | 8/2003 | Weiss et al. |
| 2003/0180269 A1 | 9/2003 | Hariri |
| 2003/0235563 A1 | 12/2003 | Strom et al. |
| 2003/0235909 A1 | 12/2003 | Hariri |
| 2004/0018617 A1 | 1/2004 | Hwang |
| 2004/0028660 A1 | 2/2004 | Hariri |
| 2004/0048372 A1 | 3/2004 | Hariri |
| 2004/0048796 A1 | 3/2004 | Hariri et al. |
| 2004/0107453 A1 | 6/2004 | Furcht et al. |
| 2004/0136967 A1 | 7/2004 | Weiss et al. |
| 2004/0161419 A1 | 8/2004 | Strom et al. |
| 2004/0171147 A1 | 9/2004 | Hariri |
| 2004/0180040 A1 | 9/2004 | Phillips et al. |
| 2004/0219136 A1 | 11/2004 | Hariri |
| 2004/0229351 A1 | 11/2004 | Rodriguez et al. |
| 2004/0241144 A1 | 12/2004 | Kaps et al. |
| 2005/0019865 A1 | 1/2005 | Kihm et al. |
| 2005/0019908 A1 | 1/2005 | Hariri |
| 2005/0032209 A1 | 2/2005 | Messina et al. |
| 2005/0037491 A1 | 2/2005 | Mistry et al. |
| 2005/0042595 A1 | 2/2005 | Haas |
| 2005/0054093 A1 | 3/2005 | Haas |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0074435 A1 | 4/2005 | Casper |
| 2005/0085543 A1 | 4/2005 | Wallimann et al. |
| 2005/0089513 A1 | 4/2005 | Sakuragawa et al. |
| 2005/0112104 A1 | 5/2005 | Pittenger et al. |
| 2005/0118712 A1 | 6/2005 | Tsai et al. |
| 2005/0118715 A1 | 6/2005 | Hariri |
| 2005/0124003 A1 | 6/2005 | Atala et al. |
| 2005/0143420 A1 | 6/2005 | Moutouh-de Parseval et al. |
| 2005/0148034 A1 | 7/2005 | Hariri |
| 2005/0148074 A1 | 7/2005 | Davies et al. |
| 2005/0176139 A1 | 8/2005 | Chen et al. |
| 2005/0181502 A1 | 8/2005 | Furcht et al. |
| 2005/0186182 A1 | 8/2005 | Deisher et al. |

| | | | | | | |
|---|---|---|---|---|---|---|
| 2005/0233452 | A1 | 10/2005 | Ho et al. | 2010/0047214 A1 | 2/2010 | Abramson et al. |
| 2005/0239897 | A1 | 10/2005 | Pittenger et al. | 2010/0047351 A1 | 2/2010 | Zeitlin et al. |
| 2005/0266391 | A1 | 12/2005 | Bennett et al. | 2010/0120015 A1 | 5/2010 | Hariri |
| 2005/0272148 | A1 | 12/2005 | Hariri | 2010/0124569 A1 | 5/2010 | Abbot |
| 2005/0276792 | A1 | 12/2005 | Kaminski et al. | 2010/0143312 A1 | 6/2010 | Hariri |
| 2005/0282272 | A1 | 12/2005 | Bhatia et al. | 2010/0183571 A1 | 7/2010 | Paludan et al. |
| 2005/0283844 | A1 | 12/2005 | Furcht et al. | | | |
| 2006/0008450 | A1 | 1/2006 | Verfaillie et al. | | | |

FOREIGN PATENT DOCUMENTS

| | | |
|---|---|---|
| CN | 1548529 | 5/2003 |
| CN | 1786154 | 6/2006 |
| EP | 0333328 | 9/1989 |
| EP | 0529751 | 3/1993 |
| EP | 0552380 | 7/1993 |
| EP | 1264877 | 12/2002 |
| EP | 1288293 A1 | 3/2003 |
| EP | 1384775 A1 | 1/2004 |
| EP | 1405649 | 4/2004 |
| EP | 1535994 A1 | 6/2005 |
| EP | 1775341 | 4/2007 |
| JP | 2003235549 | 12/2002 |
| JP | 2005151907 | 11/2003 |
| WO | WO90/11354 | 10/1990 |
| WO | WO91/01140 | 2/1991 |
| WO | WO 91/06666 | 5/1991 |
| WO | WO91/06667 | 5/1991 |
| WO | WO93/04169 | 3/1993 |
| WO | WO95/22611 | 8/1995 |
| WO | WO96/34035 | 10/1996 |
| WO | WO96/39101 | 12/1996 |
| WO | WO 99/03973 | 1/1999 |
| WO | WO99/64566 A2 | 12/1999 |
| WO | WO00/17325 A1 | 3/2000 |
| WO | WO00/27999 A2 | 5/2000 |
| WO | WO 00/38762 | 7/2000 |
| WO | WO 00/69335 | 11/2000 |
| WO | WO00/73421 | 12/2000 |
| WO | WO 01/21767 | 3/2001 |
| WO | WO01/93909 | 12/2001 |
| WO | WO 02/46373 | 6/2002 |
| WO | WO 02/63962 | 8/2002 |
| WO | WO 02/064755 | 8/2002 |
| WO | WO03/042405 | 5/2003 |
| WO | WO03/089619 | 10/2003 |
| WO | WO 03/102151 | 12/2003 |
| WO | WO2004/087896 | 10/2004 |
| WO | WO2006/015214 | 2/2005 |
| WO | WO2005/042703 | 5/2005 |
| WO | WO2005042703 | 5/2005 |
| WO | WO2005/105992 | 11/2005 |
| WO | WO2006/015214 | 2/2006 |
| WO | WO 2006/111706 A | 10/2006 |
| WO | WO 2007/244441 | 3/2007 |
| WO | WO 2007/047468 | 4/2007 |
| WO | WO 2007/056578 | 5/2007 |
| WO | WO 2007/071048 | 6/2007 |
| WO | WO 2007/073552 | 6/2007 |
| WO | WO 2007/076522 | 7/2007 |
| WO | WO 2007/087293 | 8/2007 |
| WO | WO 2008/051568 | 5/2008 |
| WO | WO 2008/060541 | 5/2008 |
| WO | WO 2008/100497 | 8/2008 |

| | | | |
|---|---|---|---|
| 2006/0024280 | A1 | 2/2006 | West |
| 2006/0060494 | A1 | 3/2006 | Goodman et al. |
| 2006/0078993 | A1 | 4/2006 | Phan et al. |
| 2006/0153816 | A1 | 7/2006 | Brown et al. |
| 2006/0153817 | A1 | 7/2006 | Kihm et al. |
| 2006/0153818 | A1 | 7/2006 | Dhanaraj et al. |
| 2006/0154366 | A1 | 7/2006 | Brown et al. |
| 2006/0154367 | A1 | 7/2006 | Kihm et al. |
| 2006/0166361 | A1 | 7/2006 | Seyda et al. |
| 2006/0171930 | A1 | 8/2006 | Seyda et al. |
| 2006/0188983 | A1 | 8/2006 | Harris et al. |
| 2006/0222634 | A1 | 10/2006 | Clarke et al. |
| 2006/0223177 | A1 | 10/2006 | Harris |
| 2006/0233765 | A1 | 10/2006 | Messina et al. |
| 2006/0233766 | A1 | 10/2006 | Messina et al. |
| 2006/0234376 | A1 | 10/2006 | Mistry et al. |
| 2006/0263337 | A1 | 11/2006 | Maziarz et al. |
| 2006/0281178 | A1 | 12/2006 | Sakuragawa et al. |
| 2007/0009494 | A1 | 1/2007 | Mistry |
| 2007/0014771 | A1 | 1/2007 | Mistry |
| 2007/0020225 | A1 | 1/2007 | Abramson et al. |
| 2007/0021704 | A1 | 1/2007 | Hariri et al. |
| 2007/0021762 | A1 | 1/2007 | Liu et al. |
| 2007/0031384 | A1 | 2/2007 | Atala et al. |
| 2007/0036767 | A1 | 2/2007 | Mistry |
| 2007/0038298 | A1 | 2/2007 | Sulner et al. |
| 2007/0041954 | A1 | 2/2007 | Ichim |
| 2007/0043328 | A1 | 2/2007 | Goodman et al. |
| 2007/0053888 | A1 | 3/2007 | Hariri |
| 2007/0060616 | A1 | 3/2007 | Bennett et al. |
| 2007/0092497 | A1 | 4/2007 | Hariri |
| 2007/0092967 | A1 | 4/2007 | Han et al. |
| 2007/0116682 | A1 | 5/2007 | Atala et al. |
| 2007/0122903 | A1 | 5/2007 | Rezania et al. |
| 2007/0134210 | A1 | 6/2007 | Heidaran et al. |
| 2007/0141700 | A1 | 6/2007 | Harmon |
| 2007/0160588 | A1 | 7/2007 | Kihm |
| 2007/0190034 | A1 | 8/2007 | Paludan et al. |
| 2007/0190042 | A1 | 8/2007 | Edinger et al. |
| 2007/0190649 | A1 | 8/2007 | Gage |
| 2007/0253931 | A1 | 11/2007 | Varney et al. |
| 2007/0264269 | A1 | 11/2007 | Harmon et al. |
| 2007/0275362 | A1 | 11/2007 | Edinger et al. |
| 2007/0287176 | A1 | 12/2007 | Rezania |
| 2007/0292399 | A1 | 12/2007 | Heidaran et al. |
| 2007/0292910 | A1 | 12/2007 | Heidaran et al. |
| 2008/0032401 | A1 | 2/2008 | Edinger et al. |
| 2008/0044848 | A1 | 2/2008 | Heidaran |
| 2008/0069895 | A1 | 3/2008 | Liu et al. |
| 2008/0131410 | A1 | 6/2008 | Hariri |
| 2008/0131522 | A1 | 6/2008 | Liu et al. |
| 2008/0131966 | A1 | 6/2008 | Hariri |
| 2008/0145934 | A1 | 6/2008 | Harris et al. |
| 2008/0152624 | A1 | 6/2008 | Paludan et al. |
| 2008/0152629 | A1 | 6/2008 | Edinger et al. |
| 2008/0166328 | A1 | 7/2008 | Harmon et al. |
| 2008/0175824 | A1 | 7/2008 | Heidaran et al. |
| 2008/0181935 | A1 | 7/2008 | Bhatia et al. |
| 2008/0181967 | A1 | 7/2008 | Liu et al. |
| 2008/0206343 | A1 | 8/2008 | Edinger et al. |
| 2008/0208158 | A1 | 8/2008 | Goodman et al. |
| 2008/0213228 | A1 | 9/2008 | Edinger et al. |
| 2008/0226595 | A1 | 9/2008 | Edinger et al. |
| 2009/0053805 | A1 | 2/2009 | Hariri |
| 2009/0104164 | A1 | 4/2009 | Zhang et al. |
| 2009/0136471 | A1 | 5/2009 | Heidaran et al. |
| 2009/0142831 | A1 | 6/2009 | Hariri |
| 2009/0226406 | A1 | 9/2009 | Hariri |
| 2009/0252710 | A1 | 10/2009 | Zhang et al. |
| 2009/0263361 | A1 | 10/2009 | Lee et al. |
| 2010/0047213 | A1 | 2/2010 | Zeitlin et al. |

OTHER PUBLICATIONS

U.S. Appl. No. 11/580,588, filed Oct. 13, 2006, Paludan.
U.S. Appl. No. 11/580,625, filed Oct. 13, 2006, Heidaran.
U.S. Appl. No. 11/648,802, filed Dec. 28, 2006, Heidaran.
U.S. Appl. No. 11/648,804, filed Dec. 28, 2006, Edinger.
U.S. Appl. No. 11/648,812, filed Dec. 28, 2006, Heidaran.
U.S. Appl. No. 11/648,813, filed Dec. 28, 2006, Edinger.
U.S. Appl. No. 11/648,824, filed Dec. 28, 2006, Heidaran.
Abkowitz, "Can Human Hematopoietic Stem Cells Become Skin, Gut, or Liver Cells?" N. Engl. J. Med. 346(10):770-2 (2002)
Addison, et al., "Metabolism of Prednisolone by the Isolated Perfused Human Placental Lobule." J. Ster. Biochem, Mol. Biol., vol. 39, No. 1, pp. 83-90 (1991).
Barry, "Where Do All the Placentas Go?" Canadian Journal of Infection Control 9(l);8-10 (1994).

Belvedere, et al., "Increased Blood Volume and CD34(+)CD38(-) Progenitor Cell Recovery Using a Novel Cord Blood Collection System." Stem Cells, 18(4):245-251 (2000).

Chao, et al., "Stem Cell Transplantation (Cord Blood Transplants)." American Society of Hematololgy, Hematology 2004, p. 354-71.

Chin et al., "Enhanced Interferon Production and Lymphokine-Activated Cytotoxicity of Human Placental Cells," *Cellular Immunology* 113:1-9 (1988).

Contractor, et al., "A Comparison of the Effects of Different Perfusion Regimes on the Structure of the Isolated Human Placental Lobule." Cell Tissue Res. 237: 609-617 (1984).

Cosma, et al., "Use and Application of Stem Cells in Toxicology." SOT 2003 Annual Meeting, p. 4, Abstract 19.

Davila, et al., "Use and Application of Stem Celts in Toxicology." Toxicological Sciences 79, 214-223 (2004).

De Coppi, et al., "Amniotic Fluid and Chorionic Villi Derived Human Stem Cells for the Engineering of Tissues in Vivo." The Journal of Urology, vol. 171, No. 4, Supplement, Saturday, May 8, 2004, p. 21, Abstract 81.

De Coppi, et al., "Human Embryonic and Fetal Stem-Cell Isolation from Amniotic Fluid and Placenta for Tissue Reconstruction." Urology and Reproductive Surgery, vol. 195, No. 3S, Sep. 2002, p. S93.

De Coppi et al., "Human fetal stem cell isolation from amniotic fluid for tissue reconstruction," *J. Urology* 167(4 Supp.) (Abstract 338) (2002).

De Coppi, et al., "Pluripotent Stem Cells Derived from Human Chorionic Villi and Amniotic Fluid for Tissue Engineering Applications." Experimental Biology/IUPS 2005: Meeting Abstracts, A1366, Abstract 781.7.

De Filippo, et al., "Total Penile Urethra Replacement with Autologous Cell-Seeded Collagen Matrices." Urology and Reproductive Surgery, vol. 195, No. 3S, Sep. 2002, p. S95.

Dushnik-Levinson, et al., "Embryogenesis in Vitro: Study of Differentiation of Embryonic Stem Cells." Biol. Neonate. 67(2):77-83.

Elchalal, et al., "Postpartum Umbilical Cord Blood Collection for Transplatnation: A Comparison of Three Methods." Am. J. of Obstetrics & Gyn., 182(1 Pt. 1): 227-232.

Hatzopoulos, et al., "Isolation and Characterization of Endothelial Progenitor Cells from Mouse Embryos." Development. 125(8): 1457-68 (1998).

Himori, et al. Chemotherapeutic Susceptibility of Human Bone Marrow Progenitor Cells and Human Myelogenous Leukemia Cells (HL-60) in Co-Culture: Preliminary Report. Int. J. Cell Cloning. 2(4):254-62 (1984).

Hirashima, et al., "Maturation of Embryonic Stem Cells into Endothelial Cells in an In Vitro model of Vasculogenesis." Blood. 93(4):1253-63 (1999).

Koh, et al., "Parthenolgenetically Derived Stem Cells for Urologic Reconstruction." The Journal of Urology, vol. 171, No. 4, Supplement, Saturday, May 8, 2004, p. 21, Abstract 81.

Korbling, et al., "Hepatocytes and Epithelial Cells of Donor Origin in Recipients of Peripheral-Blood Stem Cells." N. Engl. J. Med. 346(10):738-46 (2002).

Melchner, et al., "Human Placental Conditioned Medium Reverses Apparent Commitment to Differentiation of Human Promyeloctic Leukemia Cells (HL60)." Blood, 66(6):1469-72 (1985).

Miki, et al., "Isolation of Multipotent Stem Cells from Placenta." AASLD Abstracts, Hepatology, Oct. 2003, Abstract 279, p. 290A.

Miki, et al., "Production of Hepatocytes from Human Amniotic SteM Cells." Hepatology, Abstract 20, vol, 36, No. 4, Pt. 2, 2002.

Miki, et al,, "Stem Cell Characteristics of Amniotic Epithelial Cells." Stem Cells Express, published online Aug. 9, 2005; doi:10. 1634/stemcells.2004-0357.

Moore, et al., "A Simple Technique for Isolation of Maternal Intervillous Blood Mononuclear Cells from Human Placentae." J. Immunol. Methods, 209: 93-104 (1997).

Reyes, et al., "Origin of Endothelial Progenitors in Human Postnatal Bone Marrow." J. Clin. Invest. 109(3):337-46.

Sakuragawa et al., "Expression of markers for both neuronal and glial cells in human amniotic epithelial cells," *Neuroscience Letters* 209:9-12 (1996).

Sakuragawa et al., "Human amniotic epithelial cells are promising transgene carriers for allogenic cell transplantation into liver," *J. Hum. Genet.* 45:171-176 (2000).

Shamblott et al., "Derivation of Pluripotent Stem Cells from Cultured Human Primordial Germ Cells." Proc. Nat'l. Acd. Sci. U S A. 95(23):13726-31 (1998).

Stager, "Transforming Growth Factor-Beta in the Early Mouse Embryo: Implications for the Regulation of Muscle Formation and Implantation." Dev. Genet. 14(3):212-24 (1993).

ScienCell—Human Amniotic Epithelial Cells. http://www.sciencellonline.com/products/7100.htm.

Thomson, et al., "Embryonic Stem Cell Lines Derived from Human Blastocysts." Science 282(5391):1145-47 (1998).

Turner, et al., "A Modified Harvest Technique for Cord Blood Hematopoietic Stem Cells." Bone Marrow Transplantation, 10:89-91.

Viacord, "Unbilical Cord Blood Can Save Lives." Informational Brochure, Boston: ViaCell CENTR-BR R1 (Oct. 2001).

Wang, et al., "Enhanced Recovery of Hematopoietic Progenitor and Stem Cells from Cultivated Postpartum Human Placenta," Blood, 98:(11/1): 183a, abstract No. 769 (2001).

Ye, et al., "Recovery of Placental-Derived Adherent Cells with Mesenchymal Stem Cell Characteristics." Blood, 98(11/1): 147b, abstract No. 4260 (2001).

Anker In'TP et al. "Isolation of Mesenchymal Stem Cells of Fetal or Maternal Origin from Human lacenta, " Stem Cells, Alphamed Press, Dayton, OH. US. vol. 22, No. 7, 004, pp. 1338-1345.

Clark David A et al, "Placental trophoblast from successful human pregnancies expresses the tolerance signaling molecule, CD200 (OX-2)" American Journal of Reproductive immunology, Munksgaard International Publishers, Copenhagen. DK, vol. 50, No. 3, Sep. 2003, pp. 187-195, XP002430047 ISSN: 1046-7408.

Database WPI Week 200357 Derwent Publications Ltd., London, GB, AN 2003-59905 & CN 1 407 888 A (Zhou S) Apr. 2, 2003.

Ende, "Pooled ambitical cord blood as a possible universal donor for marrow reconstitution and use in nuclear accidents," *Life Sciences* 69:1531-1539 (2001).

Erices et al., "Mesenchymal progenitor cells in human umbilical cord blood," *Br. J. Haemotol.* 109(1):Abstract (2000).

Fasouliotis et al., "Human umbilical cord blood banking and transplantation: a state of the art," *Eur. J. Obstet. Gynecol. Reprod. Biol.* 90(1):13-25 (2000).

Frank H G. et al., "Cell culture models of human trophoblast: primary culture of trophoblast—a workshop report." Placent Apr. 2001, vol. 22 Suppl A. Apr. 2001, pp. S107-S109, XP002443188 ISSN: 0143-4004.

Hoek R. M, et al., "Down-regulation of the macrophage lineage though interaction with OX2 (CD200)" Science, American Association for the ADvancement of Science. US, vol. 290. No. 5497, Dec. 1, 2000, pp. 1768-1771. XP002263649 ISSN:0036-8075.

International Preliminary Report on Patentability from PCT/US2006/049491 dated Jan. 14, 2008.

Li Chang Dong et al. "Mesenchymal stem cells derived from human placenta suppress allogeneic umbilical cord blood lymphocyte preliferation," Cell Research—Xibao Yanjiu Beijing. CN. vol. 15, No. 7. Jul. 2005, pp. 539-547. XP009080356 ISSN: 1001-0602.

Lin Yi. et al. "Murine CD200(+)CK7(+) trophoblasts in a poly (I:C)-induced embryo resorption model." Reproduction (Cambridge), vol. 130, No. 4, Oct. 2005, pp. 529-537, XP002443406 ISSN: 1470-1626.

Kawata et al., "Transcriptional Control of HI.A-A,B,C Antigen in Human Placental Cytotrophoblast Isolated Using Trophoblast-and HI.A-Specitic Monoclonal Antibodies and the Fluorescence-Activated Cell Sorter," *J. Exp. Med.* 160(3):633-51 (1984).

Pittenger, M. F., et al, "Multilineage Potential of Adult Human Mesenchymal Stem Cells." *Science* (1999) U.S. vol. 284, No. 5411. pp. 143-147.

Woods et at., "Osomometric and permeability characteristics of human placental/umbilical cord blood CD34+ cells and their application to cyropreservation," *J. Hematother. Stem Cell Res.* 9(2):161-173 (2000).

Yen B. Linju et al, "Isolation of multipotent cells from human term placenta" Stem Cells (Dayton, Ohio) 2005, vol. 23, No. 1. Jan. 2005, pp. 3-9, XP002443187 ISSN: 1065-5099.

Zhang Yi et al. "Human placenta-derived mesenchymal progenitor cells support culture expansion of long-term culture-initiating cells from cord blood CD34+ Cell" Experimental Hematology, New, NY, US, vol. 32, No. 7. Jul. 2004, pp. 657-664, XP002389863 ISSN: 0301-472X.

Office Action dated May 7, 2003 in U.S. Appl. No. 10/004,942, now U.S. Patent No. 7,045,148.

Office Action dated Dec. 5, 2003 in U.S. Appl. No. 10/004,942, now U.S. Patent No. 7,045,148.

Office Action dated Jun. 15, 2004 in U.S. Appl. No. 10/00,942, now U.S. Patent No. 7,045,148.

Office Action dated Dec. 16, 2004 in U.S. Appl. No. 10/004,942, now U.S. Patent No. 7,045,148.

Office Action dated Jun. 20, 2005 in U.S. Appl. No. 10/004,942, now U.S. Patent No. 7,045,148.

Notice of Allowance in U.S. Appl. No. 10/004,942, now U.S. Patent No. 7,045,148.

Office Action dated Sep. 23, 2004 in UL.S. Appl. No. 10/074,976, now US Patent No. 7,311,904.

Office Action dated Jan. 5, 2006 in U.S. Appl. No. 10/074,976, now US Patent No. 7,311,904.

Office Action dated Sep. 20, 2006 in US Patent Application No. 10/074,976, now US Patent No. 7,311,904.

Office Action dated Mar. 27, 2007 in US Patent Application No. 10/074,976, now US Patent No. 7,311,904.

Notice of Allowance in U.S. Appl. No. 10/074,976, now US Patent No. 7,311,904.

Office Action dated Jan. 29, 2006 in U.S. Appl. No. 10/366,671, now US Patent No. 7,311,905.

Office Action dated Oct. 10, 2006 in U.S. Appl. No. 10/366,671, now US Patent No. 7,311,905.

Office Action dated May 14, 2007 in U.S. Appl .No. 10/366,677, now US Patent No. 7,311,905.

Notice of Allowance in U.S. Appl. No. 10/366,677, now US Patent No. 7,311,905.

Office Action dated Jan. 19, 2006 in U.S. Appl. No. 10/640,428, now US Patent No. 7,255,879.

Office Action dated Oct. 18, 2006 in U.S. Appl. No. 10/640,428, now US Patent No. 7,255,879.

Notice of Allowance in U.S. Appl. No. 10/640,428, now US Patent No. 7,255,879.

Office Action dated Oct. 4, 2005 in U.S. Appl. No. 10/721,144.
Office Action dated Jan. 11, 2006 in U.S. Appl. No. 10/721,144.
Office Action dated Jun. 14, 2006 in U.S. Appl. No. 10/721,144.
Office Action dated Dec. 28, 2006 in U.S. Appl. No. 10/721,144.
Office Action dated Jun. 27, 2007 in U.S. Appl. No. 10/721,144.
Office Action dated Feb. 5, 2008 in U.S. Appl. No. 10/721,144.
Office Action dated Apr. 20, 2007 in U.S. Appl. No. 11/187,400.
Office Action dated Jan. 4, 2008 in U.S. Appl. No. 11/187,400.
Office Action dated Dec. 13, 2007 in U.S. Appl. No. 10/874,828.
Office Action dated Apr. 6, 2007 in U.S. Appl. No. 10/874,828.
Office Action dated Jun. 12, 2006 in U.S. Appl. No. 10/874,828.

Aggarwal et al., "Human Mesenchymal Stem Cells Modulate Allogeneic Immune Cell Responses," *Blood*, 2005: 105(4):1815-22.

Carter, et al., "Characterization of MSC Potential to Treat GVHD Using Molecular Markets Linked to MSC-Mediated Immunosuppression in Vitro," *Blood*, 2005; 1061(11) part 2, Abstract No. 4322,160B.

Chen, et al., "Therapeutic Benefit of Intravenous Administration of Bone Marrow Stromal Cells after Cerebral Ischemia in Rats," *Stroke*, 2001; 32(4):1005-11.

Davies, et al., "Engraftment and Survival After Unrelated-Donor Bone Marrow Transplantation: A Report from the National Marrow Donor Program," *Blood*, 2000; 96(13): 4096-4102.

Herrera, et al., "Mesenchymal Stem Cells Contribute to the Renal Repair of Acute Tubular Epithelial Injury," *Int. J. Mol. Med.*, 2004: 14(6):1035-41.

Hoynowski, et al., "Characterization and Differentiation of Equine Umbilical Cord-Derived Matrix Celis," *Biochemical and Biophysical Research Communications*, 2007; 362:347-53.

In'T Anker, et al., "Isolation of Mesenchymal Stem Cells of Fetal or Maternal Origin from Human Placenta," *Stem Cells*, 2004; 22:1338-45.

Iwasaki, "Recent Advances in the Treatment of Graft-Versus-Host Disease." *Clin. Med. Res.*, 2004; 2(4):243-52.

Le Blanc, et al., "Treatment of Severe Acute Graft-Versus-Host Disease With Third Party Haploidentical Mesenchvmal Stem Cells," *Lancet*, 2004; 363(9419):1439-41.

Li, et al., "Mesenchymal Stem Cells Derived From Human Placenta Suppress Allogenic Umbilical Cord Blood Lymphocyte Proliferation," *Cell Research*, 2005: 15(7):539-47.

Ma, et al., "Human Umbilical Cord Wharton's Jelly-Derived Mesenchymal Stem Cells Differentiation into Nerve-Like Cells," *Chinese Med. Jour.*, 2005; 118(23):1987-93.

Mackay et al., "Chondrogenic Differentiation of Cultured Human Mesenchymal Stem Cells from Marrow," *Tissue Engineering*, 1998; 4(4):415-28.

Morigi, et al., "Mesenchymal Stem Cells are Renotropic, Helping to Repair the Kidney and Improve Function in Acute Renal Failure," *J. Am. Soc. Nephrol.*, 2004; 15(7):1794-1804.

Morishima et al., "The Clinical Significance of Human Leukocyte Antigen (HLA) Allele Compatibility in Patients Receiving a Marrow Transplant from Serologically HLA-A, HLA-B, and HLA-DR Matched Unrelated Donors," *Blood*, 2002; 99(11):4200-06.

Ninichuk, et al., "Multipotent Mesenchymal Stem Cells Reduce Interstitial Fibrosis but do not Delay Progression of Chronic Kidney Disease in Collagen4a3-Deficient Mice," *Kidney Int.*, 2006; 70(1):121-29.

Panepucci, et al., "Comparison of Gene Expression of Umbilical Cord Vein and Bone Marrow-Derived Mesenchymal Stem Cells," *Stem Cells*, 2004; 22(7):1263-78.

Pera, et al, "Human Embryonic Stem Cells," *J. Cell Science*, 2000; 113:5-10.

Pountos, et al., "Mesenchymal Stem Cell Tissue Engineering: Techniques for Isolation, Expansion and Application," *Injury Int. J. Care Injured*, 2007; 38(Supp. 4):S23-33.

Toma, et al, "Human Mesenchymal Stem Cells Differentiate to a Cardiomyocyte Phenotype in the Adult Marinen Heart," *Circulation*, 2002; 105:93-98.

Ulloa-Montoya, et al, "Culture Systems ibf Ploripotent Stem Cells," *Journal if Bioscience and Bioengineering*, 2005; 100(1):12-27.

Zhang, et al, "Efficient Adena-Associated Virus-Mediated Gene Expression in Human Placenta-Derived Mesenchvmal Cells," *Microbiol. Immunol.*, 2003: 47(1):109-16.

Zhang, et al, "Comparison of Mesenchymal Stem Cells from Human Placenta and Bone Marrow." *Chinese Medical Journal*, 2004; 117(6):882-87.

U.S. Appl. No. 09/659,904, filed Sep. 12, 2000, Hariri.
U.S. Appl. No. 12/187,337, filed Aug. 6, 2008, Heidaran et al.
U.S. Appl. No. 12/240,956, filed Aug. 29, 2008, Zhang et al.
U.S. Appl. No. 12/267,499, filed Nov. 7, 2008, Heidaran et al.
U.S. Appl. No. 12/396,397, filed Mar. 2, 2009, Hariri et al.

Ashihara et al., "Successful Peripheral Blood Stem Cell Transplantation for Myelodysplastic Syndrome," *Bone Marrow Transplantation* 24(12): 1343-1345 (1999).

Bailo el at., "Engraftment Potential of Human Amnion and Chorion Cells Derived from Term Placenta," *Transplantation* 78:1439-1148 (2004).

Ballin et al., "Autologous Umbilical of Mesenchymal Stem/Progenitor Cells in Human First-Trimester Fetal Blood, Liver, and Bone Marrow." *Arch. Dis. Child Fetal Neonatal. Ed.* 73(3):F181-f183 (1995).

Campagnoli et al., "Identification of Mesenchymal Stem/Progenitor Cells in Human First-Trimester Fetal Blood, Liver, and Bone. Marrow," *Blood* 98(8):2396-402 (2001).

Caplan, "The Mesengenic Process," *Clin. Plast. Surg.* 21(3):429-435 (1994).

Chen et al. "Intravenous Administration of Human Umbilical Cord Reduces Behavioral Deficits after Stroke in Rats," *Stroke* 32(11):2682-2688 (2001).

Chen et al., "The Potential for the Use of Mononuclear Cells from Human Umbilical Cord Blood in the Treatment of Amyotrophic Lateral Sclerosis is SODI Mice," *J. Med.* 31(1-2):21-30 (2000).

Czarneski et al., "Efects of Cord Blood Transfer on the Hematopoietic Recovery Following Sublethal Irradiation in MRL. Ipr/Ipr Mice," *Proc. Soc. Exp. Biol. Med.* 220(2):79-87 (1999).

Davani at al., "Mesenchymal Progenitor Cells Differentiate into an Endothelial Phenotype, Enhance Vascular Density, and Improve Heart Function in a Rat Cellular Cardiomyoplasty Model," *Circulation* 108[suppl II]: II-253-II-258 (2003).

Davies et al. "Thalidomide and Immunomodulatory Derivatives Augment Natural Killer Cell Cytotoxicity in Multiple Myceloma," *Blood* 98(1):210-216 (2001).

De Wynter et al., "CD34+AC133+ Cells Isolated from Cord Blood are Highly Enriched in Long-Term Culture-Initiating Cells, NOD/SCID-Repopulating Cells and Dendritic Cell Progenitors," *Skin Cells* 16(6):387-396 (1998).

Drake et al., "Human Placental Cytotrophoblasts Attract Monocytes and CD56, (Bright) Natural Killer Cells Via the Acions of Monocyte Inflammatory Protein I Alpha," *J. Exp. Med.* 193(10):1199-1212 (2001).

Ende et al., "Human Umbilical Cord Blood Cells Alzheimer's Disease in Transgenic Mice," *J. Med.* (2001) 32(3-4):241-7.

Ende et al., "Human Umbilical Cord Blood Cells Ameliorate Huntington's Disease in Transgenic Mice," *J. Med.* 32(3-4):231-240 (2001).

Ende at al., "Human Umbilical Cord Blood Effect on SOD Mice (Amyotrophic Lateral Sclerosis)," *Life Sci.* 67(1);53-59 (2001).

Ende et al., "Parkinson's Disease Mice and Human Umbilical Cord Blood," *Journal of Medicine* 33(1-4):173-180 (2002).

Ende et al., "The Effect of Human Cord Blood on SJL/J Mice After Chemoablation and Irradiation and Its Possible Clinical Significance. " *Immunol. Invest.* 24(6):999-1012 (1995).

Ende, "Berashis Cells in Human Umbilical *Cord Blood* Vs. *Embryonic Stem Cells." J. Med.* 33(1-4):167-171 (2002).

Ende., "Collection of Umbilical Cord Blood for Transplantation," *Blood* 80(6):1623-1624 (1992).

Ende, "The Feasibility of Using Blood Bank Stored (4°C) Cord Blood, Unmatched for HLA for Marrow Transplantation," *Am. J. Clin. Pathol.* 111:773-781 (1999).

Gluckman et al., "Cord Blood Heamatopoietic Stem Cells: Biology and Transplantation," *In: Hematology, American Society of Hematology Education Program Book* (1998) p. 1-14.

Gluckman et al., "Results of Unrelated Umbilical Cord Blood Hematipoeietic Stem Cell Transplant," *Transform Cinique et Biologique* 8(3):146-154 (2001).

Hadiantonakis et al., "The Stem Cells of Early Embryos." *Differentiation* 68:159-166 (2001).

Hamada et al., "Mesenchymal Stem Cells (MSC) as Therapeutic Cytoreagents for Gene Therapy," *Cancer Sci.* 96:149-156 (2005).

Harbacheuski et al., "Placenta Derived Adherent Cells (PDACs) Supress Tumor Cells of Diverse Origin." *Blood* 108(11):288 (2006).

Hows, "Status of Umbilical Cord Blood Transplantation in the Yeat 2001," *J. Hematother. Stem. Cell Res.* 9(6):783-793 (2000).

Huss, "Perspectives on the Morphology and Biology of CD34 Negative Stem Cells," *J. Hematother. Stem. Cell. Res.* 9(6):783-793 (2000).

Igura et al, "Isolation and Characterization of Mesencymal Progenitor Cells from Chorionic Villi of Human Placenta," *Cytotherapy* 6(6) 543-553 (2004).

Jaiswai et al., "OsteogenicDifferentiation Purified, Culture-Expanded Human Mesenchymal Stem Cells in vitro," *J. Cell Biochem.* 64(2):295-312 (1997).

Koc et al., "Rapid Hematopoietic Recovery After Coinfusion of Autologous-Blood Stem Cells and Culture-Expanded Marrow Mesenchymal Stem Cells in Advanced Breast Cancer Patients Receiving High-Dose Chemotherapy," J Clin Oncol 18:307-316 (2000).

Kurtzberg, "Placental Bood as a Surce of Hmatopoietic Sem Cells Transplantation into Unrelated Recipients," *N. Engl. J. Med.* 335:157-166 (1996).

Law, E. et al., Stem Cell Symposium, State of New Jersey Commission on Science & Technology 2005 (Abstract).

Lazarus et al., "Contransplantation of HLA-Identical Sibling Culture-Expanded Mesenchymal Stem Cells and Hematopoietic Stem Cells in Hematologic Malignancy Patients," Biol Blood Marrow Transplant, 11(5):389-398 (2005).

Lebkowski et al., "Serum and Plasma Levels of FGF-2 and VEGF in Healthy Blood Donors," *Cancer J.* 7(Suppl 2):S83-S93 (2001).

Leonard et al., "The Role of ABC Transporters in Clinical Practice," *Oncologia.* 8:411-424 (2003).

Lorkowski et al., "ABCG Subfamily of Human ATP-Binding Cassette Proteins." *Pure Appl. Chem.* 74(11):2057-2081 (2002).

Ma et al., "The Development of an in vitro Human Placenta Model by the Cultivation of Human Trophoblasts in a Fiber-Based Bioreactor System," *Tissue Engineering* 5:91-102 (1995).

McMaster et al, "Human Placental HLA-G Expression is Restricted to Differentiated Cytotrophoblasts," *J. Immunol.* 154(8):3771-3778 (1995).

Melnik et al., "Evaluation of Elnants from Batch Separations of CD34(+) Cells from Human Cord Blood Using a Commercial, Immunomagnetic Cell Separation System," *Biotechnol. Prog.* 17(5):907-916 (2001).

Minguell et al., "Mesenchymal Stem Cells," *Exp. Biol. Med.* 226:507-520 (2001).

Muhlemann et al., "Cytomegalovirus in the Perfused Human Term Placenta in vitro," *Placenta* 16:367-373 (1995).

Myllynen "In Search of Models for Hepatic and Placental Pharmacokinetics," [Dissertation] University of Oala, (2003).

Nishishita et al., "A Potential Pro-Angiogenic Cell Therapy with Human Placenta-Derived Mesenchymal Cells," *Biochem, Biophys. Res. Commun.* 325(1):24-31 (2004).

Noort et al., "Mesenchymal Stem Cells Promote Engratment of Human Umbilical Cord Blood-Derived CD34+ Cells in NOD/SCID Mice." *Experimantal Hematology* 30(8):870-878 (2002).

Paludan et al., "Immune Suppression by Placenta Derived Adherent Cells (PDAC) Correlate with Monocyte Chemoattractant Protein-1 and IL-2 Secretion," *Blood* 108 (2006) (abstract only).

Papaioannou et al., "Stem Cells from Early Mammalian Embryos" Stem Cells Handbook:19-31 (2004).

Reyes et al., "Purification and ex vivo Expansion of Postnatal Human Marrow Mesodermanl Progenitor Cells," *Blood* 98(9):2615-2625 (2001).

Rossant, "Stem Cells from the Mammalian Blastocyst,-" *Stem Cell* 19:477-482 (2001).

Roth et al., "Human Placental Cytotrophoblats Produce the Immunosuppressive Cytokine Interliukin 10," *J. Exp. Med.* 184(2):539-54 (1996).

Rubenstein et al., "Processing and Cryopreservation of Placental/Umbilical Cord Blood for Unrelated Bone Marrow Reconstitution," *Proc. Natl. Acad. Sci. USA* 92:10119-10122 (1995).

Schtz et al, "Isolation and Cultivation of Endothelial Cells Derived from Human Placenta," *Eur. J. Cell Biol,* 395-401 (1996).

Sirchia et al., "Placental/Umbilical Cord Blood Transplantation," *Haematologica* 84:738-747 (1999).

Stanworth et al., "Stem Cells: Progress in Research and Edging towards the Clinical Setting," *Clin. Med.* 1(5):378-382 (2001).

Wang et al., "Mesenchymal Stem/Progenitor Cells in Human Cord Blood as Support for Ex Vivo Expansion of CD34+Hematopoietic Stem Cells and for Chondrogenic Differentiation," *Haematologica* 89(7):837-844 (2004).

Wantanabe et al, "Multilineage Potential of Human Placenta-Derived Mesenchymal Cells," *Blood* 100(11 ):517n (2002).

Advisory Action dated Jul. 12, 2004 in U.S. Appl. No. 10/076,180.
Office Action dated Aug. 28, 2003 in U.S. Appl. No. 10/076,180.
Office Action dated Jun. 20, 2005 in U.S. Appl. No. 10/076,180.
Office Action dated Mar. 18, 2004 in U.S. Appl. No. 10/076,180.
Office Action dated Oct. 20, 2004 in U.S. Appl. No. 10/076,180.
Advisory Action dated Feb. 2. 2007 in U.S. Appl. No. 10/366,671, now US Patent No. 7,311,905.
Notice of Allowance dated Oct. 30, 2008 in U.S. Appl. No. 10/411,655, now US Patent No. 7,498,171.
Office Action dated Feb. 28, 2005 in U.S. Appl. No. 10/411,655, now US Patent No. 7,498,171.
Office Action dated Jul. 11, 2007 in U.S. Appl. No. 10/411,655, now US Patent No. 7,498,171.
Office Action dated May 18, 2006 in U.S. Appl. No. 10/411,655, now US Patent No. 7,498,171.
Office Action dated Nov. 20, 2006 in U.S. Patent Appl. No, 10/411,655, now US Patent No. 7,498,171.
Advisory Action dated Oct. 25, 2007 in U.S. Appl. No. 10/449,248.
Office Action dated Apr. 26, 2007 in U.S. Appl. No. 10/449,248.

Office Action dated Aug. 29, 2006 in U.S. Appl. No. 10/449,248.
Office Action dated Feb. 7, 2008 in U.S. Appl. No. 10/449,248.
Advisory Action dated Nov. 14, 2008 in U.S. Appl. No.10/511,354.
Office Action dated Dec. 5, 2007 in U.S. Appl. No. 10/511,354.
Office Action dated Feb. 17, 2009 in U.S. Appl. No. 10/511,354.
Office Action dated Jun. 2, 2008 in U.S. Appl. No. 10/511,354.
Advisory Action dated Jan. 29, 2007 in U.S. Appl. No. 10/511,355.
Office Action dated Aug. 4, 2006 in U.S. Appl. No. 10/511,355.
Office Action dated Dec. 6, 2005 in U.S. Appl. No. 10/511,355.
Office Action dated Sep. 5, 2017 in U.S. Appl. No. 10/511,355.
Advisory Action dated Feb. 20, 2007 in U.S. Appl. No. 10/640,428, now US Patent No. 7,255,879.
Advisory Action dated Feb. 6, 2006 in U.S. Appl. No. 10/721,144.
Office Action dated Apr. 2, 2009 in U.S. Appl. No. 10/721,144.
Notice of Allowance dated Oct. 14, 2008 in U.S. Appl. No. 10/874,828, now US Patent No. 7,468,276.
Office Action dated Sep. 9, 2008 in U.S. Appl. No. 10/874,828, now US Patent No. 7,468,276.
Advisory Action dated Sep. 8, 2008 in U.S. Appl. No. 11/187,400.
Office Action dated Feb. 20, 2009 in U.S. Appl. No. 11/187,400.
Office Action dated May 22, 2008 in U.S. Appl. No. 11/187,400.
Office Action dated Feb. 4, 2009 in U.S. Appl. No. 11/592,544.
Office Action dated Dec. 3, 2008 in U.S. Appl. No. 11/648,802.
U.S. Appl. No. 12/187,337, filed Aug. 6, 2008, Heidaran et al.
U.S. Appl. No. 12/618,664, filed Nov. 13, 2009, Hariri.
U.S. Appl. No. 12/624,359, filed Nov. 23, 2009, Hariri.
U.S. Appl. No.12/687,851, filed Jan. 14, 2010, Paludan et al.
Aboagye-Mathiesen et al., "Isolation and Characterization of Human Placental Trophoblast Subpopulations from First-Trimester Chorionic Villi," Clinical and Diagnostic Laboratory Immunology 3(1)14-22 (1996).
Aplin, "Implantation, trophoblast Differentiation and Haemochorial Placentation: Mechanistic Evidence in vivo and in vitro," Journal of Cell Science 99:681-692 (1991).
Battula et al., "Prospective Isolation and Characterization of Mesenchymal Stem Cells from Human Placenta Using a Firzzled-9-Specific Monoclonal Antibody," Differentiation 76:326-336 (2008).
Bloxam et al., "Culture of Syncytiotrophoblast For The Study of Human Placental Transfer. Part I: Isolation and Purification of Cytotrophoblast," Placenta 18:93-98 (1997).
Bloxam, "Human Placental Trophoblast Culture: One-Sided and Two-Sided Models," Proceedings of the Nutrition Society 50:349-354 (1991).
Bullen et al., "Two-Sided Culture of Human Placental Trophoblast, Morphology, Immunocytochemistry and Permeability Properties," Placenta 11:431-450 (1990).
Caniggia et al., "Oxygen and Placental Development During the First Trimester: Implications for the Pathophysiology of Pre-Eclampsia." PubMed, Placenta 21(Suppl A):S25-30 (2000).
Cester et al., "Cation Transport Across Cultured Trophoblast Membrane in Preeclampsia," Clin. And Exper. Hyper. In Pregnancy, B11(1):59-69 (1992).
Chang, et al., "Placenta-Derived Multipotent Cells Exhibit Immunosuppressive Properties That Are Enhanced in the Presence of Interferon-gamma," Stem Cells 24:2466-2477 (2006).
Chies et al., "Sickle Cell Disease: A Chronic Inflammatory Condition," Medical Hypotheses 57(1):46-50 (2001).
Cotte et al., "Preparation of Highly Purified Cytotrophoblast from Humahn Placenta with Subsequent Modulation to Form Syncytiotrophoblast in Monolayer Cultures." In Vitro 16(8):639-646 (1980).
Dominici, et al., "Minimal Criteria for Defining Multipotent Mesenchymal Stromal Cells. The International Society for Cellular Therapy Position Statejment," Cytotherapy *(4):315-317 (2006).
Evans, "Stem Cell Therapy: Moving towards Reality," Am. J. Obstet. Gynecol. 194:662-663 (2006).
Fisher et al., "Adhesive and Degradatie Properties of Human Placental Cytotrophoblast Cells In Vitro," Journal od Cell Biology 109:891-902 (1989).
Frank H G, et al., "Cell culture models of human trophoblast: primary culture of trophoblast—a workshop report," Placent Apr. 2001, vol. 22 Suppl A, Apr. 2001, pp. S107- S109, XP002443188 ISSN: 0143-4004.
Genbacev et al., "Regulation of Human Placental Development by Oxygen Tension," 277(5332):1669-1672.
Greenwood et al., "Membrane Potential Difference and Intracellular Cation Concentrations in Human Placental Trophoblast Cells in Culture," Journal of Physiology 492.3:629-640 (1996).
Harun et al., "Cytotrophoblast Stem Cell Lines Derived from Human Embyonic Stem Cells and Their Capacityt o Mimic Invasive Implantation Events," Human Reproduction, Oxford University Press, pp. 1-10 (2006).
Hattori et al., "Molecular Cloning of Adipocyte-Derived Leucine Aminopeptidase Highly Related to Placental Leucine Aminopeptidase/Oxytocinase," J. Biochem. 125(5):931-938 (1999).
Hirano et al., "CD9 is Expressied in Extravillous Trophoblasts in Association with Integrin $\alpha 3$ and integrin $\alpha 5$," Molecular Human Reproduction 5(2):162-167 (1999).
Ino et al., "Expression of Placental Leucine Aminopeptidase and Adipocyte-Derived Leucine Aminopeptidase in Human Normal and Malignant Invasive Trophoblastic Cells" Laboratory Investigation 83(12):1799-1809 (2003).
James et al., "Cytotrophoblast Differentiation In The First Trimester of Pregnance: Evidence for Seperate Progenitros of Extravillous Trophoblast and Syncytiotrophoblast," Reproduction 130:95-130 (2005).
Jiang et al., "Hypoxia Prevents Induction of Aromatase Expression in Human Trophoblast Cells in Culture: Potential Nihibitory Role of the Hypoxia-Inducible Transcription Factor Mash-2 (Mammalian Achaete-Scute Homologous Protein-20," Molecular Endocrinology 14(10):1661-1673 (2019).
Jones et al., "Ultrastructure of the Normal Human Placenta," Electron Microsc. 4:129-178 (1991).
Kao et al., "The Human Villous Cytotrophoblast: Interactions with Extracellular Matrix Proteins, Endocrine Function: and Cytoplasmic Differentiation in the Absence of Syncytium Formation," Developmental Biology 130:693-702 (1988).
Kato et al., "Discordant Secretion of Placental Protein Hormones in Differentiating Trophoblasts in Vitro," Jounal of Clinical Endocrinology and Metabolism 68(4):814-820 (1989).
Kaufman et al., "Extravillous Trophoblast in The Human Placenta," Trophoblast Research 10:21-65 (1997).
Kliman et al., "Purification, Characterization, and In Vitro Differentiation of Cytotropholblasts from Human Term Placentae," Endocrinology 118(4):1567-1582 (1986).
Landon et al., "The Effects of Ethanol Methotrexate and Diphenylhydantoin on [$^{14}$C] Leucine Incorporation by Human Trophoblasst Cells Cultured in Vitro," British Journal of Obstetrics and Gynaecology 94:252-255 (1987).
Lipinski et al., "Human Trophoblast Cell-Surface Antigen Defined by Monoclonal Antibodies," Proc, Natl, Acad. Sci. USA, Medical Sciences 78(8).5147-5150 (1981).
Loke et al., "Identification of Cytotrophoblast Colonies in Cultures of Human Placental Cells Using Monoclonal Antibodies," Placenta 7:221-231 (1986).
Morgan et al., "Human Placental Cell Culture," Biochemical Society Transactions 12 (1984).
Morgan et at., "Long-Term Culture of Human Trophoblast Cells," British Journal of Obstetrics and Gynaecology 92:84-92 (1985).
Morrish et al., "Epidermal Growth Factor Induces Differentiation and Secretion of Human Chorionic Gonadotropin and Placental Lactogen in Normal Human Placenta," Journal of Clinical Endocrinology and Metabolism 65(6):1282-1290 (1987).
Morrish et al., "In Vitro Cultured Human Term Cytotrophoblast: A Model for Normal Primary Epitehlial Cells Demonstrating a Spontaneous Differentiation Programme that Requires EGF for Extensive Development of Syncytium," Placenta 18: 577-585 (1997).
Notice of Opposition by Farmindustria S.A. to corresponding claims filed in Peru; English translation May 5, 2008.
Oda et al., "Trophoblast Stem Cells," Methods in Enxymology 419(15):387-400 (2006).
Paludan, et al., "Placental Derived Stem Cells (PDAC) Suppress the Alto-MLR and the EBV Regression Assay," http://www.call4abstract.com/hem/finalpreview.php?absnum=552996 (2006).

Pande et al., "Isolation and Culture of Hamster Ectoplacental Cone Trophoblasts: an In Vitro Study on the Cell Types and Their Growth Pattern," Cell Prolif 29:163-171 (1996).

Pellegrini, et al., "FADD and Caspase-8 Are Required for Cytokine-Induced Proliferation of Hemopoietic Progenitor Cells," Blood 106(5):1581-1589 (2005).

Petroff et al., "Isolation and Culture of Term Human Trophoblast Cells," Methods in Molecular Medicine, Placenta and Trophoblast, 1(16):203-217 (2006).

Portmann-Lanz, et al., "Placental Mesenchymal Stem Cells as Potential Autologous Graft for Pre-and Perinatal Neuroregeneration" Am. J. Obstet Gynecol. 194:664-673 (2006).

Potgens et al., "Human Trophoblast Contains an Intracellular Protein Reactive with and Antibody against CD133-A Novel Marker for Trophoblast," Placenta 22:639-645 (2001).

Potgens et at., "Monoclonal Antibody CD133-2 (AC141) Against Hematopoeietic Stem Cell Antigen CD133 Shows Crossactivity with Cytokeratin 18," Journal of Histochemistry & Cytochemistry 50(8):1131-1134 (2002).

Quinn et at., "Mouse Trophoblast Stem Cells," Methods in Molecular Medicine 121(1):125-148 (2005).

Rachmilewitz et al., "Intermediate Cells During Cytotrphoblast Differentiation in Vitro," Cell Growth & Differentiation 4:395-402.

Rielland et al., "Trophoblast Stem Cell Derivation, Cross-species Comparison and Use of Nuclear Transfer: New Tools to Study Trophoblast Growth and Differentiation," Developmental Biology 322:1-10 (2008).

Ringler et al., "In Vitro Systems for the Study of Human Placental Endocrine Function," Endocrine Reviews 11(1):105-123.

Rong-Hao et at., "Establishment and Characterization of a Cytotrophoblast Cell Line From Normal Placenta of Human Origin." Human Reproduction 11(6):1328-1333 (1996).

Saric et at., "An IFN-y-induced Aminopeptidase in the ER, ERAP I, Trims Precusors to MHC Class l-presented Peptides," Nature Immunology 3(12):1169-1176 (2002).

Schulz et al., "Human Embryonic Stem Cells as Models for Trophoblast Differentiation," Placenta 29(Suppl A):S10-S16 (2008).

Soma, "Human Trophoblast in Tissue Culture," Obstetrics and Gynaecology 18(6):704-718 (1961).

Stromberg et al., "Isolation of Functional Human Trophoblast Cells and Their Partial Characterization in Primary Cell Culture," In Vitro 14(7):6331-638 (1978).

Sunderland et al., "HLA A, B, C Antigens Are Expresses on Nonvillous Trophoblast of the Early Human Placenta," Journal of Immunology 127(6):2614-2615 (1981).

Tarrade et al., "Characterization of Human Villous and Extravillous Trophoblasts Isolated from First Trimester Placenta," Laboratory Investigation 81(9):1199-1211 (2001).

Truman et al., "Human Placental Cytotrophoblast Cells: Identification and Culture," Arch Gynecol. Obstet. 246:39-49 (1989).

Truman et al., "The Effects of Substrate and Epidermal Growth Factor on Human Placental Trophoblast Cells in Culture," In Vitro Cellular & Developmental Biology 22(9):525-528 (1986).

Wiesmann, et al., "Effects of Caspase Inhibitors on Hematopoietic Engraftment After Short-Term Culture," Cell. Transplant. 11(4):351-358 (2002).

Xu et al., "BMP4 Initiates Human Embryonic Stem Cell Differentiation to Trophoblast," Nature Biology 20:1261-1264 (2002).

Xu, et al., "High Sensitivity of Megakaryocytic Progenitor Cells Contained in Placental/Umbilical Cord Blood to the Stresses During Cryopreservation," Bone Marrow Transplantation 34: 537-543 (2004).

Yeger et al., "Enzymatic Isolation of Human Trophoblast and Culture on Various Substrates: Comparison of First Trimester with Term Trophoblast," Placenta 10:137-151 (1989).

Yui et al., "Functional, Long-term Cultures of Human Term Trophoblasts Purified by Column-elimination of CD9 Expressing Cells," Placenta 15:231-246 (1994).

Advisory Action dated Jul. 12, 2004 in U.S. Appl. No. 10/076,180.

Advisory Action dated Feb. 2, 2007 in U.S. Appl. No. 10/366,671, now US Patent No. 7,311,905.

Notice of Allowance dated Oct. 30, 2008 in U.S. Appl. No. 10/411,655, now US Patent No. 7,498,171.

Office Action dated Feb. 28, 2008 in U.S. Appl. No. 10/411,655, now US Patent No. 7,498,171.

Office Action dated Jul. 11, 2007 in U.S. Appl. No. 10/411,655, now US Patent No. 7,498,171.

Office Action dated May 18, 2006 in U.S. Appl. No. 10/411,655, now US Patent No. 7,498,171.

Office Action dated Nov. 20, 2006 in U.S. Appl. No. 10/411,655, now US Patent No. 7,498,171.

Advisory Action dated Feb. 20, 2007 in U.S. Appl. No. 10/640,428, now US Patent No. 7,255,879.

Office Action dated Mar. 18, 2010 in U.S. Appl. No. 10/721,144.

Advisory Action dated Oct. 7,2009 in U.S. Appl. No. 10/721,144.

Advisory Action dated Aug. 17, 2009 in U.S. Appl. No. 10/721,144.

Office Action dated Sep. 9, 2008 in U.S. Appl. No. 10/874,828, now US Patent No. 7,468,276.

Notice of Allowance dated Oct. 14, 2008 in U.S. Appl. No. 10/874,828, now US Patent No. 7,468,276.

Notice of Allowance dated Aug. 12, 2009 in U.S. Appl. No. 11/187,400.

Non-Final Office Action dated Oct. 21. 2009 in U.S. Appl. No. 11/648,804.

Non-Final Office Action dated Jan. 22, 2010 in U.S. Appl. No. 11/648,824.

Garcia-Olmo et al., "Autologous Stem Cell Transplantation for Treatment of Rectovaginal Fistula in Perianal Crohn's Disease: A New Cell-based Therapy," Int, J. Colorectal Dis. 18:451-454 (2003).

Wulf at al., "Mesengenic Progenitor Cells Derived from Human Placenta," Tissue Engineering 10(7/8): 1136-1147 (2004).

Bossolasco et al., "Molecular and phenotypic characterization of human amniotic fluid cells and their differentitation potential," Cell Research 16:326-336 (2006).

Sapin, "Esterification of Vitamin A by the Human Placenta Involves Villous Mesenchymal Fibrlboasts," pediatric Research 48(4):565-572 (2000).

U.S. Appl. No. 12/622,352, filed Nov. 19, 2009, Abbot.

U.S. Appll. No. 12/823,063, filed Jun. 24, 2010, Hariri

U.S. Appl. No. 12/829,326, filed Jul. 1, 2010, Abbot.

U.S. Appl. No. 12/846,765, filed Jul. 29, 2010, Edinger et al.

U.S. Appl. No. 12/848,007, filed Jul. 30, 2010, Edinger et al.

Schwab, "Fast and Reliable Culture Method for Cells from 8-10 Week Trophoblast Tissue," Lancet 323:1082 (1984).

Sikkema-Raddatz, "Four Years'Cytogenetic Experience with the Culture of Chorionic Vilii." Prenatal Diagnosis 20:950-955 (2000).

Non Final Office Action dated Jun. 7, 2010 in U.S. Appl. No. 11/980,012.

Non Final Office Action dated Jul. 19, 2010 in U.S. Appl. No. 11/982,007.

Non Final Office Action dated May 24, 2010 in US Patent Application 11/982,211.

Non Final Office Action dated Jul. 15, 2010 in U.S. Appl. No. 11/982,291.

Non -Final Office Action dated May 20, 2010 in U.S. Appl. No. 11/648,804.

Abkowitz, "Can Human Hematopoietic Stem Cells Become Skin, Gut, or Liver Cells?" N. Engi. J. Med. 346(10):770-2 (2002).

Addison, et al., "Metabolism of Prednisolone by the Isolated Perfused Human Placental Lobule." J. Ster, Biochem, Mol. Biol., vol. 39, No. 1, pp. 83-90 (1991).

Barry, "Where Do All the Placentas Go?" Canadian Journal of Infection Control 9(l):8-10 (1994).

Belvedere, et al., "Increased Blood Volume and CD34(+)CD38(−) Progenitor Cell Recover Using a Novel Umbilical Cord Blood Collection System." Stem Cells, 18(4):245-251 (2000).

Chao, et al., "Stem Cell Transplantation (Cord Blood Transplants)," American Society of Hematololgy, Hematology 2004, p. 354-71.

Chin et al., "Enhanced Interferon Production and Lymphokine-Activated Cytotoxicity of Human Placental Cells," *Cellular Immunology* 113:1-9 (1988).

Contractor, et al., "A Comparison of the Effeets of Different Perfusion Regimes on the Structure of the Isolated Human Placental Lobule." Cell Tissue Res. 237: 609-617 (1984).

Cosma, et al., "Use and Application of Stem Cells in Toxicology." SOT 2003 Annual Meeting, p. 4, Abstract 19.

Davila, et al., "Use and Application of Stem Cells in Toxicology." Toxicological Sciences 79, 214-223 (2004).

De Coppi, et al., "Amniotic Fluid and Chorionic Villi Derived Human Stem Cells for the Engineering of Tissues in Vivo." The Journal of Urology. vol. 171. No. 4, Supplement, Saturday, May 8, 2004, p.21, Abstract 81.

De Coppi, et al., "Human Embryonic and Fetal Stem-Cell Isolation from Amniotic Fluid and Placenta for Tissue Reconstruction." Urology and Reproductive Surgery, vol. 195, No. 3S, Sep. 2002, p. S93.

De Coppi et al,, "Human fetal stem cell isolation from amniotic fluid for tissue reconstruction," J. Urology 167(4 Supp.) 85 (Abstract 338) (2002).

De Coppi, et al., "Pluripotent Stem Cells Derived from Human Chorionic Villi and Amniotic Fluid for Tissue Engineering, Applications." Experimental Biology/IUPS 2005: Meeting Abstracts, A1366, Abstract 781.7.

De Filippo, et al., "Total Penile Urethra Replacement with Autologous Cell-Seeded Collagen Matrices." Urology and Reproductive, vol. 195, No. 35, Sep. 2002, p. S95.

Dushnik-Levinson, et al., "Embryogenesis in Vitro: Study of Differentiation of Embryonic Stem Cells." Biol. Neonate. 67(2):77-83, 1995.

Elchalal, et al., "Postpartum Umbilical Cord Blood Collection for Transplatnation: A Comparsion of Three Methods." Am. j. of Obstetrics & Gyn., 182(1 Pt. 1): 227-232, (2000).

Hatzopoulos, et al., "Isolation and Characterization of Endothelial Progenitor Cells from Mouse Embryos," Development. 125(8): 1457-68 (1998).

Himori, et al. Chemotherapeutic Susceptibility of Human Bone Marrow Progenitor Cells and Human Myelogenous Leukemia Cells (HL-60) in Co-Culture: Preliminary Report. Int. J. Cell Cloning. 2(4):254-62 (1984).

Hirashima, et al., "Maturation of Embryonic Stem Cells Endothelial Cells in an In Vitro model of Vasculogenesis." Blood. 93(4):1253-63 (1999).

Koh, et al., "Parthenolgenetically Derived Stem Cells for Urologic Reconstruction." The Journal of Urology, vol. 171, No. 4, Supplement, Saturday, May 8, 2004, p. 21, Abstract 81.

Korbling et al., "Hepatocytes and Epithelial Cells of Donor Origin in Recipients of Peripheral-Blood Stem Cells." N. Engl. J. Med. 346(10):738-46 (2002).

Melchner, et al., "Human Placental Conditioned Medium Reverses Apparent Commitment to Differentiation of Human Promyeloctic Leukemia Cells (HL60)." Blood, 66(6):1469-72 (1985).

Miki, et al., "Isolation ofMultipotent, Stem Cells from Placenta." AASLD Abstracts, Hepatology, Oct. 2003, Abstract 279, p. 290A.

Miki, et al., "Production of Hepatocytes from Human Amniotic Stern Cells." HepatologyAbstract 20, vol. 36, No. 4, Pt. 2, 2002.

Miki, et al., "Stem Cell Characteristics of Amniotic Epithelial Cells." Stem Cells Express, published online Aug. 9, 2005; doi;10. 1634/stemcells.2004-0357.

Moore, et al., "A Simple Perfusion Technique for Isolation of Maternal Intervillous Blood Mononuclear Cells from Human Placentae." J. Immunol. Methods, 209: 93-104 (1997).

Reyes et , "Origin of Endothelial Progenitors in Human Postnatal Bone Marrow." J. Clin. Invest. 109(3):337-46, 2002.

Sakuragawa et al., "Expression of markers for both neuronal and glial cells in human amniotic epithelial cells." Neuroscience Letters 209:9-12 (1996).

Sakuragawa et al., "Human amniotic epithelial cells are promising transgene carriers for allogeneic cell transplantation into liver," J. Hum. Genet. 45:171-176 (2000).

Shamblott, et al., "Derivation of Pluripotent Stem Cells from Cultured Human Primordial Germ Cells." Proc. Nat'l. Acd. Sci. U S A. 95(23):13726-31 (1998).

Slager, "Transforming Growth Factor-Beta in the Early Mouse Embryo: Implications for the Regulation of Muscle Formation and Implantation." Dev. Genet. 14(3):212-24 (1993).

ScienCell—Human Amniotic Epithelial Cells, ScienCell Research Lab Catelog. 1995.

Thompson, et al., "Embryonic Stem Cell Lines Derived from Human Blastocytes." Science 282(5391):1145-49 (1998).

Turner, et al., "A Modified Harvest Technique for Cord Blood Hematopoietic Stem Cells." Bone Marrow Transplantation, 10: 89-91, (1992).

Viacord, "Umbilical Cord Blood Can Save Lives." Informational Brochure, Boston: ViaCell CENTR-BR R1 Oct. 1, 2001.

Wang, et al., "Enhanced Recovery of Hematopoietic Progenitor and Stem Cells from Cultivated Postpartum Human Placenta." Blood, 98:(11/1): 183a, abstract No. 769 (2001).

Ye, et al., "Recovery of Placental-Derived Adherent Cells with Mesenchymal Stem Cell Characteristics," Blood, 98(11/1 ): 147b, abstract No. 4260 (2001).

Extended European Search Report for EP Application No. 10182195.7-2401 (specification corresponding to U.S. Patent No. 7,468,276).

Extended European Search Report for EP Application No. 10182243.5-2401 (specification corresponding to U.S. Patent No. 7,468,276).

Extended European Search Report for EP Application No. 10182303.7-2401 (specification corresponding to U.S. Patent No. 7,468,276).

Extended European Search Report for EP Application No. 10182362.3-2401 (spec fication corresponding to U.S. Patent No. 7,468,276).

Extended European Search Report for EP Application No. 10182433.2-2401 (specification corresponding to U.S. Patent No. 7,468,276).

Extended European Search Report for EP Application No. 10182485.2-2401 (specification corresponding to U.S. Patent No. 7,468,276).

Extended European Search Report for EP Application No. 10183435.6-2401 (specification corresponding to U.S. Patent No. 7,045,148).

Extended European Search Report for EP Application No. 10183378.8-2401 (specification corresponding to U.S. Patent No. 7,045,148).

Extended European Search Report for EP Application No. 10183252.5-2401 (specification corresponding to U.S. Patent No. 7,311,904).

Extended European Search Report for EP Application No. 10183301.0-2401 (specification corresponding to U.S. Patent No. 7,311,904).

Extended European Search Report for EP Application No. 10184356.3-1222 (specification corresponding to U.S. Patent No. 7,311,905).

Extended European Search Report for EP Application No. 10185142.6-1222 (specification corresponding to U.S. Patent No. 7,311,905).

Abe et al. "Therapeutic potential of neurotrophic factors and neural stem cells against ischemic brain injury" Journal of Cerebral Blood Flow and Metabolism 29:1393-1408 (2000).

Conget et al. "Phenotypical and functional properties of human bone marrow mesenchymal progenitor cells" Journal of Cellular Physiology 181:67-73 (1999).

Denison et al. "Cytokine secretion by human fetal membranes, decidua and placenta at term" Human Reproduction 13(12):3560-3565 (1998).

Fassas et al. "Autologous stem cell transplantation in progressive multiple sclerosis—an interim analysis of efficacy" Journal of Clinical Immunology 20(1):24-30 (2000).

Hsieh et al. "Effects of glucose on placental hormones in the human term placenta in vitro" J. Formos. Med. Assoc. 96:309-313 (1997).

Jaroscak et al. "Preliminary characterization of the surface staining of placental derived adherent cells: a potential new source of stroma for umbilical cord blood (UCB) expansion," Blood 96(11, Pt 2) (2000).

Malek et al. "Lack of transport of erythropoietin across the human placenta as studied by an in vitro perfusion system," European Journal of Physiology 427:157-161 (1994).

Marmont "New horizons in the treatment of autoimmune diseases: Immunoablation and stem cell transplantation," Annual Review of Medicine 51:115-134 (2000).

Parolini et al. "Concise review: Isolation and characterization of cells from human term placenta: Outcome of the first international workshop on placenta derived stem cells" Stem Cells 26:300-311 (2008).

Ponticiello et al. "Gelatin-based resorbable sponge as a carrier matrix for human mesenchymal stem cells in cartilage regeneration therapy" Journal of Biomedical Materials Research 52:246-255 (2000).

Reubinoff et al. "Neural progenitors from human embryonic stem cells" Nature Biotechnology 19:1134-1140 (2001).

Semenov et al. "Multipotent mesenchymal stem cells from human placenta: critical parameters for isolation and maintenance of stemness after isolation" American Journal of Obstetrics & Gynecolocy 202:193.e1-13 (2010).

Xu et al. "Feeder-free growth of undifferentiated human embryonic stem cells" Nature Biotechnology 19:971-974 (2001).

Yin et al "AC133, a novel marker for human hematopoietic stem and progenitor cells" *Blood* 90(12):5002-5012 (1997).

Zhao et al. "Transplanted human bone marrow-derived adult stem cells survive and improve functional outcome in a rat model of cortical ischemic brain injury" *Experimental Neurology* 164(2):465-466 (2000).

Zhao et al. "Human bone marrow stem cells exhibit neural phenotypes after transplantation and ameliorate neurological deficits with ischemic brain injury in rats" *Abstracts of the Annual Meeting of the Society for Neuroscience* 26(No. 1/2):860.01 (2000).

* cited by examiner

US 8,057,788 B2

PLACENTAL STEM CELL POPULATIONS

This application is a continuation-in-part of U.S. application Ser. No. 10/640,428, filed Aug. 12, 2003, now U.S. Pat. No. 7,255,879, which is a division of U.S. application Ser. No. 10/076,180, filed Feb. 13, 2002, abandoned, which claims benefit of U.S. Provisional Application No. 60/268,560, filed Feb. 14, 2001, and which is a continuation-in-part of U.S. application Ser. No. 10/004,942, filed Dec. 5, 2001, now U.S. Pat. No. 7,045,148, which claims benefit of U.S. Provisional Application No. 60/251,900, filed Dec. 6, 2000; and is a continuation-in-part of U.S. application Ser. No. 10/074,976, filed Feb. 13, 2002, now U.S. Pat. No. 7,311,904, which claims benefit of U.S. Provisional Application No. 60/268,560, filed Feb. 14, 2001; and is a continuation-in-part of U.S. application Ser. No. 10/366,671, filed Feb. 13, 2003, now U.S. Pat. No. 7,311,905, which claims priority to U.S. application Ser. No. 10/076,180, filed Feb. 13, 2002, abandoned; and claims benefit of U.S. Provisional Application No. 60/754,968, filed Dec. 29, 2005; and claims benefit of U.S. Provisional Application No. 60/846,641, filed Sep. 22, 2006.

1. FIELD OF THE INVENTION

The present invention provides isolated placental stem cells, populations of placental stem cells, compositions comprising the stem cells, and methods of obtaining the stem cells.

2. BACKGROUND OF THE INVENTION

Human stem cells are totipotential or pluripotential precursor cells capable of generating a variety of mature human cell lineages. Evidence exists that demonstrates that stem cells can be employed to repopulate many, if not all, tissues and restore physiologic and anatomic functionality.

Many different types of mammalian stem cells have been characterized. See, e.g., Caplan et al., U.S. Pat. No. 5,486,359 (human mesenchymal stem cells); Boyse et al., U.S. Pat. No. 5,004,681 (fetal and neonatal hematopoietic stem and progenitor cells); Boyse et al., U.S. Pat. No. 5,192,553 (same); Beltrami et al., Cell 114(6):763-766 (2003) (cardiac stem cells); Forbes et al., J. Pathol. 197(4):510-518 (2002) (hepatic stem cells). Umbilical cord blood, and total nucleated cells derived from cord blood, have been used in transplants to restore, partially or fully, hematopoietic function in patients who have undergone ablative therapy.

3. SUMMARY OF THE INVENTION

The present invention provides isolated placental stem cells, populations of placental stem cells, compositions comprising the stem cells, and methods of obtaining the stem cells.

The invention first provides isolated stem cells, and cell populations comprising such stem cells, wherein the stem cells are present in, and isolatable from placental tissue (e.g., amnion, chorion, placental cotyledons, etc.) The placental stem cells exhibit one or more characteristics of a stem cell (e.g., exhibit markers associated with stem cells, replicate at least 10-20 times in culture in an undifferentiated state, differentiate into adult cells representative of the three germ layers, etc.), and can adhere to a tissue culture substrate (e.g., tissue culture plastic such as the surface of a tissue culture dish or multiwell plate).

In one embodiment, the invention provides an isolated placental stem cell that is $CD200^+$ or $HLA-G^+$. In a specific embodiment, said cell is $CD200^+$ and $HLA-G^+$. In a specific embodiment, said stem cell is $CD73^+$ and $CD105^+$. In another specific embodiment, said stem cell is $CD34^-$, $CD38^-$ or $CD45^-$. In another specific embodiment, said stem cell is $CD34^-$, $CD38^-$ and $CD45^-$. In another specific embodiment, said stem cell is $CD34^-$, $CD38^-$, $CD45^-$, $CD73^+$ and $CD105^+$. In another specific embodiment, said stem cell facilitates the formation of one or more embryoid-like bodies from a population of isolated placental cells comprising placental stem cells when said population is cultured under conditions that allow formation of embryoid-like bodies.

In another embodiment, the invention provides a population of isolated placental cells comprising, e.g., that is enriched for, $CD200^+$, $HLA-G^+$ stem cells. In various embodiments, at least 10%, at least 20%, at least 30%, at least 40%, at least 50% at least 60%, at least 70%, at least 80%, at least 90%, or at least 95% or more of said isolated placental cells are $CD200^+$, $HLA-G^+$ stem cells. In a specific embodiment of the above populations, said stem cells are $CD73^+$ and $CD105^+$. In another specific embodiment, said stem cells are $CD34^-$, $CD38^-$ or $CD45^-$. In a more specific embodiment, said stem cells are $CD34^-$, $CD38^-$, $CD45^-$, $CD73^+$ and $CD105^+$. In other specific embodiments, said population has been expanded, e.g., passaged at least once, at least three times, at least five times, at least 10 times, at least 15 times, or at least 20 times. In another specific embodiment, said population forms one or more embryoid-like bodies when cultured under conditions that allow formation of embryoid-like bodies.

In another embodiment, the invention provides an isolated stem cell that is $CD73^+$, $CD105^+$, and $CD200^+$. In a specific embodiment, said stem cell is $HLA-G^+$. In another specific embodiment, said stem cell is $CD34^-$, $CD38^-$ or $CD45^-$. In another specific embodiment, said stem cell is $CD34^-$, $CD38^-$ and $CD45^-$. In a more specific embodiment, said stem cell is $CD34^-$, $CD38^-$, $CD45^-$, and $HLA-G^+$. In another specific embodiment, said stem cell facilitates development of one or more embryoid-like bodies from a population of isolated placental cells comprising the stem cell when said population is cultured under conditions that allow formation of embryoid-like bodies.

In another embodiment, the invention provides a population of isolated placental cells comprising, e.g., that is enriched for, $CD73^+$, $CD105^+$, $CD200^+$ stem cells. In various embodiments, at least 10%, at least 20%, at least 30%, at least 40%, at least 50% at least 60%, at least 70%, at least 80%, at least 90%, or at least 95% of said isolated placental cells are $CD73^+$, $CD105^+$, $CD200^+$ stem cells. In a specific embodiment of said populations, said stem cells are $HLA-G^+$. In another specific embodiment, said stem cells are $CD34^-$, $CD38^-$ or $CD45^-$. In another specific embodiment, said stem cells are $CD34^-$, $CD38^-$ and $CD45^-$. In a more specific embodiment, said stem cells are $CD34^-$, $CD38^-$, $CD45^-$, and $HLA-G^+$. In other specific embodiments, said population has been expanded, for example, passaged at least once, at least three times, at least five times, at least 10 times, at least 15 times, or at least 20 times. In another specific embodiment, said population forms one or more embryoid-like bodies in culture under conditions that allow formation of embryoid-like bodies.

The invention also provides an isolated stem cell that is $CD200^+$ and $OCT-4^+$. In a specific embodiment, the stem cell is $CD73^+$ and $CD105^+$. In another specific embodiment, said stem cell is $HLA-G^+$. In another specific embodiment, said stem cell is $CD34^-$, $CD38^-$ or $CD45^-$. In another specific embodiment, said stem cell is $CD34^-$, $CD38^-$ and $CD45^-$. In a more specific embodiment, said stem cell is $CD34^-$, $CD38^-$, CD45⁻, CD73⁺, CD105⁺ and HLA-G⁺. In another specific embodiment, said stem cell facilitates the formation of one or more embryoid-like bodies from a population of isolated placental cells comprising placental stem cells when said population is cultured under conditions that allow formation of embryoid-like bodies.

In another embodiment, the invention provides a population of isolated cells comprising, e.g., that is enriched for, CD200⁺, OCT-4⁺ stem cells. In various embodiments, at least 10%, at least 20%, at least 30%, at least 40%, at least 50% at least 60%, at least 70%, at least 80%, at least 90%, or at least 95% of said isolated placental cells are CD200⁺, OCT-4⁺ stem cells. In a specific embodiment of the above populations, said stem cells are CD73⁺ and CD105⁺. In another specific embodiment, said stem cells are HLA-G⁺. In another specific embodiment, said stem cells are CD34⁻, CD38⁻ and CD45⁻. In a more specific embodiment, said stem cells are CD34⁻, CD38⁻, CD45⁻, CD73⁺, CD105⁺ and HLA-G⁺. In other specific embodiments, said population has been expanded, for example, has been passaged at least once, at least three times, at least five times, at least 10 times, at least 15 times, or at least 20 times. In another specific embodiment, said population forms one or more embryoid-like bodies when cultured under conditions that allow the formation of embryoid-like bodies.

In another embodiment, the invention provides an isolated stem cell that is CD73⁺ and CD105⁺ and which facilitates the formation of one or more embryoid-like bodies in a population of isolated placental cells comprising said stem cell when said population is cultured under conditions that allow formation of embryoid-like bodies. In a specific embodiment, said stem cell is CD34⁻, CD38⁻ or CD45⁻. In another specific embodiment, said stem cell is CD34⁻, CD38⁻ and CD45⁻. In another specific embodiment, said stem cell is OCT4⁺. In a more specific embodiment, said stem cell is OCT4+, CD34⁻, CD38⁻ and CD45⁻.

The invention further provides a population of isolated placental cells comprising, e.g., that is enriched for, CD73⁺, CD105⁺ stem cells, wherein said population forms one or more embryoid-like bodies under conditions that allow formation of embryoid-like bodies. In various embodiments, at least 10%, at least 20%, at least 30%, at least 40%, at least 50% at least 60%, at least 70%, at least 80%, at least 90%, or at least 95% of said isolated placental cells are CD73⁺, CD105⁺ stem cells. In a specific embodiment of the above populations, said stem cells are CD34⁻, CD38⁻ or CD45⁻. In another specific embodiment, said stem cells are CD34⁻, CD38⁻ and CD45⁻. In another specific embodiment, said stem cells are OCT-4⁺. In a more specific embodiment, said stem cells are OCT-4⁺, CD34⁻, CD38⁻ and CD45⁻. In other specific embodiments, said population has been expanded, for example, has been passaged at least once, at least three times, at least five times, at least 10 times, at least 15 times, or at least 20 times.

The invention further provides an isolated stem cell that is CD73⁺, CD105⁺ and HLA-G⁺. In a specific embodiment, said stem cell is CD34⁻, CD38⁻ or CD45⁻. In another specific embodiment, said stem cell is CD34⁻, CD38⁻ and CD45⁻. In another specific embodiment, said stem cell is OCT-4⁺. In another specific embodiment, said stem cell is CD200⁺. In a more specific embodiment, said stem cell is CD34⁻, CD38⁻, CD45⁻, OCT-4⁺ and CD200⁺. In another specific embodiment, said stem cell facilitates the formation of one or more embryoid-like bodies from a population of isolated placental cells comprising placental stem cells in culture under conditions that allow formation of embryoid-like bodies.

The invention further provides a population of isolated placental cells comprising, e.g., that is enriched for, CD73⁺, CD105⁺ and HLA-G⁺ stem cells. In various embodiments, at least 10%, at least 20%, at least 30%, at least 40%, at least 50% at least 60%, at least 70%, at least 80%, at least 90%, or at least 95% of said isolated placental cells are CD73⁺, CD105⁺ and HLA-G⁺ stem cells. In a specific embodiment of the above populations, said stem cells are CD34⁻, CD38⁻ or CD45⁻. In another specific embodiment, said stem cells are CD34⁻, CD38⁻ and CD45⁻. In another specific embodiment, said stem cells are OCT-4⁺. In another specific embodiment, said stem cells are CD200⁺. In a more specific embodiment, said stem cells are CD34⁻, CD38⁻, CD45⁻, OCT-4⁺ and CD200⁺. In another specific embodiment, said population has been expanded, for example, has been passaged at least once, at least three times, at least five times, at least 10 times, at least 15 times, or at least 20 times. In another specific embodiment, said population forms embryoid-like bodies when cultured under conditions that allow the formation of embryoid-like bodies.

The invention further provides an isolated stem cell that is OCT-4⁺ and which facilitates formation of one or more embryoid-like bodies in a population of isolated placental cells comprising said stem cell when cultured under conditions that allow formation of embryoid-like bodies. In a specific embodiment, said stem cell is CD73⁺ and CD105⁺. In another specific embodiment, said stem cell is CD34⁻, CD38⁻, or CD45⁻. In another specific embodiment, said stem cell is CD200⁺. In a more specific embodiment, said stem cell is CD73⁺, CD105⁺, CD200⁺, CD34⁻, CD38⁻, and CD45⁻.

The invention also provides a population of isolated cells comprising, e.g., that is enriched for, OCT-4⁺ placental stem cells, wherein said population forms one or more embryoid-like bodies when cultured under conditions that allow the formation of embryoid-like bodies. In various embodiments, at least 10%, at least 20%, at least 30%, at least 40%, at least 50% at least 60%, at least 70%, at least 80%, at least 90%, or at least 95% of said isolated placental cells are OCT4⁺ placental stem cells. In a specific embodiment of the above populations, said stem cells are CD73⁺ and CD105⁺. In another specific embodiment, said stem cells are CD34⁻, CD38⁻, or CD45⁻. In another specific embodiment, said stem cells are CD200⁺. In a more specific embodiment, said stem cells are CD73⁺, CD105⁺, CD200⁺, CD34⁻, CD38⁻, and CD45⁻. In another specific embodiment, said population has been expanded, for example, passaged at least once, at least three times, at least five times, at least 10 times, at least 15 times, or at least 20 times.

The invention further provides an isolated population of the placental stem cells described herein that is produced according to a method comprising perfusing a mammalian placenta that has been drained of cord blood and perfused to remove residual blood; perfusing said placenta with a perfusion solution; and collecting said perfusion solution, wherein said perfusion solution after perfusion comprises a population of placental cells that comprises placental stem cells; and isolating a plurality of said placental stem cells from said population of cells. In a specific embodiment, the perfusion solution is passed through both the umbilical vein and umbilical arteries and collected after it exudes from the placenta. In another specific embodiment, the perfusion solution is passed through the umbilical vein and collected from the umbilical arteries, or passed through the umbilical arteries and collected from the umbilical vein.

The invention further provides an isolated population of the placental stem cells described herein that is produced according to a method comprising digesting placental tissue with a tissue-disrupting enzyme to obtain a population of placental cells comprising placental stem cells, and isolating a plurality of placental stem cells from the remainder of said placental cells. In specific embodiments, said placental tissue is a whole placenta, an amniotic membrane, chorion, a combination of amnion and chorion, or a combination of any of the foregoing. In other specific embodiment, the tissue-disrupting enzyme is trypsin or collagenase.

In more specific embodiments, the invention provides any of the isolated stem cells above, wherein said stem cell expresses one or more genes at a detectably higher level than a bone marrow-derived mesenchymal stem cell, wherein said one or more genes are selected from the group consisting of ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PJP2, RTN1, SERPINB9, ST3GAL6, ST6GALNAC5, SLC12A8, TCF21, TGFB2, VTN, and ZC3H12A, and wherein said bone marrow derived stem cell has undergone a number of passages in culture equivalent to the number of passages said placental stem cell has undergone. Sequences corresponding to these genes are found on Affymetrix GENECHIP® arrays. These genes can also be found at GenBank accession nos. NM_001615 (ACTG2), BC065545 (ADARB1), (NM_181847 (AMIGO2), AY358590 (ARTS-1), BC074884 (B4GALT6), BC008396 (BCHE), BC020196 (C11orf9), BC031103 (CD200), NM_001845 (COL4A1), NM_001846 (COL4A2), BC052289 (CPA4), BC094758 (DMD), AF293359 (DSC3), NM_001943 (DSG2), AF338241 (ELOVL2), AY336105 (F2RL1), NM_018215 (FLJ10781), AY416799 (GATA6), BC075798 (GPR126), NM_016235 (GPRC5B), AF340038 (ICAM1), BC000844 (IER3), BC066339 (IGFBP7), BC013142 (IL1A), BT019749 (IL6), BC007461 (IL18), (BC072017) KRT18, BC075839 (KRT8), BC060825 (LIPG), BC065240 (LRAP), BC010444 (MATN2), BC011908 (MEST), BC068455 (NFE2L3), NM_014840 (NUAK1), AB006755 (PCDH7), NM_014476 (PDLIM3), BC126199 (PKP-2), BC090862 (RTN1), BC002538 (SERPINB9), BC023312 (ST3GAL6), BC001201 (ST6GALNAC5), BC126160 or BC065328 (SLC12A8), BC025697 (TCF21), BC096235 (TGFB2), BC005046 (VTN), and BC005001 (ZC3H12A) as of December 2006.

In a more specific embodiment, said stem cell expresses ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A at a detectably higher level than a bone marrow-derived mesenchymal stem cell.

In more specific embodiments, the invention also provides any of the populations of isolated stem cells above, wherein said stem cells express one or more genes at a detectably higher level than a population of bone marrow-derived mesenchymal stem cells, wherein said one or more genes are selected from the group consisting of ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A, and wherein said population of bone marrow derived stem cells has undergone a number of passages in culture equivalent to the number of passages said placental stem cell has undergone, and wherein said population of bone marrow-derived mesenchymal stem cells has a number of cells equivalent to said population of isolated stem cells. In a more specific embodiment, the population of isolated stem cells expresses ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A at a detectably higher level than said population of isolated bone marrow-derived mesenchymal stem cells.

In more specific embodiments of methods of selecting cell populations, the invention also provides methods of selecting one of the above-mentioned cell populations, comprising selecting cells that express one or more genes at a detectably higher level than a bone marrow-derived mesenchymal stem cell, wherein said one or more genes are selected from the group consisting of ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A, and wherein said bone marrow derived stem cell has undergone a number of passages in culture equivalent to the number of passages said placental stem cell has undergone. In a more specific embodiment, said selecting comprises selecting cells that express ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN and ZC3H12A at a detectably higher level than a bone marrow-derived mesenchymal stem cell.

The invention also provides compositions that comprise one or more of the stem cells of the invention, wherein the stem cell has been isolated from the placenta. Thus, the invention further provides a composition comprising a stem cell, wherein said stem cell is CD200$^+$ and HLA-G$^+$. In a specific embodiment, said stem cell is CD73$^+$ and CD105$^+$. In another specific embodiment, said stem cell is CD34$^-$, CD38$^-$ or CD45$^-$. In another specific embodiment, said stem cell is CD34$^-$, CD38$^-$ and CD45$^-$. In a more specific embodiment, said stem cell is CD34$^-$, CD38$^-$, CD45$^-$, CD73$^+$, CD105$^+$, CD200$^+$ and HLA-G$^+$.

In another embodiment, the invention provides a composition comprising a stem cell, wherein said stem cell is CD73$^+$, CD105$^+$ and CD200$^+$. In a specific embodiment, said stem cell is HLA-G$^+$. In another specific embodiment, said stem cell is CD34$^-$, CD38$^-$ or CD45$^-$. In another specific embodiment, said stem cell is CD34$^-$, CD38$^-$ and CD45$^-$. In another specific embodiment, said stem cell is CD34$^-$, CD38$^-$, CD45$^-$, and HLA-G$^+$.

In another embodiment, the invention provides a composition comprising a stem cell, wherein said stem cell is CD200$^+$ and OCT-4$^+$. In a specific embodiment, said stem cell is CD73$^+$ and CD105$^+$. In another specific embodiment, said stem cell is HLA-G$^+$. In another specific embodiment, said stem cell is CD34$^-$, CD38$^-$ or CD45$^-$. In another specific embodiment, said stem cell is CD34$^-$, CD38$^-$ and CD45$^-$. In another specific embodiment, said stem cell is CD34$^-$, CD38$^-$, CD45$^-$, CD73$^+$, CD105$^+$, and HLA-G$^+$.

In another embodiment, the invention provides a composition comprising a stem cell that is CD73$^+$ and CD105$^+$, wherein said stem cell facilitates formation of an embryoid-like body in a population of isolated placental cells comprising said stem cell under conditions that allow the formation of an embryoid-like body. In a specific embodiment, said stem cell is CD34$^-$, CD38$^-$ or CD45$^-$. In another specific embodiment, said stem cell is OCT-4$^+$. In another specific embodiment, said stem cell is CD200$^+$. In another specific embodiment, said stem cell is OCT-4+, CD200$^+$, CD34$^-$, CD38$^-$ and CD45$^-$.

In yet another embodiment, the invention provides a composition comprising a stem cell that is CD73$^+$, CD105$^+$ and HLA-G$^+$. In a specific embodiment, said stem cell is CD34$^-$, CD38$^-$ or CD45$^-$. In another specific embodiment, said stem cell is OCT-4$^+$. In another specific embodiment, said stem cell is CD200$^+$. In another specific embodiment, said stem cell is OCT-4+, CD200$^+$, CD34$^-$, CD38$^-$ and CD45$^-$.

In another embodiment, the invention provides a composition comprising a stem cell that is OCT-4$^+$, wherein said stem cell facilitates formation of an embryoid-like body in a population of isolated placental cells comprising said stem cell under conditions that allow the formation of an embryoid-like body. In a specific embodiment, said stem cell is CD73$^+$ and CD105$^+$. In another specific embodiment, said stem cell is CD34$^-$, CD38$^-$ and CD45$^-$. In another specific embodiment, said stem cell is CD200$^+$. In another specific embodiment, said stem cell is CD73$^+$, CD105$^+$, CD200$^+$, CD34$^-$, CD38$^-$ and CD45$^-$.

In more specific embodiments of the above compositions, said stem cell expresses one or more genes at a detectably higher level than a bone marrow-derived mesenchymal stem cell, wherein said one or more genes are selected from the group consisting of ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A, and wherein said bone marrow derived stem cell has undergone a number of passages in culture equivalent to the number of passages said placental stem cell has undergone. In a more specific embodiment of the above compositions, said stem cells express ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A at a detectably higher level than a population of isolated bone marrow-derived mesenchymal stem cell, wherein said population of stem cells and said population of bone marrow-derived mesenchymal cells have equivalent numbers of cells.

In another specific embodiment, any of the foregoing compositions comprises a matrix. In a more specific embodiment, said matrix is a three-dimensional scaffold. In another more specific embodiment, said matrix comprises collagen, gelatin, laminin, fibronectin, pectin, ornithine, or vitronectin. In another more specific embodiment, the matrix is an amniotic membrane or an amniotic membrane-derived biomaterial. In another more specific embodiment, said matrix comprises an extracellular membrane protein. In another more specific embodiment, said matrix comprises a synthetic compound. In another more specific embodiment, said matrix comprises a bioactive compound. In another more specific embodiment, said bioactive compound is a growth factor, cytokine, antibody, or organic molecule of less than 5,000 daltons.

In another embodiment, the invention further provides a composition comprising medium conditioned by any of the foregoing stem cells, or any of the foregoing stem cell populations. In a specific embodiment, any such composition comprises a stem cell that is not derived from a placenta. In a more specific embodiment, said stem cell is an embryonic stem cell. In another more specific embodiment, said stem cell is a mesenchymal stem cell. In another more specific embodiment, said stem cell is a bone marrow-derived stem cell. In another more specific embodiment, said stem cell is a hematopoietic progenitor cell. In another more specific embodiment, said stem cell is a somatic stem cell. In an even more specific embodiment, said somatic stem cell is a neural stem cell, a hepatic stem cell, a pancreatic stem cell, an endothelial stem cell, a cardiac stem cell, or a muscle stem cell.

The invention also provides methods for producing populations of stem cells derived from mammalian placenta. In one embodiment, for example, the invention provides a method of producing a cell population comprising selecting cells that (a) adhere to a substrate, and (b) express CD200 and HLA-G; and isolating said cells from other cells to form a cell population. In another embodiment, the invention provides a method of producing a cell population, comprising selecting cells that (a) adhere to a substrate, and (b) express CD73, CD105, and CD200; and isolating said cells from other cells to form a cell population. In another embodiment, the invention provides a method of producing a cell population, comprising selecting cells that (a) adhere to a substrate and (b) express CD200 and OCT-4; and isolating said cells from other cells to form a cell population. In yet another embodiment, the invention provides a method of producing a cell population, comprising selecting cells that (a) adhere to a substrate, (b) express CD73 and CD105, and (c) facilitate the formation of one or more embryoid-like bodies when cultured with a population of placental cells under conditions that allow for the formation of embryoid-like bodies; and isolating said cells from other cells to form a cell population. In another embodiment, the invention provides a method of producing a cell population, comprising selecting cells that (a) adhere to a substrate, and (b) express CD73, CD105 and HLA-G; and isolating said cells from other cells to form a cell population. The invention also provides a method of producing a cell population, comprising selecting cells that (a) adhere to a substrate, (b) express OCT-4, and (c) facilitate the formation of one or more embryoid-like bodies when cultured with a population of placental cells under conditions that allow for the formation of embryoid-like bodies; and isolating said cells from other cells to form a cell population. In a specific embodiment of any of the foregoing methods, said substrate comprises fibronectin. In another specific embodiment, the methods comprise selecting cells that express ABC-p. In another specific embodiment, the methods comprise selecting cells exhibiting at least one characteristic specific to a mesenchymal stem cell. In a more specific embodiment, said characteristic specific to a mesenchymal stem cell is expression of CD29, expression of CD44, expression of CD90, or expression of a combination of the foregoing. In another specific embodiment of the methods, said selecting is accomplished using an antibody. In another specific embodiment, said selecting is accomplished using flow cytometry. In another specific embodiment, said selecting is accomplished using magnetic beads. In another specific embodiment, said selecting is accomplished by fluorescence-activated cell sorting. In another specific embodiment of the above methods, said cell population is expanded.

The invention also provides a method of producing a stem cell line, comprising transforming a stem cell with a DNA sequence that encodes a growth-promoting protein; and exposing said stem cell to conditions that promote production of said growth-promoting protein. In a specific embodiment, said growth-promoting protein is v-myc, N-myc, c-myc, p53, SV40 large T antigen, polyoma large T antigen, E1a adenovirus or human papillomavirus E7 protein. In a more specific embodiment, said DNA sequence is regulatable. In more specific embodiment, said DNA sequence is regulatable by tetracycline. In another specific embodiment, said growth-promoting protein has a regulatable activity. In another specific embodiment, said growth-promoting protein is a temperature-sensitive mutant.

The invention further provides cryopreserved stem cell populations. For example, the invention provides a population of $CD200^+$, $HLA-G^+$ stem cells, wherein said cells have been cryopreserved, and wherein said population is contained within a container. The invention also provides a population of $CD73^+$, $CD105^+$, $CD200^+$ stem cells, wherein said stem cells have been cryopreserved, and wherein said population is contained within a container. The invention also provides a population of $CD200^+$, $OCT-4^+$ stem cells, wherein said stem cells have been cryopreserved, and wherein said population is contained within a container. The invention also provides a population of $CD73^+$, $CD105^+$ stem cells, wherein said cells have been cryopreserved, and wherein said population is contained within a container, and wherein said stem cells facilitate the formation of one or more embryoid-like bodies when cultured with a population of placental cells under conditions that allow for the formation of embryoid-like bodies. The invention further provides a population of $CD73^+$, $CD105^+$, $HLA-G^+$ stem cells, wherein said cells have been cryopreserved, and wherein said population is contained within a container. The invention also provides a population of $OCT-4^+$ stem cells, wherein said cells have been cryopreserved, wherein said population is contained within a container, and wherein said stem cells facilitate the formation of one or more embryoid-like bodies when cultured with a population of placental cells under conditions that allow for the formation of embryoid-like bodies. In a specific embodiment of any of the foregoing cryopreserved populations, said container is a bag. In various specific embodiments, said population comprises about, at least, or at most $1 \times 10^6$ said stem cells, $5 \times 10^6$ said stem cells, $1 \times 10^7$ said stem cells, $5 \times 10^7$ said stem cells, $1 \times 10^8$ said stem cells, $5 \times 10^8$ said stem cells, $1 \times 10^9$ said stem cells, $5 \times 10^9$ said stem cells, or $1 \times 10^{10}$ said stem cells. In other specific embodiments of any of the foregoing cryopreserved populations, said stem cells have been passaged about, at least, or no more than 5 times, no more than 10 times, no more than 15 times, or no more than 20 times. In another specific embodiment of any of the foregoing cryopreserved populations, said stem cells have been expanded within said container.

3.1 Definitions

As used herein, the term "SH2" refers to an antibody that binds an epitope on the marker CD105. Thus, cells that are referred to as $SH2^+$ are $CD105^+$.

As used herein, the terms "SH3" and "SH4" refer to antibodies that bind epitopes present on the marker CD73. Thus, cells that are referred to as $SH3^+$ and/or $SH4^+$ are $CD73^+$.

As used herein, the term "isolated stem cell" means a stem cell that is substantially separated from other, non-stem cells of the tissue, e.g., placenta, from which the stem cell is derived. A stem cell is "isolated" if at least 50%, 60%, 70%, 80%, 90%, 95%, or at least 99% of the non-stem cells with which the stem cell is naturally associated, or stem cells displaying a different marker profile, are removed from the stem cell, e.g., during collection and/or culture of the stem cell.

As used herein, the term "population of isolated cells" means a population of cells that is substantially separated from other cells of the tissue, e.g., placenta, from which the population of cells is derived. A stem cell is "isolated" if at least 50%, 60%, 70%, 80%, 90%, 95%, or at least 99% of the cells with which the population of cells, or cells from which the population of cells is derived, is naturally associated, i.e., stem cells displaying a different marker profile, are removed from the stem cell, e.g., during collection and/or culture of the stem cell.

As used herein, the term "placental stem cell" refers to a stem cell or progenitor cell that is derived from a mammalian placenta, regardless of morphology, cell surface markers, or the number of passages after a primary culture. The term "placental stem cell" as used herein does not, however, refer to a trophoblast. A cell is considered a "stem cell" if the cell retains at least one attribute of a stem cell, e.g., a marker or gene expression profile associated with one or more types of stem cells; the ability to replicate at least 10-40 times in culture, the ability to differentiate into cells of all three germ layers; the lack of adult (i.e., differentiated) cell characteristics, or the like. The terms "placental stem cell" and "placenta-derived stem cell" may be used interchangeably.

As used herein, a stem cell is "positive" for a particular marker when that marker is detectable above background. For example, a placental stem cell is positive for, e.g., CD73 because CD73 is detectable on placental stem cells in an amount detectably greater than background (in comparison to, e.g., an isotype control). A cell is also positive for a marker when that marker can be used to distinguish the cell from at least one other cell type, or can be used to select or isolate the cell when present or expressed by the cell. In the context of, e.g., antibody-mediated detection, "positive," as an indication a particular cell surface marker is present, means that the marker is detectable using an antibody, e.g., a fluorescently-labeled antibody, specific for that marker; "positive" also means that a cell bears that marker in a amount that produces a signal, e.g., in a cytometer, that is detectably above background. For example, a cell is "$CD200^+$" where the cell is detectably labeled with an antibody specific to CD200, and the signal from the antibody is detectably higher than a control (e.g., background). Conversely, "negative" in the same context means that the cell surface marker is not detectable using an antibody specific for that marker compared to background. For example, a cell is "$CD34^-$" where the cell is not detectably labeled with an antibody specific to CD34. Unless otherwise noted herein, cluster of differentiation ("CD") markers are detected using antibodies. OCT-4 is determined to be present, and a cell is "$OCT-4^+$" if OCT-4 is detectable using RT-PCR.

4. BRIEF DESCRIPTION OF THE FIGURES

FIG. 1: Viability of placental stem cells from perfusion (A), amnion (B), chorion (C), amnion-chorion plate (D) or umbilical cord (E). Numbers on X-axis designate placenta from which stem cells were obtained.

Figure 2:
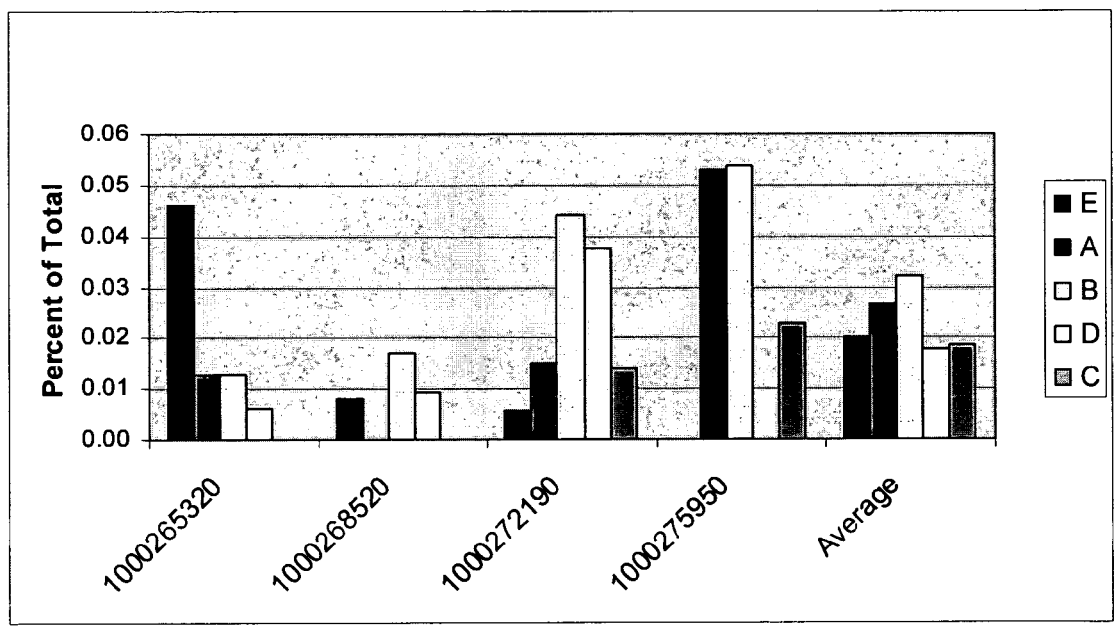

FIG. 2: Percent HLA ABC$^-$/CD45$^-$/CD34$^-$/CD133$^+$ cells from perfusion (A), amnion (B), chorion (C), amnion-chorion plate (D) or umbilical cord (E) as determined by FACSCalibur. Numbers on X-axis designate placenta from which stem cells were obtained.

Figure 3:
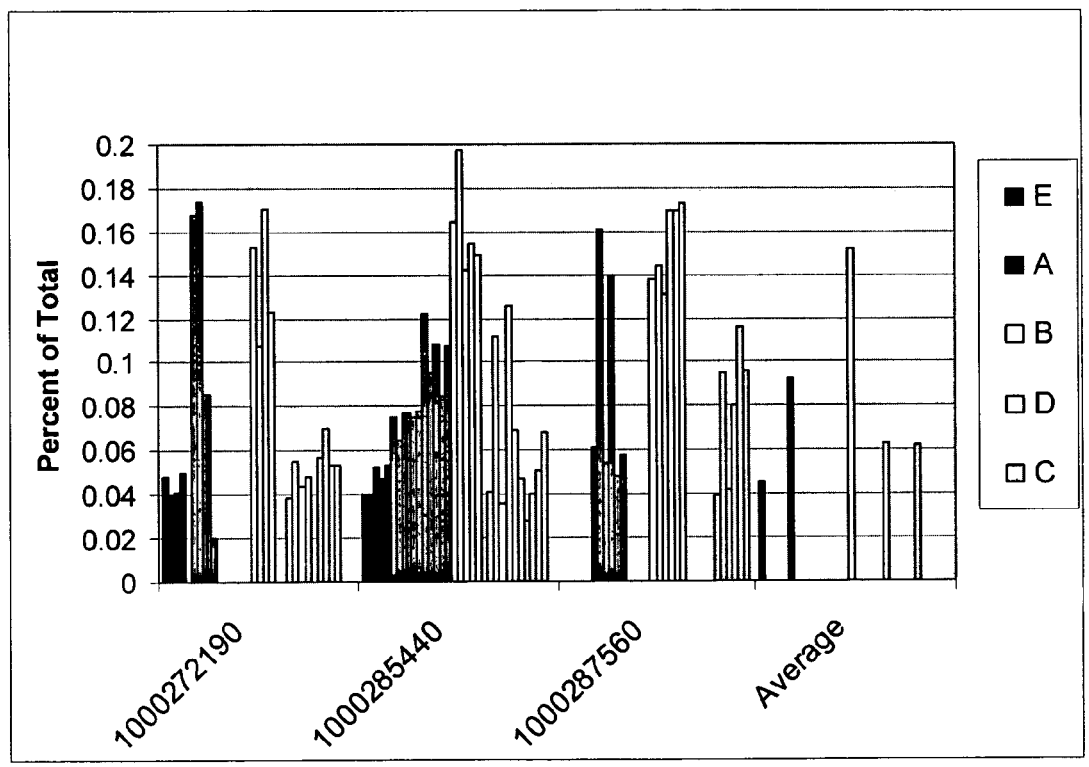

FIG. 3: Percent HLA ABC$^-$/CD45$^-$/CD34$^-$/CD133$^+$ cells from perfusion (A), amnion (B), chorion (C), amnion-chorion plate (D) or umbilical cord (E), as determined by FACS Aria. Numbers on X-axis designate placenta from which stem cells were obtained.

Figure 4:
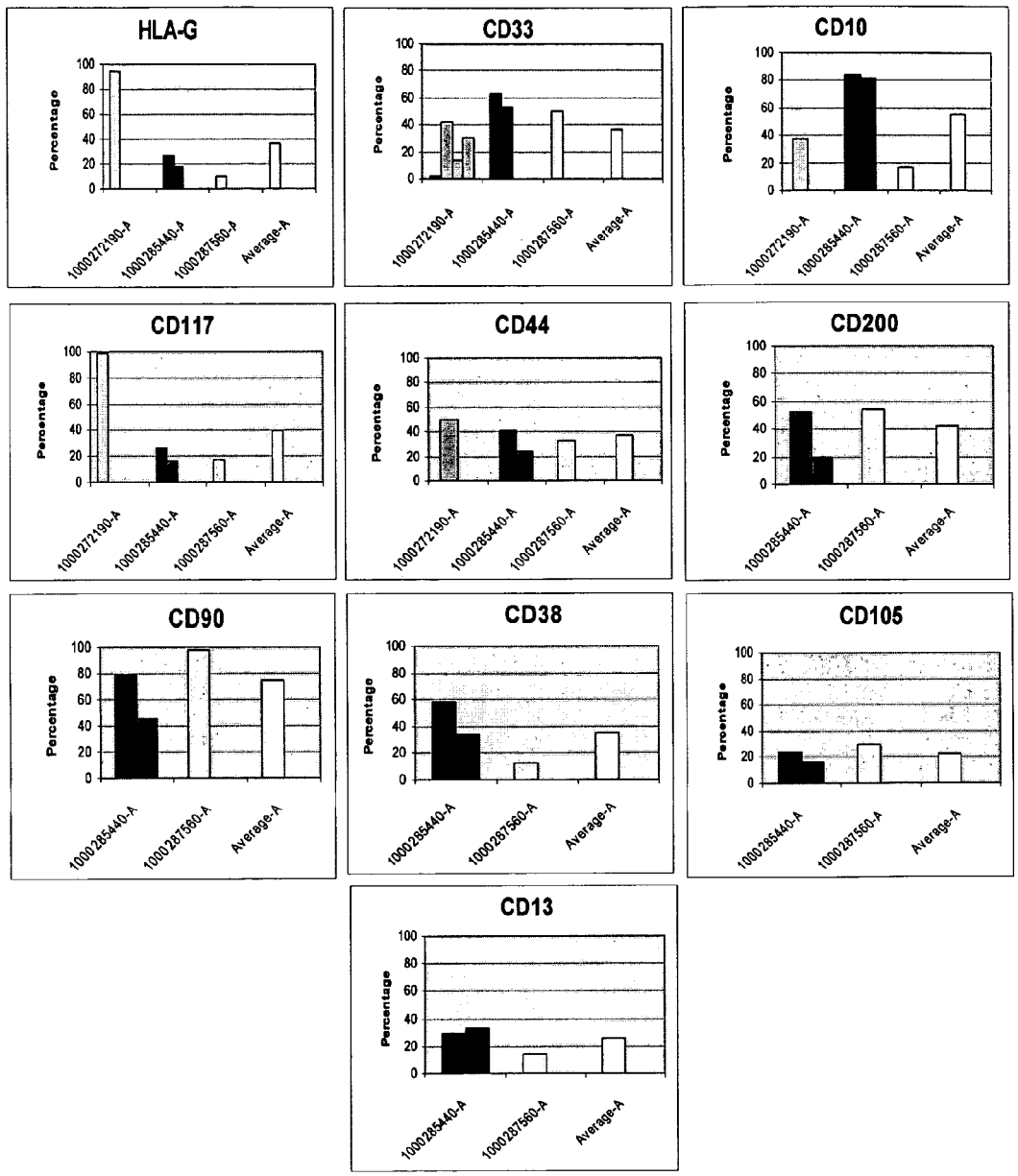

FIG. 4: HLA-G, CD10, CD13, CD33, CD38, CD44, CD90, CD105, CD117, CD200 expression in stem cells derived from placental perfusate.

Figure 5:
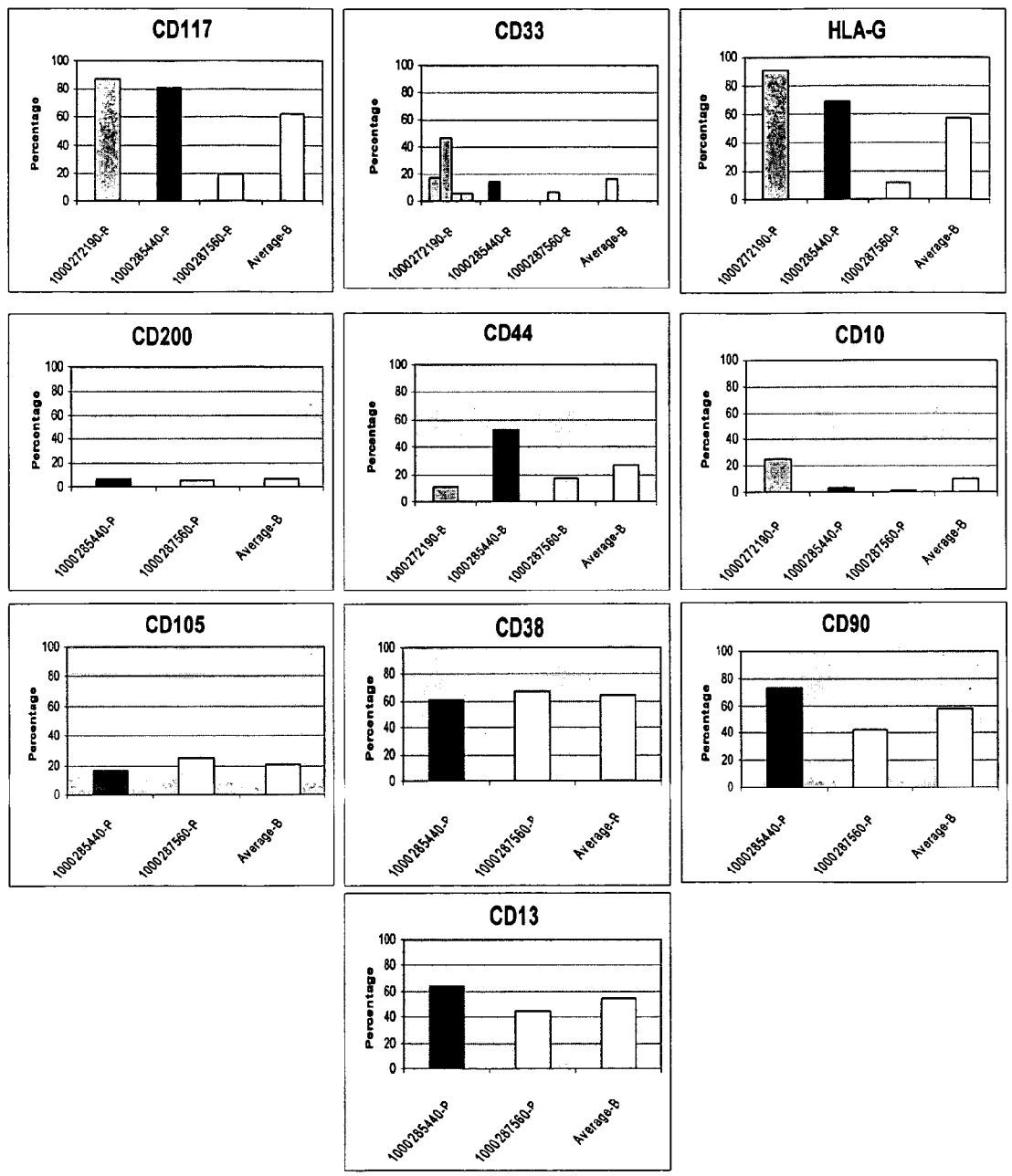

FIG. 5: HLA-G, CD10, CD13, CD33, CD38, CD44, CD90, CD105, CD117, CD200 expression in stem cells derived from amnion.

Figure 6:
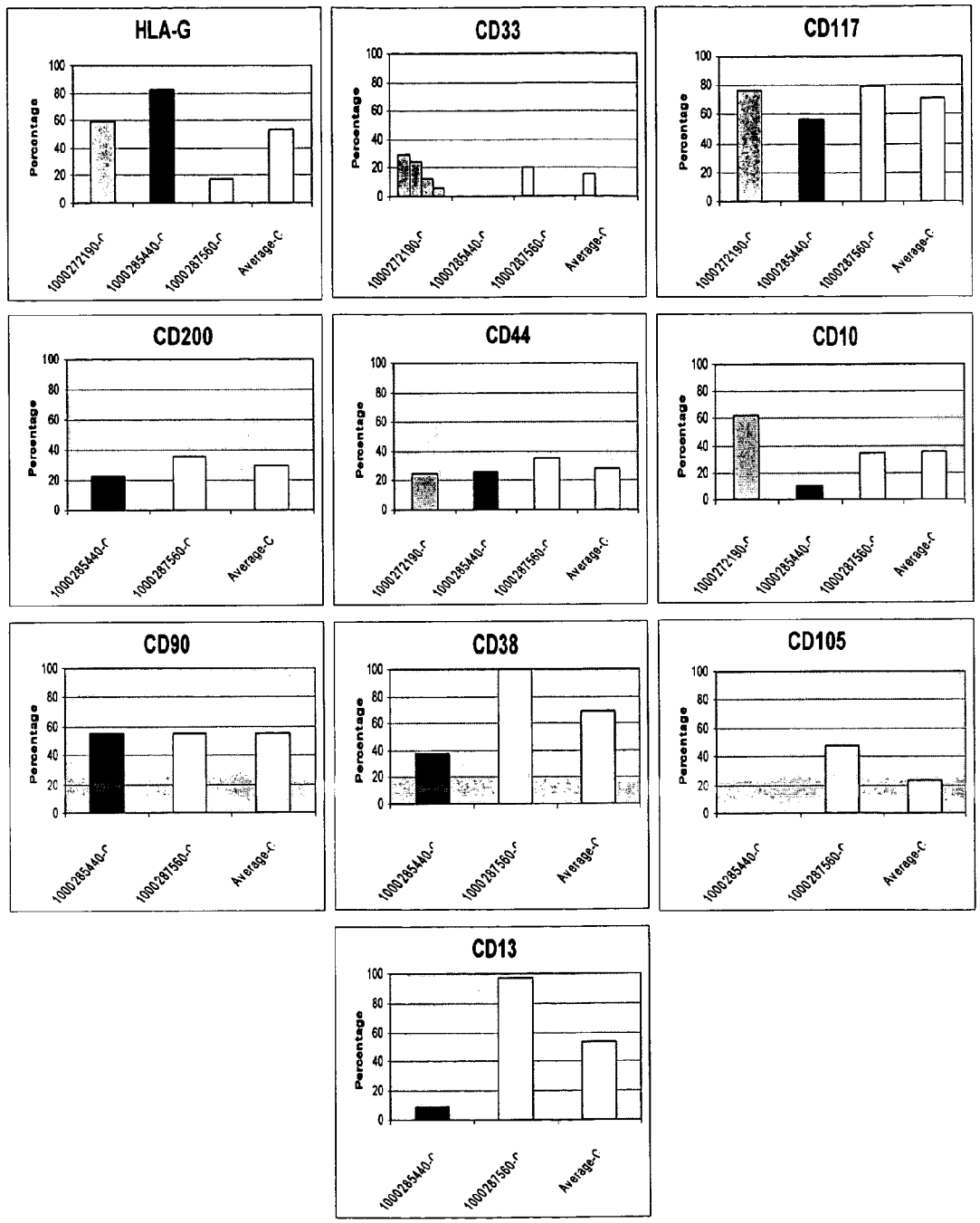

FIG. 6: HLA-G, CD10, CD13, CD33, CD38, CD44, CD90, CD105, CD117, CD200 expression in stem cells derived from chorion.

Figure 7:
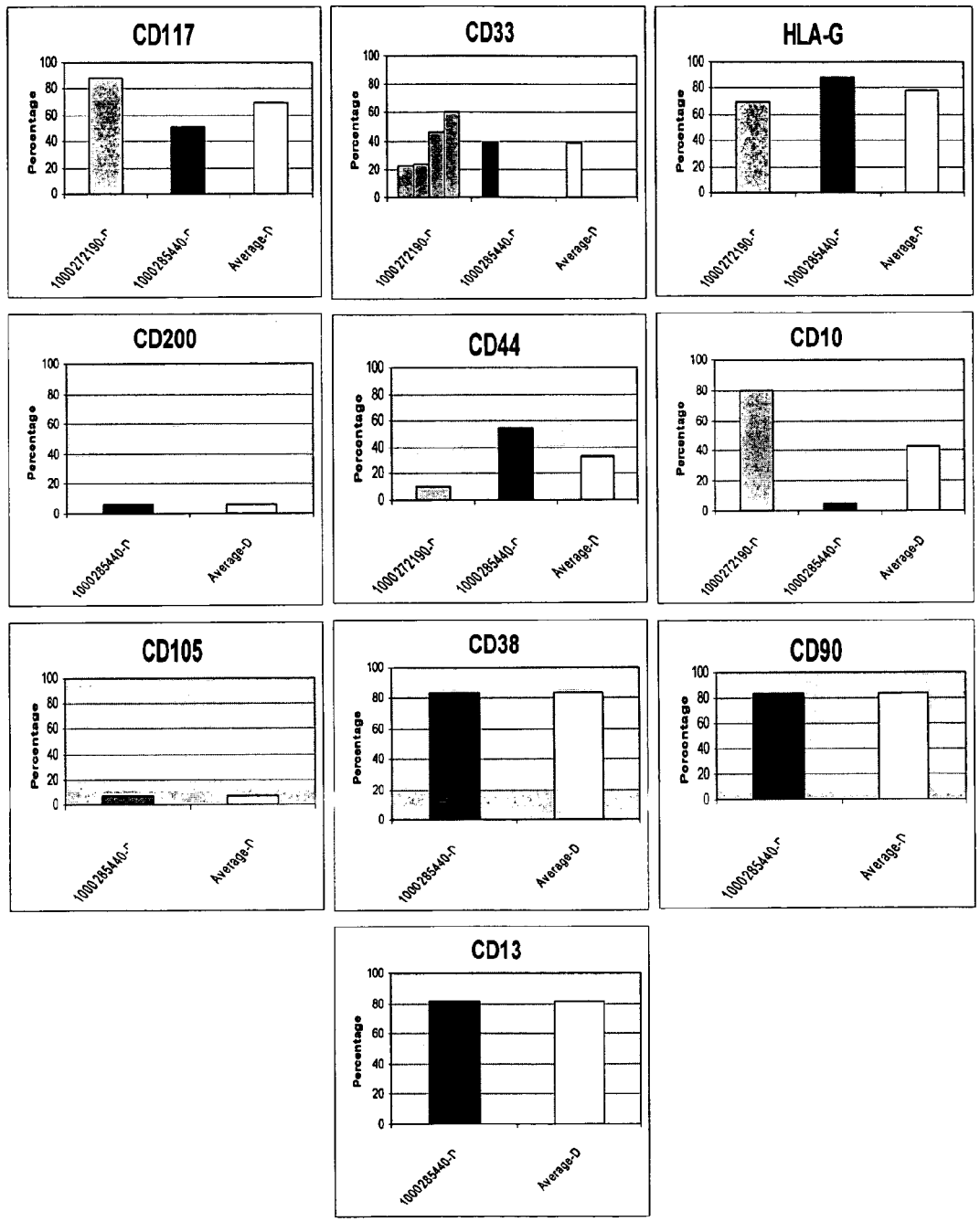

FIG. 7: HLA-G, CD10, CD13, CD33, CD38, CD44, CD90, CD105, CD117, CD200 expression in stem cells derived from amnion-chorion plate.

Figure 8:
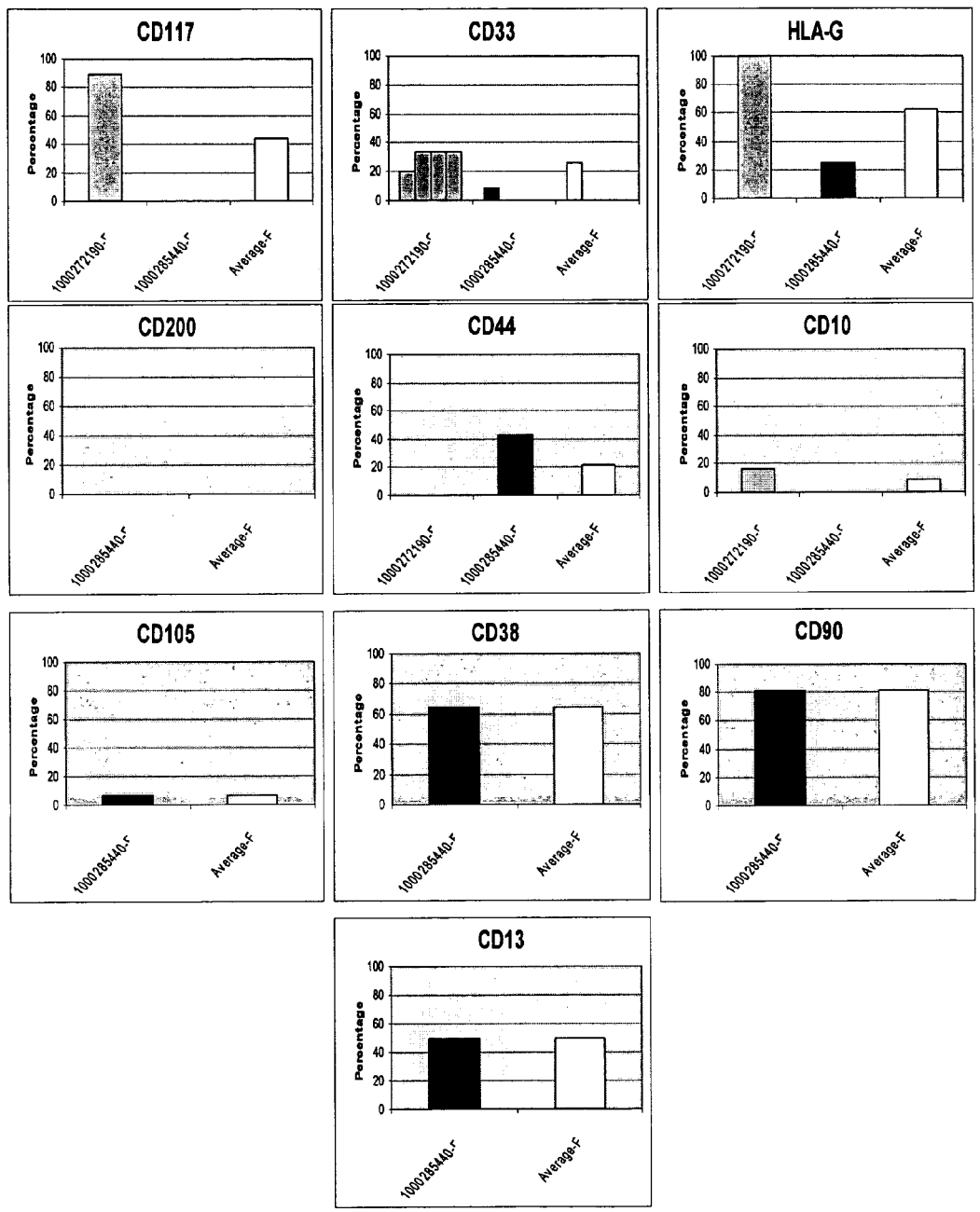

FIG. 8: HLA-G, CD10, CD13, CD33, CD38, CD44, CD90, CD105, CD117, CD200 expression in stem cells derived from umbilical cord.

Figure 9:
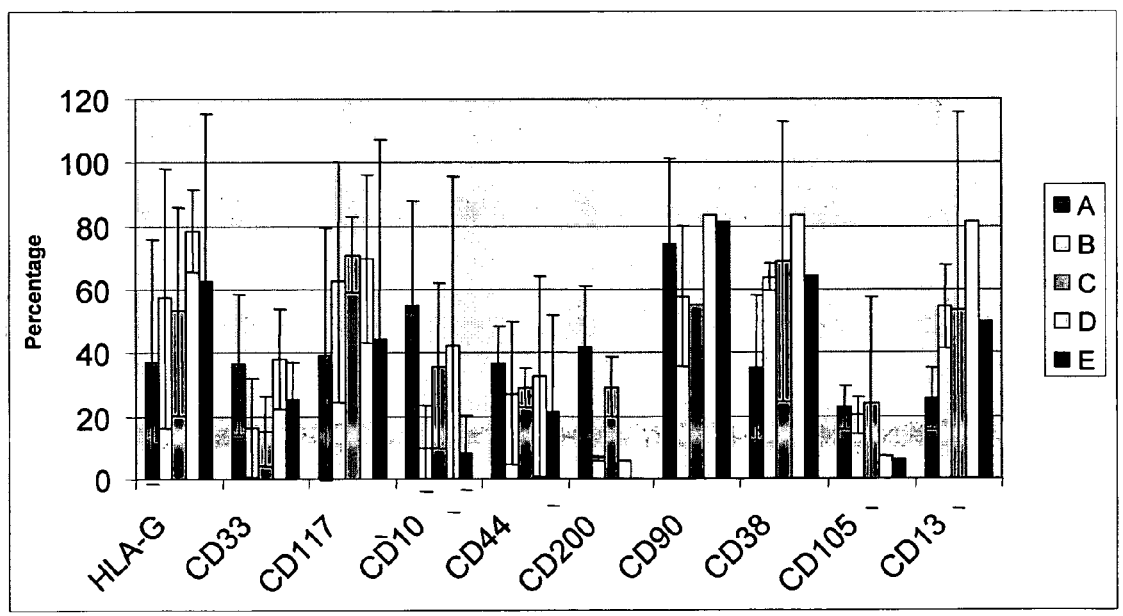

FIG. 9: Average expression of HLA-G, CD10, CD13, CD33, CD38, CD44, CD90, CD105, CD117, CD200 expression in stem cells derived from perfusion (A), amnion (B), chorion (C), amnion-chorion plate (D) or umbilical cord (E).

Figure 10:
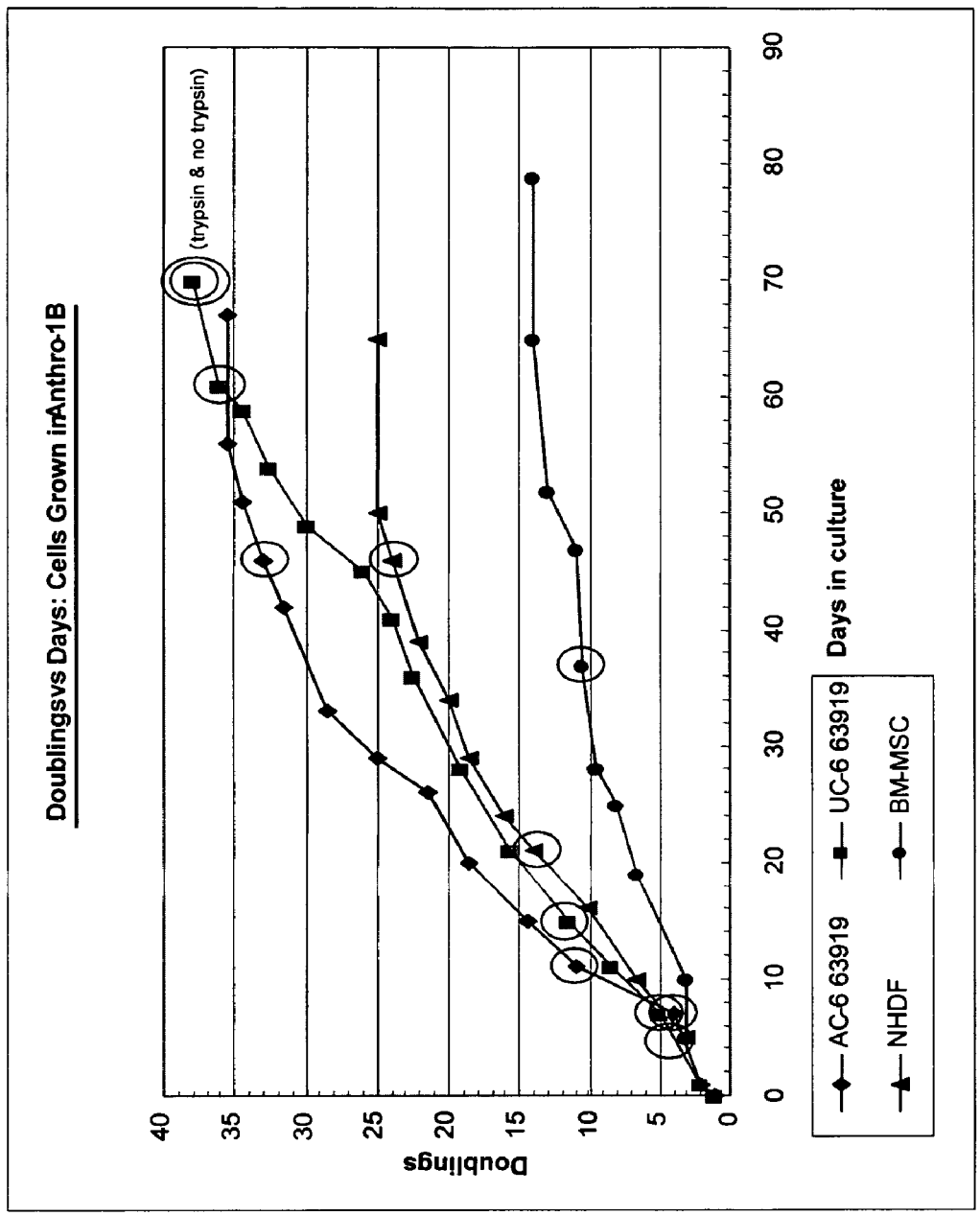

FIG. 10: Culture time courses for amnion/chorion (AC), umbilical cord (UC), bone marrow-derived stem cell (BM-MSC) and human dermal fibroblast (NHDF) cell lines used in this study. All cultures were grown and propagated using the same seeding and passage densities. Circles indicate which cultures were used for RNA isolation. Late cultures were harvested just prior to senescence. Two UC cultures were harvested at 38 doublings (UC-38) to compare the effect of trypsinization on gene expression. All other cultures were lysed directly in their culture flasks prior to RNA isolation.

Figure 11:
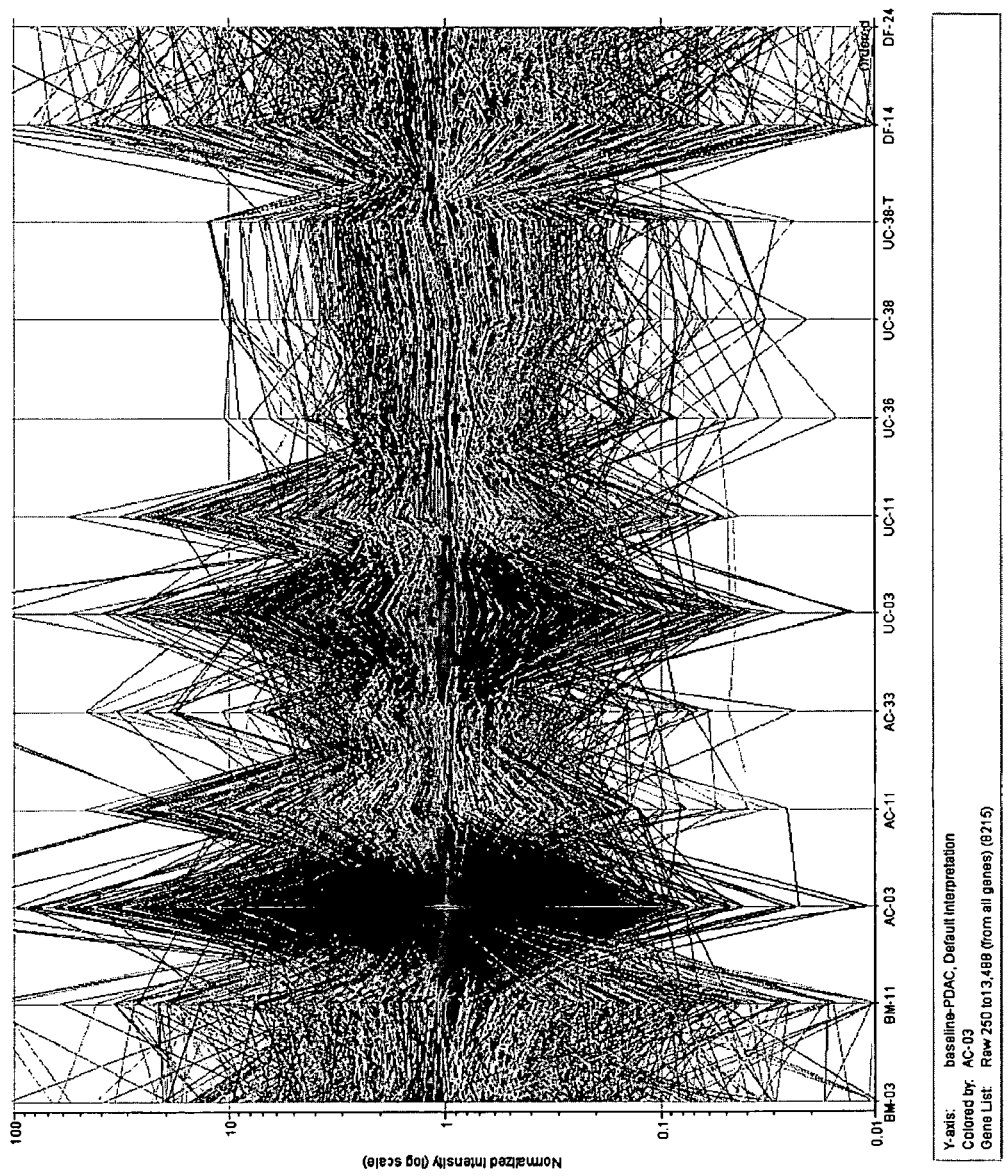

FIG. 11: Line plot of relative expression levels of 8215 genes in amnion/chorion (AC), umbilical cord (UC), bone marrow-derived stem cell (BM-MSC) and human dermal fibroblast (DF) cells. The number associated with each cell line designation on the X-axis indicates the number of days the cell line was cultured prior to evaluation of gene expression levels. The chart was generated from RNA expression data analyzed by GeneSpring software. AC-03 was used as the selected condition.

Figure 12:
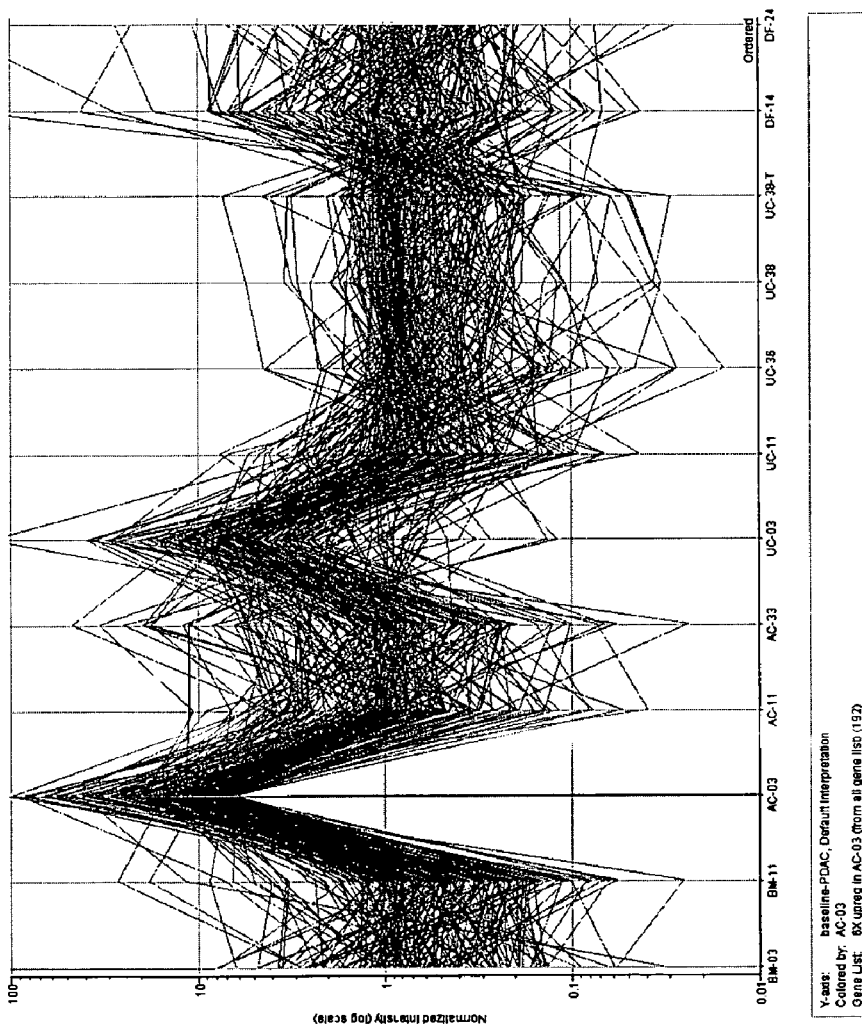

FIG. 12: Subset of the all genes list showing genes overexpressed ≧6-fold in AC-03 for amnion/chorion (AC), umbilical cord (UC), bone marrow-derived stem cell (BM-MSC) and human dermal fibroblast (DF) cells. The number associated with each cell line designation on the X-axis indicates the number of days the cell line was cultured prior to evaluation of gene expression levels. The chart was generated from RNA expression data analyzed by GeneSpring software. AC-03 was used as the selected condition.

Figure 13:
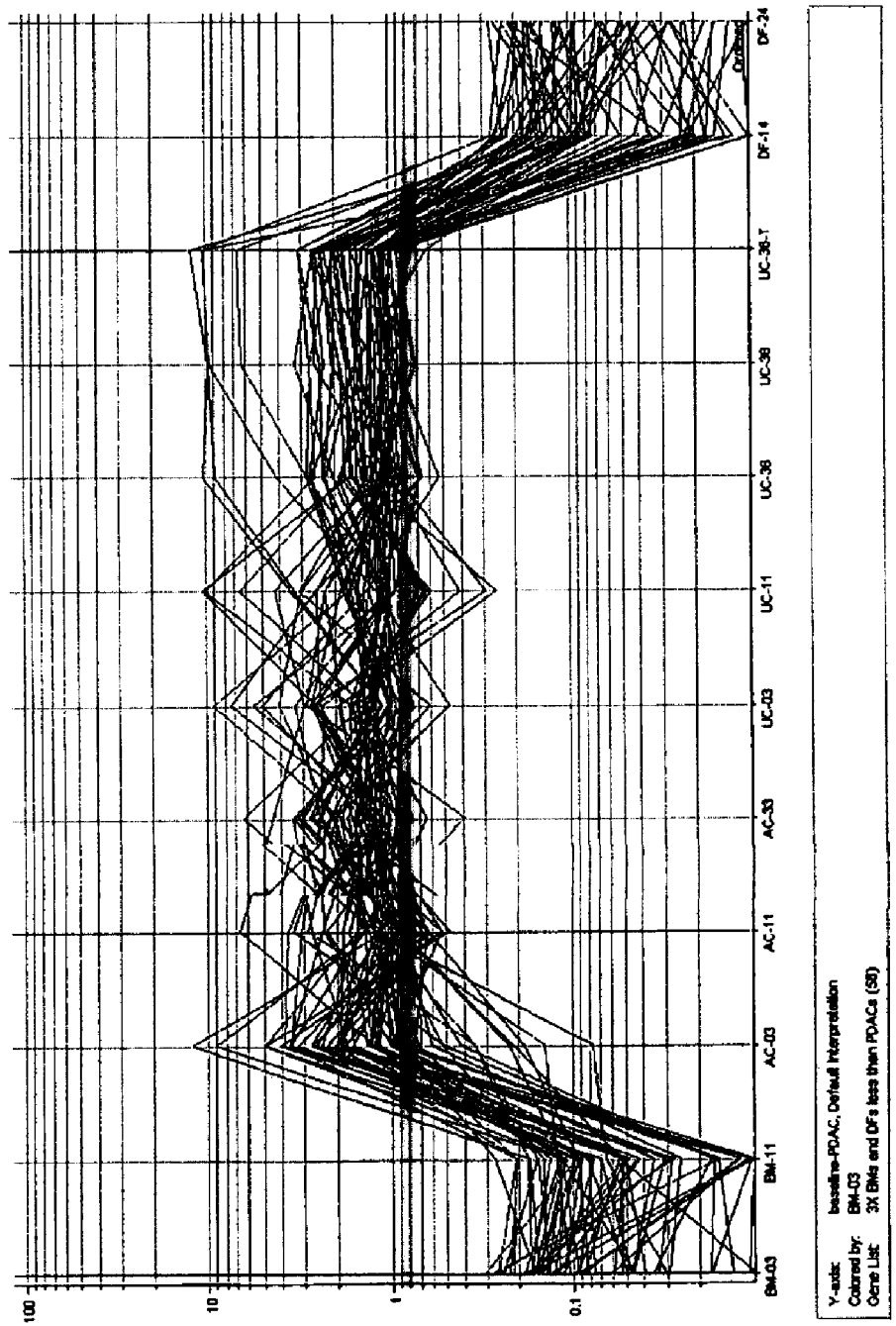

FIG. 13: Placental stem cell-specific or umbilical cord stem cell-specific genes found by fold change filtering for amnion/chorion (AC), umbilical cord (UC), bone marrow-derived stem cell (BM-MSC) and human dermal fibroblast (DF) cells. The number associated with each cell line designation on the X-axis indicates the number of days the cell line was cultured prior to evaluation of gene expression levels. The chart was generated from RNA expression data analyzed by GeneSpring software. AC-03 was used as the selected condition.

5. DETAILED DESCRIPTION OF THE INVENTION

5.1 Placental Stem Cells and Placental Stem Cell Populations

Placental stem cells are stem cells, obtainable from a placenta or part thereof, that adhere to a tissue culture substrate and have the capacity to differentiate into non-placental cell types. Placental stem cells can be either fetal or maternal in origin (that is, can have the genotype of either the fetus or mother, respectively). Preferably, the placental stem cells and placental stem cell populations of the invention are fetal in origin. Populations of placental stem cells, or populations of cells comprising placental stem cells, can comprise placental stem cells that are solely fetal or maternal in origin, or can comprise a mixed population of placental stem cells of both fetal and maternal origin. The placental stem cells, and populations of cells comprising the placental stem cells, can be identified and selected by the morphological, marker, and culture characteristic discussed below.

5.1.1 Physical and Morphological Characteristics

The placental stem cells of the present invention, when cultured in primary cultures or in cell culture, adhere to the tissue culture substrate, e.g., tissue culture container surface (e.g., tissue culture plastic). Placental stem cells in culture assume a generally fibroblastoid, stellate appearance, with a number of cytoplasmic processes extending from the central cell body. The placental stem cells are, however, morphologically differentiable from fibroblasts cultured under the same conditions, as the placental stem cells exhibit a greater number of such processes than do fibroblasts. Morphologically, placental stem cells are also differentiable from hematopoietic stem cells, which generally assume a more rounded, or cobblestone, morphology in culture.

5.1.2 Cell Surface Molecular and Genetic Markers

Placental stem cells of the present invention, and populations of placental stem cells, express a plurality of markers that can be used to identify and/or isolate the stem cells, or populations of cells that comprise the stem cells. The placental stem cells, and stem cell populations of the invention (that is, two or more placental stem cells) include stem cells and stem cell-containing cell populations obtained directly from the placenta, or any part thereof (e.g., amnion, chorion, placental cotyledons, and the like). Placental stem cell populations also includes populations of (that is, two or more) placental stem cells in culture, and a population in a container, e.g., a bag. Placental stem cells are not, however, trophoblasts.

The placental stem cells of the invention generally express the markers CD73, CD105, CD200, HLA-G, and/or OCT-4, and do not express CD34, CD38, or CD45. Placental stem cells can also express HLA-ABC (MHC-1) and HLA-DR. These markers can be used to identify placental stem cells, and to distinguish placental stem cells from other stem cell types. Because the placental stem cells can express CD73 and CD105, they can have mesenchymal stem cell-like characteristics. However, because the placental stem cells can express CD200 and HLA-G, a fetal-specific marker, they can be distinguished from mesenchymal stem cells, e.g., bone marrow-derived mesenchymal stem cells, which express neither CD200 nor HLA-G. In the same manner, the lack of expression of CD34, CD38 and/or CD45 identifies the placental stem cells as non-hematopoietic stem cells.

Thus, in one embodiment, the invention provides an isolated stem cell that is $CD200^+$ or $HLA-G^+$. In a specific embodiment, said stem cell is a placental stem cell. In a specific embodiment, the stem cell is $CD200^+$ and $HLA-G^+$. In a specific embodiment, said stem cell is $CD73^+$ and $CD105^+$. In another specific embodiment, said stem cell is $CD34^-$, $CD38^-$ or $CD45^-$. In another specific embodiment, said stem cell is $CD34^-$, $CD38^-$ and $CD45^-$. In another specific embodiment, said stem cell is $CD34^-$, $CD38^-$, $CD45^-$, $CD73^+$ and $CD105^+$. In another specific embodiment, said $CD200^+$ or $HLA-G^+$ stem cell facilitates the formation of embryoid-like bodies in a population of placental cells comprising the stem cells, under conditions that allow the formation of embryoid-like bodies. In another specific embodiment, said placental stem cell is isolated away from placental cells that are not stem cells. In another specific embodiment, said placental stem cell is isolated away from placental stem cells that do not display these markers.

In another embodiment, the invention also provides a method of selecting a placental stem cell from a plurality of placental cells, comprising selecting a $CD200^+$ or $HLA-G^+$ placental cell, whereby said cell is a placental stem cell. In a specific embodiment, said selecting comprises selecting a placental cell that is both $CD200^+$ and $HLA-G^+$. In a specific embodiment, said selecting comprises selecting a placental cell that is also $CD73^+$ and $CD105^+$. In another specific embodiment, said selecting comprises selecting a placental cell that is also $CD34^-$, $CD38^-$ or $CD45^-$. In another specific embodiment, said selecting comprises selecting a placental cell that is also $CD34^-$, $CD38^-$ and $CD45^-$. In another specific embodiment, said selecting comprises selecting a placental cell that is also $CD34^-$, $CD38^-$, $CD45^-$, $CD73^+$ and $CD105^+$. In another specific embodiment, said selecting comprises selecting a placental cell that also facilitates the formation of embryoid-like bodies in a population of placental cells comprising the stem cells, under conditions that allow the formation of embryoid-like bodies.

In another embodiment, the invention provides an isolated population of cells comprising, e.g., that is enriched for, $CD200^+$, $HLA-G^+$ stem cells. In a specific embodiment, said population is a population of placental cells. In various embodiments, at least about 10%, at least about 20%, at least about 30%, at least about 40%, at least about 50%, or at least about 60% of said cells are $CD200^+$, $HLA-G^+$ stem cells. Preferably, at least about 70% of said cells are $CD200^+$, $HLA-G^+$ stem cells. More preferably, at least about 90%, 95%, or 99% of said cells are $CD200^+$, $HLA-G^+$ stem cells. In a specific embodiment of the isolated populations, said stem cells are also $CD73^+$ and $CD105^+$. In another specific embodiment, said stem cells are also $CD34^-$, $CD38^-$ or $CD45^-$. In a more specific embodiment, said stem cells are also $CD34^-$, $CD38^-$, $CD45^-$, $CD73^+$ and $CD105^+$. In another embodiment, said isolated population produces one or more embryoid-like bodies when cultured under conditions that allow the formation of embryoid-like bodies. In another specific embodiment, said population of placental stem cells is isolated away from placental cells that are not stem cells. In another specific embodiment, said population of placental stem cells is isolated away from placental stem cells that do not display these markers.

In another embodiment, the invention also provides a method of selecting a placental stem cell population from a plurality of placental cells, comprising selecting a population of placental cells wherein at least about 10%, at least about 20%, at least about 30%, at least about 40%, at least about 50% at least about 60%, at least about 70%, at least about 80%, at least about 90%, or at least about 95% of said cells are $CD200^+$, $HLA-G^+$ stem cells. In a specific embodiment, said selecting comprises selecting stem cells that are also $CD73^+$ and $CD105^+$. In another specific embodiment, said selecting comprises selecting stem cells that are also $CD34^-$, $CD38^-$ or $CD45^-$. In another specific embodiment, said selecting comprises selecting stem cells that are also $CD34^-$, $CD38^-$, $CD45^-$, $CD73^+$ and $CD105^+$. In another specific embodiment, said selecting also comprises selecting a population of placental stem cells that forms one or more embryoid-like bodies when cultured under conditions that allow the formation of embryoid-like bodies.

In another embodiment, the invention provides an isolated stem cell that is $CD73^+$, $CD105^+$, and $CD200^+$. In an specific embodiment, said isolated stem cell is an isolated placental stem cell. In another specific embodiment, said stem cell is $HLA-G^+$. In another specific embodiment, said stem cell is $CD34^-$, $CD38^-$ or $CD45^-$. In another specific embodiment, said stem cell is $CD34^-$, $CD38^-$ and $CD45^-$. In a more specific embodiment, said stem cell is $CD34^-$, $CD38^-$, $CD45^-$, and $HLA-G^+$. In another specific embodiment, the isolated $CD73^+$, $CD105^+$, and $CD200^+$ stem cell facilitates the formation of one or more embryoid-like bodies in a population of placental cells comprising the stem cell, when the population is cultured under conditions that allow the formation of embryoid-like bodies. In another specific embodiment, said placental stem cell is isolated away from placental cells that are not stem cells. In another specific embodiment, said placental stem cell is isolated away from placental stem cells that do not display these markers.

In another embodiment, the invention also provides a method of selecting a placental stem cell from a plurality of placental cells, comprising selecting a $CD73^+$, $CD105^+$, and $CD200^+$ placental cell, whereby said cell is a placental stem cell. In a specific embodiment, said selecting comprises selecting a placental cell that is also $HLA-G^+$. In another specific embodiment, said selecting comprises selecting a placental cell that is also $CD34^-$, $CD38^-$ or $CD45^-$. In another specific embodiment, said selecting comprises selecting a placental cell that is also $CD34^-$, $CD38^-$ and $CD45^-$. In another specific embodiment, said selecting comprises selecting a placental cell that is also $CD34^-$, $CD38^-$, $CD45^-$, and $HLA-G^+$. In another specific embodiment, said selecting additionally comprises selecting a $CD73^+$, $CD105^+$, and $CD200^+$ stem cell that facilitates the formation of one or more embryoid-like bodies in a population of placental cells comprising the stem cell, when the population is cultured under conditions that facilitate formation of embryoid-like bodies.

In another embodiment, the invention provides an isolated population of cells comprising, e.g., that is enriched for, $CD73^+$, $CD105^+$, $CD200^+$ stem cells. In a specific embodiment, said stem cells are placental stem cells. In various embodiments, at least about 10%, at least about 20%, at least about 30%, at least about 40%, at least about 50%, or at least about 60% of said cells are $CD73^+$, $CD105^+$, $CD200^+$ stem cells. In another embodiment, at least about 70% of said cells in said population of cells are $CD73^+$, $CD105^+$, $CD200^+$ stem cells. In another embodiment, at least about 90%, 95% or 99% of said cells in said population of cells are $CD73^+$, $CD105^+$, $CD200^+$ stem cells. In a specific embodiment of said populations, said stem cells are $HLA-G^+$. In another specific embodiment, said stem cells are $CD34^-$, $CD38^-$ or $CD45^-$. In another specific embodiment, said stem cells are $CD34^-$, $CD38^-$ and $CD45^-$. In a more specific embodiment, said stem cells are $CD34^-$, $CD38^-$, $CD45^-$, and $HLA-G^+$. In another specific embodiment, said population of cells produces one or more embryoid-like bodies when cultured under conditions that allow the formation of embryoid-like bodies. In another specific embodiment, said population of placental stem cells is isolated away from placental cells that are not stem cells. In another specific embodiment, said population of placental stem cells is isolated away from placental stem cells that do not display these characteristics.

In another embodiment, the invention also provides a method of selecting a placental stem cell population from a plurality of placental cells, comprising selecting a population of placental cells wherein at least about 10%, at least about 20%, at least about 30%, at least about 40%, at least about 50%, at least about 60%, at least about 70%, at least about 80%, at least about 90%, or at least about 95% of said cells are $CD73^+$, $CD105^+$, $CD200^+$ stem cells. In a specific embodiment, said selecting comprises selecting stem cells that are also $HLA-G^+$. In another specific embodiment, said selecting comprises selecting stem cells that are also $CD34^-$, $CD38^-$ or $CD45^-$. In another specific embodiment, said selecting comprises selecting stem cells that are also $CD34^-$, $CD38^-$ and $CD45^-$. In another specific embodiment, said selecting comprises selecting stem cells that are also $CD34^-$, $CD38^-$, $CD45^-$, and $HLA-G^+$. In another specific embodiment, said selecting additionally comprises selecting a population of placental cells that produces one or more embryoid-like bodies when the population is cultured under conditions that allow the formation of embryoid-like bodies.

The invention also provides an isolated stem cell that is $CD200^+$ and $OCT-4^+$. In a specific embodiment, the stem cell is $CD73^+$ and $CD105^+$. In a specific embodiment, the stem cell is a placental stem cell. In another specific embodiment, said stem cell is $HLA-G^+$. In another specific embodiment, said stem cell is $CD34^-$, $CD38^-$ or $CD45^-$. In another specific embodiment, said stem cell is $CD34^-$, $CD38^-$ and $CD45^-$. In a more specific embodiment, said stem cell is $CD34^-$, $CD38^-$, $CD45^-$, $CD73^+$, $CD105^+$ and $HLA-G^+$. In another specific embodiment, the stem cell facilitates the production of one or more embryoid-like bodies by a population of placental cells that comprises the stem cell, when the population is cultured under conditions that allow the formation of embryoid-like bodies. In another specific embodiment, said placental stem cell is isolated away from placental cells that are not stem cells. In another specific embodiment, said placental stem cell is isolated away from placental stem cells that do not display these markers.

In another embodiment, the invention also provides a method of selecting a placental stem cell from a plurality of placental cells, comprising selecting a $CD200^+$ and $OCT-4^+$ placental cell, whereby said cell is a placental stem cell. In a specific embodiment, said selecting comprises selecting a placental cell that is also $HLA-G^+$. In another specific embodiment, said selecting comprises selecting a placental cell that is also $CD34^-$, $CD38^-$ or $CD45^-$. In another specific embodiment, said selecting comprises selecting a placental cell that is also $CD34^-$, $CD38^-$ and $CD45^-$. In another specific embodiment, said selecting comprises selecting a placental cell that is also $CD34^-$, $CD38^-$, $CD45^-$, $CD73^+$, $CD105^+$ and $HLA-G^+$. In another specific embodiment, said selecting comprises selecting a placental stem cell that also facilitates the production of one or more embryoid-like bodies by a population of placental cells that comprises the stem cell, when the population is cultured under conditions that allow the formation of embryoid-like bodies.

The invention also provides an isolated population of cells comprising, e.g., that is enriched for, $CD200^+$, $OCT-4^+$ stem cells. In various embodiments, at least about 10%, at least about 20%, at least about 30%, at least about 40%, at least about 50%, or at least about 60% of said cells are $CD200^+$, $OCT-4^+$ stem cells. In another embodiment, at least about 70% of said cells are said $CD200^+$, $OCT-4^+$ stem cells. In another embodiment, at least about 90%, 95%, or 99% of said cells are said $CD200^+$, $OCT-4^+$ stem cells. In a specific embodiment of the isolated populations, said stem cells are $CD73^+$ and $CD105^+$. In another specific embodiment, said stem cells are $HLA-G^+$. In another specific embodiment, said stem cells are $CD34^-$, $CD38^-$ and $CD45^-$. In a more specific embodiment, said stem cells are $CD34^-$, $CD38^-$, $CD45^-$, $CD73^+$, $CD105^+$ and $HLA-G^+$. In another specific embodiment, the population produces one or more embryoid-like bodies when cultured under conditions that allow the formation of embryoid-like bodies. In another specific embodiment, said population of placental stem cells is isolated away from placental cells that are not stem cells. In another specific embodiment, said population of placental stem cells is isolated away from placental stem cells that do not display these characteristics.

In another embodiment, the invention also provides a method of selecting a placental stem cell population from a plurality of placental cells, comprising selecting a population of placental cells wherein at least about 10%, at least about 20%, at least about 30%, at least about 40%, at least about 50% at least about 60%, at least about 70%, at least about 80%, at least about 90%, or at least about 95% of said cells are $CD200^+$, $OCT-4^+$ stem cells. In a specific embodiment, said selecting comprises selecting stem cells that are also $CD73^+$ and $CD105^+$. In another specific embodiment, said selecting comprises selecting stem cells that are also $HLA-G^+$. In another specific embodiment, said selecting comprises selecting stem cells that are also $CD34^-$, $CD38^-$ and $CD45^-$. In another specific embodiment, said stem cells are also $CD34^-$, $CD38^-$, $CD45^-$, $CD73^+$, $CD105^+$ and $HLA-G^+$.

The invention further provides an isolated stem cell that is $CD73^+$, $CD105^+$ and $HLA-G^+$. In a specific embodiment, the stem cell is a placental stem cell. In another specific embodiment, said stem cell is $CD34^-$, $CD38^-$ or $CD45^-$. In another specific embodiment, said stem cell is $CD34^-$, $CD38^-$ and $CD45^-$. In another specific embodiment, said stem cell is $OCT-4^+$. In another specific embodiment, said stem cell is $CD200^+$. In a more specific embodiment, said stem cell is $CD34^-$, $CD38^-$, $CD45^-$, $OCT-4^+$ and $CD200^+$. In another specific embodiment, said stem cell facilitates the formation of embryoid-like bodies in a population of placental cells comprising said stem cell, when the population is cultured under conditions that allow the formation of embryoid-like bodies. In another specific embodiment, said placental stem cell is isolated away from placental cells that are not stem cells. In another specific embodiment, said placental stem cell is isolated away from placental stem cells that do not display these characteristics.

In another embodiment, the invention also provides a method of selecting a placental stem cell from a plurality of placental cells, comprising selecting a $CD73^+$, $CD105^+$ and $HLA-G^+$ placental cell, whereby said cell is a placental stem cell. In a specific embodiment, said selecting comprises selecting a placental cell that is also $CD34^-$, $CD38^-$ or $CD45^-$. In another specific embodiment, said selecting comprises selecting a placental cell that is also $CD34^-$, $CD38^-$ and $CD45^-$. In another specific embodiment, said selecting comprises selecting a placental cell that is also $OCT-4^+$. In another specific embodiment, said selecting comprises selecting a placental cell that is also $CD200^+$. In another specific embodiment, said selecting comprises selecting a placental cell that is also $CD34^-$, $CD38^-$, $CD45^-$, $OCT-4^+$ and $CD200^+$. In another specific embodiment, said selecting comprises selecting a placental cell that also facilitates the formation of one or more embryoid-like bodies in a population of placental cells that comprises said stem cell, when said population is culture under conditions that allow the formation of embryoid-like bodies.

The invention also provides an isolated population of cells comprising, e.g., that is enriched for, $CD73^+$, $CD105^+$ and $HLA-G^+$ stem cells. In a specific embodiment, said stem cells are placental stem cells. In various embodiments, at least about 10%, at least about 20%, at least about 30%, at least about 40%, at least about 50%, or at least about 60% of said cells are $CD73^+$, $CD105^+$ and $HLA-G^+$ stem cells. In another embodiment, at least about 70% of said cells are $CD73^+$, $CD105^+$ and $HLA-G^+$. In another embodiment, at least about 90%, 95% or 99% of said cells are $CD73^+$, $CD105^+$ and $HLA-G^+$ stem cells. In a specific embodiment of the above populations, said stem cells are $CD34^-$, $CD38^-$ or $CD45^-$. In another specific embodiment, said stem cells are $CD34^-$, $CD38^-$ and $CD45^-$. In another specific embodiment, said stem cells are $OCT-4^+$. In another specific embodiment, said stem cells are $CD200^+$. In a more specific embodiment, said stem cells are $CD34^-$, $CD38^-$, $CD45^-$, $OCT-4^+$ and $CD200^+$. In another specific embodiment, said population of placental stem cells is isolated away from placental cells that are not stem cells. In another specific embodiment, said population of placental stem cells is isolated away from placental stem cells that do not display these characteristics.

In another embodiment, the invention also provides a method of selecting a placental stem cell population from a plurality of placental cells, comprising selecting a population of placental cells wherein a majority of said cells are $CD73^+$, $CD105^+$ and $HLA-G^+$. In a specific embodiment, said majority of cells are also $CD34^-$, $CD38^-$ and/or $CD45^-$. In another specific embodiment, said majority of cells are also $CD200^+$. In another specific embodiment, said majority of cells are also $CD34^-$, $CD38^-$, $CD45^-$, $OCT-4^+$ and $CD200^+$.

In another embodiment, the invention provides an isolated stem cell that is $CD73^+$ and $CD105^+$ and which facilitates the formation of one or more embryoid-like bodies in a population of isolated placental cells comprising said stem cell when said population is cultured under conditions that allow formation of embryoid-like bodies. In a specific embodiment, said stem cell is $CD34^-$, $CD38^-$ or $CD45^-$. In another specific embodiment, said stem cell is $CD34^-$, $CD38^-$ and $CD45^-$. In another specific embodiment, said stem cell is $OCT4^+$. In a more specific embodiment, said stem cell is $OCT4^+$, $CD34^-$, $CD38^-$ and $CD45^-$. In another specific embodiment, said placental stem cell is isolated away from placental cells that are not stem cells. In another specific embodiment, said placental stem cell is isolated away from placental stem cells that do not display these characteristics.

The invention further provides a population of isolated placental cells comprising, e.g., that is enriched for, $CD73^+$, $CD105^+$ stem cells, wherein said population forms one or more embryoid-like bodies under conditions that allow formation of embryoid-like bodies. In various embodiments, at least about 10%, at least about 20%, at least about 30%, at least about 40%, at least about 50% at least about 60%, at least about 70%, at least about 80%, at least about 90%, or at least about 95% of said isolated placental cells are $CD73^+$, $CD105^+$ stem cells. In a specific embodiment of the above populations, said stem cells are $CD34^-$, $CD38^-$ or $CD45^-$. In another specific embodiment, said stem cells are $CD34^-$, $CD38^-$ and $CD45^-$. In another specific embodiment, said stem cells are $OCT-4^+$. In a more specific embodiment, said stem cells are $OCT-4^+$, $CD34^-$, $CD38^-$ and $CD45^-$. In other specific embodiments, said population has been expanded, for example, has been passaged at least once, at least three times, at least five times, at least 10 times, at least 15 times, or at least 20 times. In another specific embodiment, said population of placental stem cells is isolated away from placental cells that are not stem cells. In another specific embodiment, said population of placental stem cells is isolated away from placental stem cells that do not display these characteristics.

The invention further provides an isolated stem cell that is $OCT-4^+$ and which facilitates formation of one or more embryoid-like bodies in a population of isolated placental cells comprising said stem cell when cultured under conditions that allow formation of embryoid-like bodies. In a specific embodiment, said stem cell is $CD73^+$ and $CD105^+$. In another specific embodiment, said stem cell is $CD34^-$, $CD38^-$, or $CD45^-$. In another specific embodiment, said stem cell is $CD200^+$. In a more specific embodiment, said stem cell is $CD73^+$, $CD105^+$, $CD200^+$, $CD34^-$, $CD38^-$, and $CD45^-$. In another specific embodiment, said placental stem cell is isolated away from placental cells that are not stem cells. In another specific embodiment, said placental stem cell is isolated away from placental stem cells that do not display these characteristics.

The invention also provides a population of isolated cells comprising, e.g., that is enriched for, $OCT-4^+$ stem cells, wherein said population forms one or more embryoid-like bodies when cultured under conditions that allow the formation of embryoid-like bodies. In various embodiments, at least 10%, at least about 20%, at least about 30%, at least about 40%, at least about 50% at least about 60%, at least about 70%, at least about 80%, at least about 90%, or at least about 95% of said isolated placental cells are $OCT4^+$ stem cells. In a specific embodiment of the above populations, said stem cells are $CD73^+$ and $CD105^+$. In another specific embodiment, said stem cells are $CD34^-$, $CD38^-$, or $CD45^-$. In another specific embodiment, said stem cells are $CD200^+$. In a more specific embodiment, said stem cells are $CD73^+$, $CD105^+$, $CD200^+$, $CD34^-$, $CD38^-$, and $CD45^-$. In another specific embodiment, said population has been expanded, for example, passaged at least once, at least three times, at least five times, at least 10 times, at least 15 times, or at least 20 times. In another specific embodiment, said population of placental stem cells is isolated away from placental cells that are not stem cells. In another specific embodiment, said population of placental stem cells is isolated away from placental stem cells that do not display these characteristics.

In another embodiment, the invention also provides an isolated placental stem cell that is $CD10^+$, $CD34^-$, $CD105^+$, and $CD200^+$. The invention further provides an isolated population of placental stem cells, wherein at least about 70%, at least about 80%, at least about 90%, at least about 95% or at least about 99% of said placental stem cells are $CD10^+$, $CD34^-$, $CD105^+$, $CD200^+$. In a specific embodiment of the above embodiments, said stem cells are additionally $CD90^+$ and $CD45^-$. In a specific embodiment, said stem cell or population of placental stem cells is isolated away from placental cells that are not stem cells. In another specific embodiment, said stem cell or population of placental stem cells is isolated away from placental stem cells that do not display these characteristics. In another specific embodiment, said isolated placental stem cell is non-maternal in origin. In another specific embodiment, at least about 90%, at least about 95%, or at least about 99% of said cells in said isolated population of placental stem cells, are non-maternal in origin.

In another embodiment, the invention provides an isolated placental stem cell that is $HLA-A,B,C^-$, $CD45^-$, $CD133^-$ and $CD34^-$. The invention further provides an isolated population of placental stem cells, wherein at least about 70%, at least about 80%, at least about 90%, at least about 95% or at least about 99% of said placental stem cells are $HLA-A,B,C^-$, CD45⁻, CD133⁻ and CD34⁻. In a specific embodiment, said stem cell or population of placental stem cells is isolated away from placental cells that are not stem cells. In another specific embodiment, said population of placental stem cells is isolated away from placental stem cells that do not display these characteristics. In another specific embodiment, said isolated placental stem cell is non-maternal in origin. In another specific embodiment, at least about 90%, at least about 95%, or at least about 99% of said cells in said isolated population of placental stem cells, are non-maternal in origin. In another embodiment, the invention provides a method of obtaining a placental stem cell that is HLA-A,B,C⁻, CD45⁻, CD133⁻ and CD34⁻ comprising isolating said cell from placental perfusate.

In another embodiment, the invention provides an isolated placental stem cell that is CD10⁺, CD13⁺, CD33⁺, CD45⁻, CD117⁻ and CD133⁻. The invention further provides an isolated population of placental stem cells, wherein at least about 70%, at least about 80%, at least about 90%, at least about 95% or at least about 99% of said placental stem cells are CD10⁺, CD13⁺, CD33⁺, CD45⁻, CD117⁻ and CD133⁻. In a specific embodiment, said stem cell or population of placental stem cells is isolated away from placental cells that are not stem cells. In another specific embodiment, said isolated placental stem cell is non-maternal in origin. In another specific embodiment, at least about 90%, at least about 95%, or at least about 99% of said cells in said isolated population of placental stem cells, are non-maternal in origin. In another specific embodiment, said stem cell or population of placental stem cells is isolated away from placental stem cells that do not display these characteristics. In another embodiment, the invention provides a method of obtaining a placental stem cell that is CD10⁺, CD13⁺, CD33⁺, CD45⁻, CD117⁻ and CD133⁻ comprising isolating said cell from placental perfusate.

In another embodiment, the invention provides an isolated placental stem cell that is CD10⁻, CD33⁻, CD44⁺, CD45⁻, and CD117⁻. The invention further provides an isolated population of placental stem cells, wherein at least about 70%, at least about 80%, at least about 90%, at least about 95% or at least about 99% of said placental stem cells are CD10⁻, CD33⁻, CD44⁺, CD45⁻, and CD117⁻. In a specific embodiment, said stem cell or population of placental stem cells is isolated away from placental cells that are not stem cells. In another specific embodiment, said isolated placental stem cell is non-maternal in origin. In another specific embodiment, at least about 90%, at least about 95%, or at least 99% of said cells in said isolated population of placental stem cells, are non-maternal in origin. In another specific embodiment, said stem cell or population of placental stem cells is isolated away from placental stem cells that do not display these characteristics. In another embodiment, the invention provides a method of obtaining a placental stem cell that is CD10⁻, CD33⁻, CD44⁺, CD45⁻, CD117⁻ comprising isolating said cell from placental perfusate.

In another embodiment, the invention provides an isolated placental stem cell that is CD10⁻, CD13⁻, CD33⁻, CD45⁻, and CD117⁻. The invention further provides an isolated population of placental stem cells, wherein at least about 70%, at least about 80%, at least about 90%, at least about 95% or at least about 99% of said placental stem cells are CD10⁻, CD13⁻, CD33⁻, CD45⁻, and CD117⁻. In a specific embodiment, said stem cell or population of placental stem cells is isolated away from placental cells that are not stem cells. In another specific embodiment, said isolated placental stem cell is non-maternal in origin. In another specific embodiment, at least about 90%, at least about 95%, or at least about 99% of said cells in said isolated population of placental stem cells, are non-maternal in origin. In another specific embodiment, said stem cell or population of placental stem cells is isolated away from placental stem cells that do not display these characteristics. In another embodiment, the invention provides a method of obtaining a placental stem cell that is CD10⁻, CD13⁻, CD33⁻, CD45⁻, and CD117⁺ comprising isolating said cell from placental perfusate.

In another embodiment, the invention provides an isolated placental stem cell that is HLA A,B,C⁻, CD45⁻, CD34⁻, CD133⁻, positive for CD10, CD13, CD38, CD44, CD90, CD105, CD200 and/or HLA-G, and/or negative for CD117. The invention further provides an isolated population of placental stem cells, wherein said stem cells are HLA A,B,C⁻, CD45⁻, CD34⁻, CD133⁻, and at least about 20%, 25%, 30%, 35%, 40%, 45%, 50%, 55%, 60%, 65%, 70%, 75%, 80%, 85%, 90%, 95%, 98% or about 99% of the stem cells in the population are positive for CD10, CD13, CD38, CD44, CD90, CD105, CD200 and/or HLA-G, and/or negative for CD117. In a specific embodiment, said stem cell or population of placental stem cells is isolated away from placental cells that are not stem cells. In another specific embodiment, said isolated placental stem cell is non-maternal in origin. In another specific embodiment, at least about 90%, at least about 95%, or at least about 99%, of said cells in said isolated population of placental stem cells, are non-maternal in origin. In another specific embodiment, said stem cell or population of placental stem cells is isolated away from placental stem cells that do not display these characteristics. In another embodiment, the invention provides a method of obtaining a placental stem cell that is HLA A,B,C⁻, CD45⁻, CD34⁻, CD133⁻ and positive for CD10, CD13, CD38, CD44, CD90, CD105, CD200 and/or HLA-G, and/or negative for CD117, comprising isolating said cell from placental perfusate.

In another embodiment, the invention provides a placental stem cell that is CD200⁺ and CD10⁺, as determined by antibody binding, and CD117⁻, as determined by both antibody binding and RT-PCR. In another embodiment, the invention provides a placental stem cell that is CD10⁺, CD29⁻, CD54⁺, CD200⁺, HLA-G⁺, HLA class F and β-2-microglobulin⁻. In another embodiment, the invention provides placental stem cells, wherein the expression of at least one marker is at least two-fold higher than for a mesenchymal stem cell (e.g., a bone marrow-derived mesenchymal stem cell). In another specific embodiment, said isolated placental stem cell is non-maternal in origin. In another specific embodiment, at least about 90%, at least about 95%, or at least 99%, of said cells in said isolated population of placental stem cells, are non-maternal in origin.

In another embodiment, the invention provides an isolated population of placental stem cells, wherein a plurality of said placental stem cells are positive for aldehyde dehydrogenase (ALDH), as assessed by an aldehyde dehydrogenase activity assay. Such assays are known in the art (see, e.g., Bostian and Betts, *Biochem. J.*, 173, 787, (1978)). In a specific embodiment, said ALDH assay uses ALDEFLUOR® (Aldagen, Inc., Ashland, Oreg.) as a marker of aldehyde dehydrogenase activity. In a specific embodiment, said plurality is between about 3% and about 25% of cells in said population of cells. In another embodiment, the invention provides a population of umbilical cord stem cells, wherein a plurality of said umbilical cord stem cells are positive for aldehyde dehydrogenase, as assessed by an aldehyde dehydrogenase activity assay that uses ALDEFLUOR® as an indicator of aldehyde dehydrogenase activity. In a specific embodiment, said plurality is between about 3% and about 25% of cells in said population of cells. In another embodiment, said population of placental stem cells or umbilical cord stem cells shows at least three-fold, or at least five-fold, higher ALDH activity than a population of bone marrow-derived mesenchymal stem cells having the same number of cells and cultured under the same conditions.

The invention provides any of the above placental stem cells, or populations of placental stem cells, wherein the stem cell or population of placental stem cells has been passaged at least 1, 2, 3, 4, 5, 6, 7, 8, 9, 10, 12, 14, 16, 18, or 20 times, or more, or expanded for 1, 2, 3, 4, 5, 6, 7, 8, 9, 10, 12, 14, 16, 18, 20, 22, 24, 26, 28, 30, 32, 34, 36, 38 or 40 population doublings, or more.

In a specific embodiment of any of the above placental cells or cell populations, the karyotype of the cells, or at least about 95% or about 99% of the cells in said population, is normal. In another specific embodiment of any of the above placental cells or cell populations, the cells, or cells in the population of cells, are non-maternal in origin.

Isolated placental stem cells, or isolated populations of placental stem cells, bearing any of the above combinations of markers, can be combined in any ratio. The invention also provides for the isolation of, or enrichment for, any two or more of the above placental stem cell populations to form a placental stem cell population. For example, the invention provides an isolated population of placental stem cells comprising a first population of placental stem cells defined by one of the marker combinations described above and a second population of placental stem cells defined by another of the marker combinations described above, wherein said first and second populations are combined in a ratio of about 1:99, 2:98, 3:97, 4:96, 5:95, 10:90, 20:80, 30:70, 40:60, 50:50, 60:40, 70:30, 80:20, 90:10, 95:5, 96:4, 97:3, 98:2, or about 99:1. In like fashion, any three, four, five or more of the above-described placental stem cells or placental stem cell populations can be combined.

The invention further provides placental stem cells that are obtained by disruption of placental tissue, with or without enzymatic digestion, followed by culture (see Section 5.2.3) or perfusion (see Section 5.2.4). For example, the invention provides an isolated population of placental stem cells that is produced according to a method comprising perfusing a mammalian placenta that has been drained of cord blood and perfused to remove residual blood; perfusing said placenta with a perfusion solution; and collecting said perfusion solution, wherein said perfusion solution after perfusion comprises a population of placental cells that comprises placental stem cells; and isolating a plurality of said placental stem cells from said population of cells. In a specific embodiment, the perfusion solution is passed through both the umbilical vein and umbilical arteries and collected after it exudes from the placenta. Populations of placental stem cells produced by this method typically comprise a mixture of fetal and maternal cells. In another specific embodiment, the perfusion solution is passed through the umbilical vein and collected from the umbilical arteries, or passed through the umbilical arteries and collected from the umbilical vein. Populations of placental stem cells produced by this method typically are substantially exclusively fetal in origin; that is, e.g., greater than 90%, 95%, 99%, or 99.5% of the placental stem cells in the population are fetal in origin.

In various embodiments, the placental stem cells, contained within a population of cells obtained from perfusion of a placenta, are at least 50%, 60%, 70%, 80%, 90%, 95%, 99% or at least 99.5% of said population of placental cells. In another specific embodiment, the placental stem cells collected by perfusion comprise fetal and maternal cells. In another specific embodiment, the placental stem cells collected by perfusion are at least 50%, 60%, 70%, 80%, 90%, 95%, 99% or at least 99.5% fetal cells.

In another specific embodiment, the invention provides a composition comprising a population of isolated placental stem cells collected by perfusion, wherein said composition comprises at least a portion of the perfusion solution used to collect the placental stem cells.

The invention further provides an isolated population of the placental stem cells described herein that is produced according to a method comprising digesting placental tissue with a tissue-disrupting enzyme to obtain a population of placental cells comprising placental stem cells, and isolating a plurality of placental stem cells from the remainder of said placental cells. The whole, or any part of, the placenta can be digested to obtain placental stem cells. In specific embodiments, for example, said placental tissue is a whole placenta, an amniotic membrane, chorion, a combination of amnion and chorion, or a combination of any of the foregoing. In other specific embodiment, the tissue-disrupting enzyme is trypsin or collagenase. In various embodiments, the placental stem cells, contained within a population of cells obtained from digesting a placenta, are at least 50%, 60%, 70%, 80%, 90%, 95%, 99% or at least 99.5% of said population of placental cells.

Gene profiling confirms that isolated placental stem cells, and populations of isolated placental stem cells, are distinguishable from other cells, e.g., mesenchymal stem cells, e.g., bone marrow-derived stem cells. The placental stem cells described herein, can be distinguished from mesenchymal stem cells on the basis of the expression of one or more genes, the expression of which is specific to placental stem cells or umbilical cord stem cells in comparison to bone marrow-derived mesenchymal stem cells. In particular, placental stem cells can be distinguished from mesenchymal stem cells on the basis of the expression of one or more gene, the expression of which is significantly higher (that is, at least twofold higher) in placental stem cells than in mesenchymal stem cells, wherein the one or more gene is(are) ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, ZC3H12A, or a combination of any of the foregoing, wherein the expression of these genes is higher in placental stem cells or umbilical cord stem cells than in bone marrow-derived stem cells, when the stem cells are grown under equivalent conditions. In a specific embodiment, the placental stem cell-specific or umbilical cord stem cell-specific gene is CD200.

The level of expression of these genes can be used to confirm the identity of a population of placental cells, to identify a population of cells as comprising at least a plurality of placental stem cells, or the like. The population of placental stem cells, the identity of which is confirmed, can be clonal, e.g., a population of placental stem cells expanded form a single placental stem cell, or a mixed population of stem cells, e.g., a population of cells comprising solely placental stem cells that are expanded from multiple placental stem cells, or a population of cells comprising placental stem cells and at least one other type of cell.

The level of expression of these genes can be used to select populations of placental stem cells. For example, a population of cells, e.g., clonally-expanded cells, is selected if the expression of one or more of these genes is significantly higher in a sample from the population of cells than in an equivalent population of mesenchymal stem cells. Such selecting can be of a population from a plurality of placental stem cells populations, from a plurality of cell populations, the identity of which is not known, etc.

Placental stem cells can be selected on the basis of the level of expression of one or more such genes as compared to the level of expression in said one or more genes in a mesenchymal stem cell control. In one embodiment, the level of expression of said one or more genes in a sample comprising an equivalent number of mesenchymal stem cells is used as a control. In another embodiment, the control, for placental stem cells tested under certain conditions, is a numeric value representing the level of expression of said one or more genes in mesenchymal stem cells under said conditions.

The placental stem cells of the invention display the above characteristics (e.g., combinations of cell surface markers and/or gene expression profiles) in primary culture, or during proliferation in medium comprising 60% DMEM-LG (Gibco), 40% MCDB-201(Sigma), 2% fetal calf serum (FCS) (Hyclone Laboratories), 1× insulin-transferrin-selenium (ITS), 1× lenolenic-acid-bovine-serum-albumin (LA-BSA), $10^{-9}$ M dexamethasone (Sigma), $10^{-4}$M ascorbic acid 2-phosphate (Sigma), epidermal growth factor (EGF) 10 ng/ml (R&D Systems), platelet derived-growth factor (PDGF-BB) 10 ng/ml (R&D Systems), and 100 U penicillin/ 1000 U streptomycin.

The isolated populations of placental stem cells described above, and populations of placental stem cells generally, can comprise about, at least, or no more than, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more placental stem cells.

5.1.3 Growth in Culture

The growth of the placental stem cells described herein, as for any mammalian cell, depends in part upon the particular medium selected for growth. Under optimum conditions, placental stem cells typically double in number in 3-5 days. During culture, the placental stem cells of the invention adhere to a substrate in culture, e.g. the surface of a tissue culture container (e.g., tissue culture dish plastic, fibronectin-coated plastic, and the like) and form a monolayer.

Populations of isolated placental cells that comprise the placental stem cells of the invention, when cultured under appropriate conditions, form embryoid-like bodies, that is, three-dimensional clusters of cells grow atop the adherent stem cell layer. Cells within the embryoid-like bodies express markers associated with very early stem cells, e.g., OCT-4, Nanog, SSEA3 and SSEA4. Cells within the embryoid-like bodies are typically not adherent to the culture substrate, as are the placental stem cells described herein, but remain attached to the adherent cells during culture. Embryoid-like body cells are dependent upon the adherent placental stem cells for viability, as embryoid-like bodies do not form in the absence of the adherent stem cells. The adherent placental stem cells thus facilitate the growth of one or more embryoid-like bodies in a population of placental cells that comprise the adherent placental stem cells. Without wishing to be bound by theory, the cells of the embryoid-like bodies are thought to grow on the adherent placental stem cells much as embryonic stem cells grow on a feeder layer of cells. Mesenchymal stem cells, e.g., bone marrow-derived mesenchymal stem cells, do not develop embryoid-like bodies in culture.

5.2 Methods of Obtaining Placental Stem Cells 5.2.1 Stem Cell Collection Composition The present invention further provides methods of collecting and isolating placental stem cells. Generally, stem cells are obtained from a mammalian placenta using a physiologically-acceptable solution, e.g., a stem cell collection composition. A stem cell collection composition is described in detail in related U.S. Provisional Application No. 60/754, 969, entitled "Improved Medium for Collecting Placental Stem Cells and Preserving Organs," filed on Dec. 29, 2005.

The stem cell collection composition can comprise any physiologically-acceptable solution suitable for the collection and/or culture of stem cells, for example, a saline solution (e.g., phosphate-buffered saline, Kreb's solution, modified Kreb's solution, Eagle's solution, 0.9% NaCl. etc.), a culture medium (e.g., DMEM, H.DMEM, etc.), and the like.

The stem cell collection composition can comprise one or more components that tend to preserve placental stem cells, that is, prevent the placental stem cells from dying, or delay the death of the placental stem cells, reduce the number of placental stem cells in a population of cells that die, or the like, from the time of collection to the time of culturing. Such components can be, e.g., an apoptosis inhibitor (e.g., a caspase inhibitor or JNK inhibitor); a vasodilator (e.g., magnesium sulfate, an antihypertensive drug, atrial natriuretic peptide (ANP), adrenocorticotropin, corticotropin-releasing hormone, sodium nitroprusside, hydralazine, adenosine triphosphate, adenosine, indomethacin or magnesium sulfate, a phosphodiesterase inhibitor, etc.); a necrosis inhibitor (e.g., 2-(1H-Indol-3-yl)-3-pentylamino-maleimide, pyrrolidine dithiocarbamate, or clonazepam); a TNF-α inhibitor; and/or an oxygen-carrying perfluorocarbon (e.g., perfluorooctyl bromide, perfluorodecyl bromide, etc.).

The stem cell collection composition can comprise one or more tissue-degrading enzymes, e.g., a metalloprotease, a serine protease, a neutral protease, an RNase, or a DNase, or the like. Such enzymes include, but are not limited to, collagenases (e.g., collagenase I, II, III or IV, a collagenase from *Clostridium histolyticum*, etc.); dispase, thermolysin, elastase, trypsin, LIBERASE, hyaluronidase, and the like.

The stem cell collection composition can comprise a bacteriocidally or bacteriostatically effective amount of an antibiotic. In certain non-limiting embodiments, the antibiotic is a macrolide (e.g., tobramycin), a cephalosporin (e.g., cephalexin, cephradine, cefuroxime, cefprozil, cefaclor, cefixime or cefadroxil), a clarithromycin, an erythromycin, a penicillin (e.g., penicillin V) or a quinolone (e.g., ofloxacin, ciprofloxacin or norfloxacin), a tetracycline, a streptomycin, etc. In a particular embodiment, the antibiotic is active against Gram (+) and/or Gram(−) bacteria, e.g., *Pseudomonas aeruginosa, Staphylococcus aureus*, and the like.

The stem cell collection composition can also comprise one or more of the following compounds: adenosine (about 1 mM to about 50 mM); D-glucose (about 20 mM to about 100 mM); magnesium ions (about 1 mM to about 50 mM); a macromolecule of molecular weight greater than 20,000 daltons, in one embodiment, present in an amount sufficient to maintain endothelial integrity and cellular viability (e.g., a synthetic or naturally occurring colloid, a polysaccharide such as dextran or a polyethylene glycol present at about 25 g/l to about 100 g/l, or about 40 g/l to about 60 g/l); an antioxidant (e.g., butylated hydroxyanisole, butylated hydroxytoluene, glutathione, vitamin C or vitamin E present at about 25 μM to about 100 μM); a reducing agent (e.g., N-acetylcysteine present at about 0.1 mM to about 5 mM); an agent that prevents calcium entry into cells (e.g., verapamil present at about 2 μM to about 25 μM); nitroglycerin (e.g., about 0.05 g/L to about 0.2 g/L); an anticoagulant, in one embodiment, present in an amount sufficient to help prevent clotting of residual blood (e.g., heparin or hirudin present at a concentration of about 1000 units/l to about 100,000 units/l);

or an amiloride containing compound (e.g., amiloride, ethyl isopropyl amiloride, hexamethylene amiloride, dimethyl amiloride or isobutyl amiloride present at about 1.0 µM to about 5 µM).

5.2.2 Collection and Handling of Placenta

Generally, a human placenta is recovered shortly after its expulsion after birth. In a preferred embodiment, the placenta is recovered from a patient after informed consent and after a complete medical history of the patient is taken and is associated with the placenta. Preferably, the medical history continues after delivery. Such a medical history can be used to coordinate subsequent use of the placenta or the stem cells harvested therefrom. For example, human placental stem cells can be used, in light of the medical history, for personalized medicine for the infant associated with the placenta, or for parents, siblings or other relatives of the infant.

Prior to recovery of placental stem cells, the umbilical cord blood and placental blood are removed. In certain embodiments, after delivery, the cord blood in the placenta is recovered. The placenta can be subjected to a conventional cord blood recovery process. Typically a needle or cannula is used, with the aid of gravity, to exsanguinate the placenta (see, e.g., Anderson, U.S. Pat. No. 5,372,581; Hessel et al., U.S. Pat. No. 5,415,665). The needle or cannula is usually placed in the umbilical vein and the placenta can be gently massaged to aid in draining cord blood from the placenta. Such cord blood recovery may be performed commercially, e.g., LifeBank USA, Cedar Knolls, N.J., ViaCord, Cord Blood Registry and Cryocell. Preferably, the placenta is gravity drained without further manipulation so as to minimize tissue disruption during cord blood recovery.

Typically, a placenta is transported from the delivery or birthing room to another location, e.g., a laboratory, for recovery of cord blood and collection of stem cells by, e.g., perfusion or tissue dissociation. The placenta is preferably transported in a sterile, thermally insulated transport device (maintaining the temperature of the placenta between 20-28° C.), for example, by placing the placenta, with clamped proximal umbilical cord, in a sterile zip-lock plastic bag, which is then placed in an insulated container. In another embodiment, the placenta is transported in a cord blood collection kit substantially as described in pending U.S. Pat. No. 7,147,626. Preferably, the placenta is delivered to the laboratory four to twenty-four hours following delivery. In certain embodiments, the proximal umbilical cord is clamped, preferably within 4-5 cm (centimeter) of the insertion into the placental disc prior to cord blood recovery. In other embodiments, the proximal umbilical cord is clamped after cord blood recovery but prior to further processing of the placenta.

The placenta, prior to stem cell collection, can be stored under sterile conditions and at either room temperature or at a temperature of 5 to 25° C. (centigrade). The placenta may be stored for a period of for a period of four to twenty-four hours, up to forty-eight hours, or longer than forty eight hours, prior to perfusing the placenta to remove any residual cord blood. In one embodiment, the placenta is harvested from between about zero hours to about two hours post-expulsion. The placenta is preferably stored in an anticoagulant solution at a temperature of 5 to 25° C. (centigrade). Suitable anticoagulant solutions are well known in the art. For example, a solution of heparin or warfarin sodium can be used. In a preferred embodiment, the anticoagulant solution comprises a solution of heparin (e.g., 1% w/w in 1:1000 solution). The exsanguinated placenta is preferably stored for no more than 36 hours before placental stem cells are collected.

The mammalian placenta or a part thereof, once collected and prepared generally as above, can be treated in any art-known manner, e.g., can be perfused or disrupted, e.g., digested with one or more tissue-disrupting enzymes, to obtain stem cells.

5.2.3 Physical Disruption and Enzymatic Digestion of Placental Tissue

In one embodiment, stem cells are collected from a mammalian placenta by physical disruption of part of all of the organ. For example, the placenta, or a portion thereof, may be, e.g., crushed, sheared, minced, diced, chopped, macerated or the like. The tissue can then be cultured to obtain a population of stem cells. Typically, the placental tissue is disrupted using, e.g., in, a stem cell collection composition (see Section 5.2.1 and below).

The placenta can be dissected into components prior to physical disruption and/or enzymatic digestion and stem cell recovery. Placental stem cells can be obtained from all or a portion of the amniotic membrane, chorion, umbilical cord, placental cotyledons, or any combination thereof, including from a whole placenta. Preferably, placental stem cells are obtained from placental tissue comprising amnion and chorion. Typically, placental stem cells can be obtained by disruption of a small block of placental tissue, e.g., a block of placental tissue that is about 1, 2, 3, 4, 5, 6, 7, 8, 9, 10, 20, 30, 40, 50, 60, 70, 80, 90, 100, 200, 300, 400, 500, 600, 700, 800, 900 or about 1000 cubic millimeters in volume. Any method of physical disruption can be used, provided that the method of disruption leaves a plurality, more preferably a majority, and more preferably at least 60%, 70%, 80%, 90%, 95%, 98%, or 99% of the cells in said organ viable, as determined by, e.g., trypan blue exclusion.

Stem cells can generally be collected from a placenta, or portion thereof, at any time within about the first three days post-expulsion, but preferably between about 8 hours and about 18 hours post-expulsion.

In a specific embodiment, the disrupted tissue is cultured in tissue culture medium suitable for the proliferation of placental stem cells (see, e.g., Section 5.3, below, describing the culture of placental stem cells).

In another specific embodiment, stem cells are collected by physical disruption of placental tissue, wherein the physical disruption includes enzymatic digestion, which can be accomplished by use of one or more tissue-digesting enzymes. The placenta, or a portion thereof, may also be physically disrupted and digested with one or more enzymes, and the resulting material then immersed in, or mixed into, a stem cell collection composition.

A preferred stem cell collection composition comprises one or more tissue-disruptive enzyme(s). Enzymatic digestion preferably uses a combination of enzymes, e.g., a combination of a matrix metalloprotease and a neutral protease, for example, a combination of collagenase and dispase. In one embodiment, enzymatic digestion of placental tissue uses a combination of a matrix metalloprotease, a neutral protease, and a mucolytic enzyme for digestion of hyaluronic acid, such as a combination of collagenase, dispase, and hyaluronidase or a combination of LIBERASE (Boehringer Mannheim Corp., Indianapolis, Ind.) and hyaluronidase. Other enzymes that can be used to disrupt placenta tissue include papain, deoxyribonucleases, serine proteases, such as trypsin, chymotrypsin, or elastase. Serine proteases may be inhibited by alpha 2 microglobulin in serum and therefore the medium used for digestion is usually serum-free. EDTA and DNase are commonly used in enzyme digestion procedures to increase the efficiency of cell recovery. The digestate is preferably diluted so as to avoid trapping stem cells within the viscous digest.

Any combination of tissue digestion enzymes can be used. Typical concentrations for tissue digestion enzymes include, e.g., 50-200 U/mL for collagenase I and collagenase IV, 1-10 U/mL for dispase, and 10-100 U/mL for elastase. Proteases can be used in combination, that is, two or more proteases in the same digestion reaction, or can be used sequentially in order to liberate placental stem cells. For example, in one embodiment, a placenta, or part thereof, is digested first with an appropriate amount of collagenase I at about 1 to about 2 mg/ml for, e.g., 30 minutes, followed by digestion with trypsin, at a concentration of about 0.25%, for, e.g., 10 minutes, at 37° C. Serine proteases are preferably used consecutively following use of other enzymes.

In another embodiment, the tissue can further be disrupted by the addition of a chelator, e.g., ethylene glycol bis(2-aminoethyl ether)-N,N,N'N'-tetraacetic acid (EGTA) or ethylenediaminetetraacetic acid (EDTA) to the stem cell collection composition comprising the stem cells, or to a solution in which the tissue is disrupted and/or digested prior to isolation of the stem cells with the stem cell collection composition.

In one embodiment, a digestion can proceed as follows. Approximately a gram of placental tissue is obtained and minced. The tissue is digested in 10 mL of a solution comprising about 1 mg/mL collagenase 1A and about 0.25% trypsin at 37° C. in a shaker at about 100 RPM. The digestate is washed three times with culture medium, and the washed cells are seeded into 2 T-75 flasks. The cells are then isolated by differential adherence, and characterized for, e.g., viability, cell surface markers, differentiation, and the like.

It will be appreciated that where an entire placenta, or portion of a placenta comprising both fetal and maternal cells (for example, where the portion of the placenta comprises the chorion or cotyledons), the placental stem cells collected will comprise a mix of placental stem cells derived from both fetal and maternal sources. Where a portion of the placenta that comprises no, or a negligible number of, maternal cells (for example, amnion), the placental stem cells collected will comprise almost exclusively fetal placental stem cells.

Stem cells can be isolated from disrupted tissue by differential trypsinization (see Section 5.2.5, below) followed by culture in one or more new culture containers in fresh proliferation medium, optionally followed by a second differential trypsinization step.

5.2.4 Placental Perfusion

Placental stem cells can also be obtained by perfusion of the mammalian placenta. Methods of perfusing mammalian placenta to obtain stem cells are disclosed, e.g., in Hariri, U.S. Application Publication No. 2002/0123141, and in related U.S. Provisional Application No. 60/754,969, entitled "Improved Medium for Collecting Placental Stem Cells and Preserving Organs," filed on Dec. 29, 2005.

Placental stem cells can be collected by perfusion, e.g., through the placental vasculature, using, e.g., a stem cell collection composition as a perfusion solution. In one embodiment, a mammalian placenta is perfused by passage of perfusion solution through either or both of the umbilical artery and umbilical vein. The flow of perfusion solution through the placenta may be accomplished using, e.g., gravity flow into the placenta. Preferably, the perfusion solution is forced through the placenta using a pump, e.g., a peristaltic pump. The umbilical vein can be, e.g., cannulated with a cannula, e.g., a TEFLON® or plastic cannula, that is connected to a sterile connection apparatus, such as sterile tubing. The sterile connection apparatus is connected to a perfusion manifold.

In preparation for perfusion, the placenta is preferably oriented (e.g., suspended) in such a manner that the umbilical artery and umbilical vein are located at the highest point of the placenta. The placenta can be perfused by passage of a perfusion fluid through the placental vasculature and surrounding tissue. The placenta can also be perfused by passage of a perfusion fluid into the umbilical vein and collection from the umbilical arteries, or passage of a perfusion fluid into the umbilical arteries and collection from the umbilical vein.

In one embodiment, for example, the umbilical artery and the umbilical vein are connected simultaneously, e.g., to a pipette that is connected via a flexible connector to a reservoir of the perfusion solution. The perfusion solution is passed into the umbilical vein and artery. The perfusion solution exudes from and/or passes through the walls of the blood vessels into the surrounding tissues of the placenta, and is collected in a suitable open vessel from the surface of the placenta that was attached to the uterus of the mother during gestation. The perfusion solution may also be introduced through the umbilical cord opening and allowed to flow or percolate out of openings in the wall of the placenta which interfaced with the maternal uterine wall. Placental cells that are collected by this method, which can be referred to as a "pan" method, are typically a mixture of fetal and maternal cells.

In another embodiment, the perfusion solution is passed through the umbilical veins and collected from the umbilical artery, or is passed through the umbilical artery and collected from the umbilical veins. Placental cells collected by this method, which can be referred to as a "closed circuit" method, are typically almost exclusively fetal.

It will be appreciated that perfusion using the pan method, that is, whereby perfusate is collected after it has exuded from the maternal side of the placenta, results in a mix of fetal and maternal cells. As a result, the cells collected by this method comprise a mixed population of placental stem cells of both fetal and maternal origin. In contrast, perfusion solely through the placental vasculature in the closed circuit method, whereby perfusion fluid is passed through one or two placental vessels and is collected solely through the remaining vessel(s), results in the collection of a population of placental stem cells almost exclusively of fetal origin.

The closed circuit perfusion method can, in one embodiment, be performed as follows. A post-partum placenta is obtained within about 48 hours after birth. The umbilical cord is clamped and cut above the clamp. The umbilical cord can be discarded, or can processed to recover, e.g., umbilical cord stem cells, and/or to process the umbilical cord membrane for the production of a biomaterial. The amniotic membrane can be retained during perfusion, or can be separated from the chorion, e.g., using blunt dissection with the fingers. If the amniotic membrane is separated from the chorion prior to perfusion, it can be, e.g., discarded, or processed, e.g., to obtain stem cells by enzymatic digestion, or to produce, e.g., an amniotic membrane biomaterial, e.g., the biomaterial described in U.S. Application Publication No. 2004/0048796. After cleaning the placenta of all visible blood clots and residual blood, e.g., using sterile gauze, the umbilical cord vessels are exposed, e.g., by partially cutting the umbilical cord membrane to expose a cross-section of the cord. The vessels are identified, and opened, e.g., by advancing a closed alligator clamp through the cut end of each vessel. The apparatus, e.g., plastic tubing connected to a perfusion device or peristaltic pump, is then inserted into each of the placental arteries. The pump can be any pump suitable for the purpose, e.g., a peristaltic pump. Plastic tubing, connected to a sterile collection reservoir, e.g., a blood bag such as a 250 mL collection bag, is then inserted into the placental vein. Alternatively, the tubing connected to the pump is inserted into the placental vein, and tubes to a collection reservoir(s) are inserted into one or both of the placental arteries. The placenta is then perfused with a volume of perfusion solution, e.g., about 750 ml of perfusion solution. Cells in the perfusate are then collected, e.g., by centrifugation.

In one embodiment, the proximal umbilical cord is clamped during perfusion, and more preferably, is clamped within 4-5 cm (centimeter) of the cord's insertion into the placental disc.

The first collection of perfusion fluid from a mammalian placenta during the exsanguination process is generally colored with residual red blood cells of the cord blood and/or placental blood. The perfusion fluid becomes more colorless as perfusion proceeds and the residual cord blood cells are washed out of the placenta. Generally from 30 to 100 ml (milliliter) of perfusion fluid is adequate to initially exsanguinate the placenta, but more or less perfusion fluid may be used depending on the observed results.

The volume of perfusion liquid used to collect placental stem cells may vary depending upon the number of stem cells to be collected, the size of the placenta, the number of collections to be made from a single placenta, etc. In various embodiments, the volume of perfusion liquid may be from 50 mL to 5000 mL, 50 mL to 4000 mL, 50 mL to 3000 mL, 100 mL to 2000 mL, 250 mL to 2000 mL, 500 mL to 2000 mL, or 750 mL to 2000 mL. Typically, the placenta is perfused with 700-800 mL of perfusion liquid following exsanguination.

The placenta can be perfused a plurality of times over the course of several hours or several days. Where the placenta is to be perfused a plurality of times, it may be maintained or cultured under aseptic conditions in a container or other suitable vessel, and perfused with the stem cell collection composition, or a standard perfusion solution (e.g., a normal saline solution such as phosphate buffered saline ("PBS")) with or without an anticoagulant (e.g., heparin, warfarin sodium, coumarin, bishydroxycoumarin), and/or with or without an antimicrobial agent (e.g., β-mercaptoethanol (0.1 mM); antibiotics such as streptomycin (e.g., at 40-100 μg/ml), penicillin (e.g., at 40 U/ml), amphotericin B (e.g., at 0.5 μg/ml). In one embodiment, an isolated placenta is maintained or cultured for a period of time without collecting the perfusate, such that the placenta is maintained or cultured for 1, 2, 3, 4, 5, 6, 7, 8, 9, 10, 11, 12, 13, 14, 15, 16, 17, 18, 19, 20, 21, 22, 23, or 24 hours, or 2 or 3 or more days before perfusion and collection of perfusate. The perfused placenta can be maintained for one or more additional time(s), e.g., 1, 2, 3, 4, 5, 6, 7, 8, 9, 10, 11, 12, 13, 14, 15, 16, 17, 18, 19, 20, 21, 22, 23, 24 or more hours, and perfused a second time with, e.g., 700-800 mL perfusion fluid. The placenta can be perfused 1, 2, 3, 4, 5 or more times, for example, once every 1, 2, 3, 4, 5 or 6 hours. In a preferred embodiment, perfusion of the placenta and collection of perfusion solution, e.g., stem cell collection composition, is repeated until the number of recovered nucleated cells falls below 100 cells/ml. The perfusates at different time points can be further processed individually to recover time-dependent populations of cells, e.g., stem cells. Perfusates from different time points can also be pooled. In a preferred embodiment, stem cells are collected at a time or times between about 8 hours and about 18 hours post-expulsion.

Without wishing to be bound by any theory, after exsanguination and a sufficient time of perfusion of the placenta, placental stem cells are believed to migrate into the exsanguinated and perfused microcirculation of the placenta where, according to the methods of the invention, they are collected, preferably by washing into a collecting vessel by perfusion. Perfusing the isolated placenta not only serves to remove residual cord blood but also provide the placenta with the appropriate nutrients, including oxygen. The placenta may be cultivated and perfused with a similar solution which was used to remove the residual cord blood cells, preferably, without the addition of anticoagulant agents.

Perfusion according to the methods of the invention results in the collection of significantly more placental stem cells than the number obtainable from a mammalian placenta not perfused with said solution, and not otherwise treated to obtain stem cells (e.g., by tissue disruption, e.g., enzymatic digestion). In this context, "significantly more" means at least 10% more. Perfusion according to the methods of the invention yields significantly more placental stem cells than, e.g., the number of placental stem cells obtainable from culture medium in which a placenta, or portion thereof, has been cultured.

Stem cells can be isolated from placenta by perfusion with a solution comprising one or more proteases or other tissue-disruptive enzymes. In a specific embodiment, a placenta or portion thereof (e.g., amniotic membrane, amnion and chorion, placental lobule or cotyledon, umbilical cord, or combination of any of the foregoing) is brought to 25-37° C., and is incubated with one or more tissue-disruptive enzymes in 200 mL of a culture medium for 30 minutes. Cells from the perfusate are collected, brought to 4° C., and washed with a cold inhibitor mix comprising 5 mM EDTA, 2 mM dithiothreitol and 2 mM beta-mercaptoethanol. The stem cells are washed after several minutes with a cold (e.g., 4° C.) stem cell collection composition of the invention.

5.2.5 Isolation, Sorting and Characterization of Placental Stem Cells

Stem cells from mammalian placenta, whether obtained by perfusion or enzymatic digestion, can initially be purified from (i.e., be isolated from) other cells by Ficoll gradient centrifugation. Such centrifugation can follow any standard protocol for centrifugation speed, etc. In one embodiment, for example, cells collected from the placenta are recovered from perfusate by centrifugation at 5000×g for 15 minutes at room temperature, which separates cells from, e.g., contaminating debris and platelets. In another embodiment, placental perfusate is concentrated to about 200 ml, gently layered over Ficoll, and centrifuged at about 1100×g for 20 minutes at 22° C., and the low-density interface layer of cells is collected for further processing.

Cell pellets can be resuspended in fresh stem cell collection composition, or a medium suitable for stem cell maintenance, e.g., IMDM serum-free medium containing 2 U/ml heparin and 2 mM EDTA (GibcoBRL, NY). The total mononuclear cell fraction can be isolated, e.g., using Lymphoprep (Nycomed Pharma, Oslo, Norway) according to the manufacturer's recommended procedure.

As used herein, "isolating" placental stem cells means to remove at least 20%, 30%, 40%, 50%, 60%, 70%, 80%, 90%, 95% or 99% of the cells with which the stem cells are normally associated in the intact mammalian placenta. A stem cell from an organ is "isolated" when it is present in a population of cells that comprises fewer than 50% of the cells with which the stem cell is normally associated in the intact organ.

Placental cells obtained by perfusion or digestion can, for example, be further, or initially, isolated by differential trypsinization using, e.g., a solution of 0.05% trypsin with 0.2% EDTA (Sigma, St. Louis Mo.). Differential trypsinization is possible because placental stem cells typically detach from plastic surfaces within about five minutes whereas other adherent populations typically require more than 20-30 minutes incubation. The detached placental stem cells can be harvested following trypsinization and trypsin neutralization, using, e.g., Trypsin Neutralizing Solution (TNS, Cambrex). In one embodiment of isolation of adherent cells, aliquots of, for example, about $5\text{-}10 \times 10^6$ cells are placed in each of several T-75 flasks, preferably fibronectin-coated T75 flasks. In such an embodiment, the cells can be cultured with commercially available Mesenchymal Stem Cell Growth Medium (MSCGM) (Cambrex), and placed in a tissue culture incubator (37° C., 5% $CO_2$). After 10 to 15 days, non-adherent cells are removed from the flasks by washing with PBS. The PBS is then replaced by MSCGM. Flasks are preferably examined daily for the presence of various adherent cell types and in particular, for identification and expansion of clusters of fibroblastoid cells.

The number and type of cells collected from a mammalian placenta can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. For example, using antibodies to CD34, one can determine, using the techniques above, whether a cell comprises a detectable amount of CD34; if so, the cell is $CD34^+$. Likewise, if a cell produces enough OCT-4 RNA to be detectable by RT-PCR, or significantly more OCT-4 RNA than an adult cell, the cell is $OCT\text{-}4^+$ Antibodies to cell surface markers (e.g., CD markers such as CD34) and the sequence of stem cell-specific genes, such as OCT-4, are well-known in the art.

Placental cells, particularly cells that have been isolated by Ficoll separation, differential adherence, or a combination of both, may be sorted using a fluorescence activated cell sorter (FACS). Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In one sorting scheme, stem cells from placenta are sorted on the basis of expression of the markers CD34, CD38, CD44, CD45, CD73, CD105, OCT-4 and/or HLA-G. This can be accomplished in connection with procedures to select stem cells on the basis of their adherence properties in culture. For example, an adherence selection stem can be accomplished before or after sorting on the basis of marker expression. In one embodiment, for example, cells are sorted first on the basis of their expression of CD34; $CD34^-$ cells are retained, and cells that are $CD200^+HLA\text{-}G^+$, are separated from all other $CD34^-$ cells. In another embodiment, cells from placenta are based on their expression of markers CD200 and/or HLA-G; for example, cells displaying either of these markers are isolated for further use. Cells that express, e.g., CD200 and/or HLA-G can, in a specific embodiment, be further sorted based on their expression of CD73 and/or CD105, or epitopes recognized by antibodies SH2, SH3 or SH4, or lack of expression of CD34, CD38 or CD45. For example, in one embodiment, placental cells are sorted by expression, or lack thereof, of CD200, HLA-G, CD73, CD105, CD34, CD38 and CD45, and placental cells that are $CD200^+$, $HLA\text{-}G^+$, $CD73^+$, $CD105^+$, $CD34^-$, $CD38^-$ and $CD45^-$ are isolated from other placental cells for further use.

With respect to antibody-mediated detection and sorting of placental stem cells, any antibody, specific for a particular marker, can be used, in combination with any fluorophore or other label suitable for the detection and sorting of cells (e.g., fluorescence-activated cell sorting). Antibody/fluorophore combinations to specific markers include, but are not limited to, fluorescein isothiocyanate (FITC) conjugated monoclonal antibodies against HLA-G (available from Serotec, Raleigh, N.C.), CD10 (available from BD Immunocytometry Systems, San Jose, Calif.), CD44 (available from BD Biosciences Pharmingen, San Jose, Calif.), and CD105 (available from R&D Systems Inc., Minneapolis, Minn.); phycoerythrin (PE) conjugated monoclonal antibodies against CD44, CD200, CD117, and CD13 (BD Biosciences Pharmingen); phycoerythrin-Cy7 (PE Cy7) conjugated monoclonal antibodies against CD33 and CD10 (BD Biosciences Pharmingen); allophycocyanin (APC) conjugated streptavidin and monoclonal antibodies against CD38 (BD Biosciences Pharmingen); and Biotinylated CD90 (BD Biosciences Pharmingen). Other antibodies that can be used include, but are not limited to, CD133-APC (Miltenyi), KDR-Biotin (CD309, Abcam), CytokeratinK-Fitc (Sigma or Dako), HLA ABC-Fitc (BD), HLA DRDQDP-PE (BD), β-2-microglobulin-PE (BD), CD80-PE (BD) and CD86-APC (BD).

Other antibody/label combinations that can be used include, but are not limited to, CD45-PerCP (peridin chlorophyll protein); CD44-PE; CD19-PE; CD10-F (fluorescein); HLA-G-F and 7-amino-actinomycin-D (7-AAD); HLA-ABC-F; and the like.

Placental stem cells can be assayed for CD117 or CD133 using, for example, phycoerythrin-Cy5 (PE Cy5) conjugated streptavidin and biotin conjugated monoclonal antibodies against CD117 or CD133; however, using this system, the cells can appear to be positive for CD117 or CD133, respectively, because of a relatively high background.

Placental stem cells can be labeled with an antibody to a single marker and detected and/or sorted. Placental stem cells can also be simultaneously labeled with multiple antibodies to different markers.

In another embodiment, magnetic beads can be used to separate cells. The cells may be sorted using a magnetic activated cell sorting (MACS) technique, a method for separating particles based on their ability to bind magnetic beads (0.5-100 μm diameter). A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

Placental stem cells can also be characterized and/or sorted based on cell morphology and growth characteristics. For example, placental stem cells can be characterized as having, and/or selected on the basis of, e.g., a fibroblastoid appearance in culture. Placental stem cells can also be characterized as having, and/or be selected, on the basis of their ability to form embryoid-like bodies. In one embodiment, for example, placental cells that are fibroblastoid in shape, express CD73 and CD105, and produce one or more embryoid-like bodies in culture are isolated from other placental cells. In another embodiment, OCT-4$^+$ placental cells that produce one or more embryoid-like bodies in culture are isolated from other placental cells.

In another embodiment, placental stem cells can be identified and characterized by a colony forming unit assay. Colony forming unit assays are commonly known in the art, such as MESEN CULT™ medium (Stem Cell Technologies, Inc., Vancouver British Columbia)

Placental stem cells can be assessed for viability, proliferation potential, and longevity using standard techniques known in the art, such as trypan blue exclusion assay, fluorescein diacetate uptake assay, propidium iodide uptake assay (to assess viability); and thymidine uptake assay, MTT cell proliferation assay (to assess proliferation). Longevity may be determined by methods well known in the art, such as by determining the maximum number of population doubling in an extended culture.

Placental stem cells can also be separated from other placental cells using other techniques known in the art, e.g., selective growth of desired cells (positive selection), selective destruction of unwanted cells (negative selection); separation based upon differential cell agglutinability in the mixed population as, for example, with soybean agglutinin; freeze-thaw procedures; filtration; conventional and zonal centrifugation; centrifugal elutriation (counter-streaming centrifugation); unit gravity separation; countercurrent distribution; electrophoresis; and the like.

5.3 Culture of Placental Stem Cells

5.3.1 Culture Media

Isolated placental stem cells, or placental stem cell population, or cells or placental tissue from which placental stem cells grow out, can be used to initiate, or seed, cell cultures. Cells are generally transferred to sterile tissue culture vessels either uncoated or coated with extracellular matrix or ligands such as laminin, collagen (e.g., native or denatured), gelatin, fibronectin, ornithine, vitronectin, and extracellular membrane protein (e.g., MATRIGEL® (BD Discovery Labware, Bedford, Mass.)).

Placental stem cells can be cultured in any medium, and under any conditions, recognized in the art as acceptable for the culture of stem cells. Preferably, the culture medium comprises serum. Placental stem cells can be cultured in, for example, DMEM-LG (Dulbecco's Modified Essential Medium, low glucose)/MCDB 201 (chick fibroblast basal medium) containing ITS (insulin-transferrin-selenium), LA+BSA (linoleic acid-bovine serum albumin), dextrose, L-ascorbic acid, PDGF, EGF, IGF-1, and penicillin/streptomycin; DMEM-HG (high glucose) comprising 10% fetal bovine serum (FBS); DMEM-HG comprising 15% FBS; IMDM (Iscove's modified Dulbecco's medium) comprising 10% FBS, 10% horse serum, and hydrocortisone; M199 comprising 10% FBS, EGF, and heparin; α-MEM (minimal essential medium) comprising 10% FBS, GLUTAMAX and gentamicin; DMEM comprising 10% FBS, GLUTAMAX and gentamicin, etc. A preferred medium is DMEM-LG/MCDB-201 comprising 2% FBS, ITS, LA+BSA, dextrose, L-ascorbic acid, PDGF, EGF, and penicillin/streptomycin.

Other media in that can be used to culture placental stem cells include DMEM (high or low glucose), Eagle's basal medium, Ham's F10 medium (F10), Ham's F-12 medium (F12), Iscove's modified Dulbecco's medium, Mesenchymal Stem Cell Growth Medium (MSCGM), Liebovitz's L-15 medium, MCDB, DMEM/F12, RPMI 1640, advanced DMEM (Gibco), DMEM/MCDB201 (Sigma), and CELLGRO FREE.

The culture medium can be supplemented with one or more components including, for example, serum (e.g., fetal bovine serum (FBS), preferably about 2-15% (v/v); equine (horse) serum (ES); human serum (HS)); beta-mercaptoethanol (BME), preferably about 0.001% (v/v); one or more growth factors, for example, platelet-derived growth factor (PDGF), epidermal growth factor (EGF), basic fibroblast growth factor (bFGF), insulin-like growth factor-1 (IGF-1), leukemia inhibitory factor (LIF), vascular endothelial growth factor (VEGF), and erythropoietin (EPO); amino acids, including L-valine; and one or more antibiotic and/or antimycotic agents to control microbial contamination, such as, for example, penicillin G, streptomycin sulfate, amphotericin B, gentamicin, and nystatin, either alone or in combination.

Placental stem cells can be cultured in standard tissue culture conditions, e.g., in tissue culture dishes or multiwell plates. Placental stem cells can also be cultured using a hanging drop method. In this method, placental stem cells are suspended at about 1×10$^4$ cells per mL in about 5 mL of medium, and one or more drops of the medium are placed on the inside of the lid of a tissue culture container, e.g., a 100 mL Petri dish. The drops can be, e.g., single drops, or multiple drops from, e.g., a multichannel pipetter. The lid is carefully inverted and placed on top of the bottom of the dish, which contains a volume of liquid, e.g., sterile PBS sufficient to maintain the moisture content in the dish atmosphere, and the stem cells are cultured.

In one embodiment, the placental stem cells are cultured in the presence of a compound that acts to maintain an undifferentiated phenotype in the placental stem cell. In a specific embodiment, the compound is a substituted 3,4-dihydropyridimol[4,5-d]pyrimidine. In a more specific embodiment, the compound is a compound having the following chemical structure:

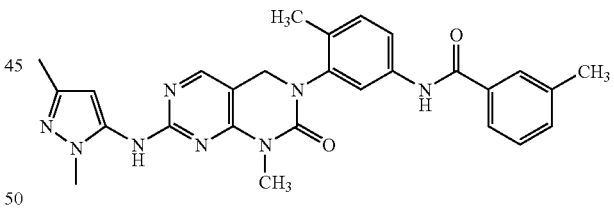

The compound can be contacted with a placental stem cell, or population of placental stem cells, at a concentration of, for example, between about 1 µM to about 10 µM.

5.3.2 Expansion and Proliferation of Placental Stem Cells

Once an isolated placental stem cell, or isolated population of stem cells (e.g., a stem cell or population of stem cells separated from at least 50% of the placental cells with which the stem cell or population of stem cells is normally associated in vivo), the stem cell or population of stem cells can be proliferated and expanded in vitro. For example, a population of placental stem cells can be cultured in tissue culture containers, e.g., dishes, flasks, multiwell plates, or the like, for a sufficient time for the stem cells to proliferate to 70-90% confluence, that is, until the stem cells and their progeny occupy 70-90% of the culturing surface area of the tissue culture container.

Placental stem cells can be seeded in culture vessels at a density that allows cell growth. For example, the cells may be seeded at low density (e.g., about 1,000 to about 5,000 cells/cm$^2$) to high density (e.g., about 50,000 or more cells/cm$^2$). In a preferred embodiment, the cells are cultured at about 0 to about 5 percent by volume $CO_2$ in air. In some preferred embodiments, the cells are cultured at about 2 to about 25 percent $O_2$ in air, preferably about 5 to about 20 percent $O_2$ in air. The cells preferably are cultured at about 25° C. to about 40° C., preferably 37° C. The cells are preferably cultured in an incubator. The culture medium can be static or agitated, for example, using a bioreactor. Placental stem cells preferably are grown under low oxidative stress (e.g., with addition of glutathione, ascorbic acid, catalase, tocopherol, N-acetylcysteine, or the like).

Once 70%-90% confluence is obtained, the cells may be passaged. For example, the cells can be enzymatically treated, e.g., trypsinized, using techniques well-known in the art, to separate them from the tissue culture surface. After removing the cells by pipetting and counting the cells, about 20,000-100,000 stem cells, preferably about 50,000 stem cells, are passaged to a new culture container containing fresh culture medium. Typically, the new medium is the same type of medium from which the stem cells were removed. The invention encompasses populations of placental stem cells that have been passaged at least 1, 2, 3, 4, 5, 6, 7, 8, 9, 10, 12, 14, 16, 18, or 20 times, or more.

5.3.3 Placental Stem Cell Populations

The invention provides populations of placental stem cells. Placental stem cell population can be isolated directly from one or more placentas; that is, the placental stem cell population can be a population of placental cells comprising placental stem cells obtained from, or contained within, perfusate, or obtained from, or contained within, disrupted placental tissue, e.g., placental tissue digestate (that is, the collection of cells obtained by enzymatic digestion of a placenta or part thereof). Isolated placental stem cells of the invention can also be cultured and expanded to produce placental stem cell populations. Populations of placental cells comprising placental stem cells can also be cultured and expanded to produce placental stem cell populations.

Placental stem cell populations of the invention comprise placental stem cells, for example, placental stem cells as described herein. In various embodiments, at least 10%, 20%, 30%, 40%, 50%, 60%, 70%, 80%, 90%, 95%, or 99% of the cells in an isolated placental stem cell population are placental stem cells. That is, a placental stem cell population can comprise, e.g., as much as 1%, 5%, 10%, 20%, 30%, 40%, 50%, 60%, 70%, 80%, 90% non-stem cells.

The invention provides methods of producing isolated placental stem cell population by, e.g., selecting placental stem cells, whether derived from enzymatic digestion or perfusion, that express particular markers and/or particular culture or morphological characteristics. In one embodiment, for example, the invention provides a method of producing a cell population comprising selecting placental cells that (a) adhere to a substrate, and (b) express CD200 and HLA-G; and isolating said cells from other cells to form a cell population. In another embodiment, the invention provides a method of producing a cell population comprising identifying placental cells that express CD200 and HLA-G, and isolating said cells from other cells to form a cell population. In another embodiment, the method of producing a cell population comprises selecting placental cells that (a) adhere to a substrate, and (b) express CD73, CD105, and CD200; and isolating said cells from other cells to form a cell population. In another embodiment, the invention provides a method of producing a cell population comprising identifying placental cells that express CD73, CD105, and CD200, and isolating said cells from other cells to form a cell population. In another embodiment, the method of producing a cell population comprises selecting placental cells that (a) adhere to a substrate and (b) express CD200 and OCT-4; and isolating said cells from other cells to form a cell population. In another embodiment, the invention provides a method of producing a cell population comprising identifying placental cells that express CD200 and OCT-4, and isolating said cells from other cells to form a cell population. In another embodiment, the method of producing a cell population comprises selecting placental cells that (a) adhere to a substrate, (b) express CD73 and CD105, and (c) facilitate the formation of one or more embryoid-like bodies in a population of placental cells comprising said stem cell when said population is cultured under conditions that allow for the formation of an embryoid-like body; and isolating said cells from other cells to form a cell population. In another embodiment, the invention provides a method of producing a cell population comprising identifying placental cells that express CD73 and CD105, and facilitate the formation of one or more embryoid-like bodies in a population of placental cells comprising said stem cell when said population is cultured under conditions that allow for the formation of an embryoid-like body, and isolating said cells from other cells to form a cell population. In another embodiment, the method of producing a cell population comprises selecting placental cells that (a) adhere to a substrate, and (b) express CD73, CD105 and HLA-G; and isolating said cells from other cells to form a cell population. In another embodiment, the invention provides a method of producing a cell population comprising identifying placental cells that express CD73, CD105 and HLA-G, and isolating said cells from other cells to form a cell population. In another embodiment, the method of producing a cell population comprises selecting placental cells that (a) adhere to a substrate, (b) express OCT-4, and (c) facilitate the formation of one or more embryoid-like bodies in a population of placental cells comprising said stem cell when said population is cultured under conditions that allow for the formation of an embryoid-like body; and isolating said cells from other cells to form a cell population. In another embodiment, the invention provides a method of producing a cell population comprising identifying placental cells that express OCT-4, and facilitate the formation of one or more embryoid-like bodies in a population of placental cells comprising said stem cell when said population is cultured under conditions that allow for the formation of an embryoid-like body, and isolating said cells from other cells to form a cell population.

Such cell populations can be used to treat any of the diseases or conditions listed hereinbelow. Such cell populations can also be used to assess populations of placental stem cells, e.g., as part of a quality control method.

In any of the above embodiments, the method can additionally comprise selecting placental cells that express ABC-p (a placenta-specific ABC transporter protein; see, e.g., Allikmets et al., *Cancer Res.* 58(23):5337-9 (1998)). The method can also comprise selecting cells exhibiting at least one characteristic specific to, e.g., a mesenchymal stem cell, for example, expression of CD29, expression of CD44, expression of CD90, or expression of a combination of the foregoing.

In the above embodiments, the substrate can be any surface on which culture and/or selection of cells, e.g., placental stem cells, can be accomplished. Typically, the substrate is plastic, e.g., tissue culture dish or multiwell plate plastic. Tissue culture plastic can be coated with a biomolecule, e.g., laminin or fibronectin.

Cells, e.g., placental stem cells, can be selected for a placental stem cell population by any means known in the art of cell selection. For example, cells can be selected using an antibody or antibodies to one or more cell surface markers, for example, in flow cytometry or FACS. Selection can be accomplished using antibodies in conjunction with magnetic beads. Antibodies that are specific for certain stem cell-related markers are known in the art. For example, antibodies to OCT-4 (Abcam, Cambridge, Mass.), CD200 (Abcam), HLA-G (Abcam), CD73 (BD Biosciences Pharmingen, San Diego, Calif.), CD105 (Abcam; BioDesign International, Saco, Me.), etc. Antibodies to other markers are also available commercially, e.g., CD34, CD38 and CD45 are available from, e.g., StemCell Technologies or BioDesign International.

The isolated placental stem cell population can comprise placental cells that are not stem cells, or cells that are not placental cells.

Isolated placental stem cell populations can be combined with one or more populations of non-stem cells or non-placental cells. For example, an isolated population of placental stem cells can be combined with blood (e.g., placental blood or umbilical cord blood), blood-derived stem cells (e.g., stem cells derived from placental blood or umbilical cord blood), umbilical cord stem cells, populations of blood-derived nucleated cells, bone marrow-derived mesenchymal cells, bone-derived stem cell populations, crude bone marrow, adult (somatic) stem cells, populations of stem cells contained within tissue, cultured stem cells, populations of fully-differentiated cells (e.g., chondrocytes, fibroblasts, amniotic cells, osteoblasts, muscle cells, cardiac cells, etc.) and the like. In a specific embodiment, the invention provides a population of stem cells comprising placental stem cells and umbilical cord stem cells. Cells in an isolated placental stem cell population can be combined with a plurality of cells of another type in ratios of about 100,000,000:1, 50,000,000:1, 20,000,000:1, 10,000,000:1, 5,000,000:1, 2,000,000:1, 1,000,000:1, 500,000:1, 200,000:1, 100,000:1, 50,000:1, 20,000:1, 10,000:1, 5,000:1, 2,000:1, 1,000:1, 500:1, 200:1, 100:1, 50:1, 20:1, 10:1, 5:1, 2:1, 1:1; 1:2; 1:5; 1:10; 1:100; 1:200; 1:500; 1:1,000; 1:2,000; 1:5,000; 1:10,000; 1:20,000; 1:50,000; 1:100,000; 1:500,000; 1:1,000,000; 1:2,000,000; 1:5,000,000; 1:10,000,000; 1:20,000,000; 1:50,000,000; or about 1:100,000,000, comparing numbers of total nucleated cells in each population. Cells in an isolated placental stem cell population can be combined with a plurality of cells of a plurality of cell types, as well.

In one, an isolated population of placental stem cells is combined with a plurality of hematopoietic stem cells. Such hematopoietic stem cells can be, for example, contained within unprocessed placental, umbilical cord blood or peripheral blood; in total nucleated cells from placental blood, umbilical cord blood or peripheral blood; in an isolated population of $CD34^+$ cells from placental blood, umbilical cord blood or peripheral blood; in unprocessed bone marrow; in total nucleated cells from bone marrow; in an isolated population of $CD34^+$ cells from bone marrow, or the like.

5.4 Production of a Placental Stem Cell Bank

Stem cells from postpartum placentas can be cultured in a number of different ways to produce a set of lots, e.g., a set of individually-administrable doses, of placental stem cells. Such lots can, for example, be obtained from stem cells from placental perfusate or from enzyme-digested placental tissue. Sets of lots of placental stem cells, obtained from a plurality of placentas, can be arranged in a bank of placental stem cells for, e.g., long-term storage. Generally, adherent stem cells are obtained from an initial culture of placental material to form a seed culture, which is expanded under controlled conditions to form populations of cells from approximately equivalent numbers of doublings. Lots are preferably derived from the tissue of a single placenta, but can be derived from the tissue of a plurality of placentas.

In one embodiment, stem cell lots are obtained as follows. Placental tissue is first disrupted, e.g., by mincing, digested with a suitable enzyme, e.g., collagenase (see Section 5.2.3, above). The placental tissue preferably comprises, e.g., the entire amnion, entire chorion, or both, from a single placenta, but can comprise only a part of either the amnion or chorion. The digested tissue is cultured, e.g., for about 1-3 weeks, preferably about 2 weeks. After removal of non-adherent cells, high-density colonies that form are collected, e.g., by trypsinization. These cells are collected and resuspended in a convenient volume of culture medium, and defined as Passage 0 cells.

Passage 0 cells are then used to seed expansion cultures. Expansion cultures can be any arrangement of separate cell culture apparatuses, e.g., a Cell Factory by NUNC™. Cells in the Passage 0 culture can be subdivided to any degree so as to seed expansion cultures with, e.g., $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $1\times10^4$, $2\times10^4$, $3\times10^4$, $4\times10^4$, $5\times10^4$, $6\times10^4$, $7\times10^4$, $8\times10^4$, $9\times10^4$, or $10\times10^4$ stem cells. Preferably, from about $2\times10^4$ to about $3\times10^4$ Passage 0 cells are used to seed each expansion culture. The number of expansion cultures can depend upon the number of Passage 0 cells, and may be greater or fewer in number depending upon the particular placenta(s) from which the stem cells are obtained.

Expansion cultures are grown until the density of cells in culture reaches a certain value, e.g., about $1\times10^5$ cells/cm$^2$. Cells can either be collected and cryopreserved at this point, or passaged into new expansion cultures as described above. Cells can be passaged, e.g., 2, 3, 4, 5, 6, 7, 8, 9, 10, 11, 12, 13, 14, 15, 16, 17, 18, 19 or 20 times prior to use. A record of the cumulative number of population doublings is preferably maintained during expansion culture(s). The cells from a Passage 0 culture can be expanded for 2, 3, 4, 5, 6, 7, 8, 9, 10, 12, 14, 16, 18, 20, 22, 24, 26, 28, 30, 32, 34, 36, 38 or 40 doublings, or up to 60 doublings. Preferably, however, the number of population doublings, prior to dividing the population of cells into individual doses, is between about 15 and about 30, preferably about 20 doublings. The cells can be culture continuously throughout the expansion process, or can be frozen at one or more points during expansion.

Cells to be used for individual doses can be frozen, e.g., cryopreserved for later use. Individual doses can comprise, e.g., about 1 million to about 100 million cells per ml, and can comprise between about $10^6$ and about $10^9$ cells in total.

In a specific embodiment, of the method, Passage 0 cells are cultured for a first number of doublings, e.g., approximately 4 doublings, then frozen in a first cell bank. Cells from the first cell bank are frozen and used to seed a second cell bank, the cells of which are expanded for a second number of doublings, e.g., about another eight doublings. Cells at this stage are collected and frozen and used to seed new expansion cultures that are allowed to proceed for a third number of doublings, e.g., about eight additional doublings, bringing the cumulative number of cell doublings to about 20. Cells at the intermediate points in passaging can be frozen in units of about 100,000 to about 10 million cells per ml, preferably about 1 million cells per ml for use in subsequent expansion culture. Cells at about 20 doublings can be frozen in individual doses of between about 1 million to about 100 million cells per ml for administration or use in making a stem cell-containing composition.

In one embodiment, therefore, the invention provides a method of making a placental stem cell bank, comprising: expanding primary culture placental stem cells from a human post-partum placenta for a first plurality of population doublings; cryopreserving said placental stem cells to form a Master Cell Bank; expanding a plurality of placental stem cells from the Master Cell Bank for a second plurality of population doublings; cryopreserving said placental stem cells to form a Working Cell Bank; expanding a plurality of placental stem cells from the Working Cell Bank for a third plurality of population doublings; and cryopreserving said placental stem cells in individual doses, wherein said individual doses collectively compose a placental stem cell bank. In a specific embodiment, the total number of population doublings is about 20. In another specific embodiment, said first plurality of population doublings is about four population doublings; said second plurality of population doublings is about eight population doublings; and said third plurality of population doublings is about eight population doublings. In another specific embodiment, said primary culture placental stem cells comprise placental stem cells from placental perfusate. In another specific embodiment, said primary culture placental stem cells comprise placental stem cells from digested placental tissue. In another specific embodiment, said primary culture placental stem cells comprise placental stem cells from placental perfusate and from digested placental tissue. In another specific embodiment, all of said placental stem cells in said placental stem cell primary culture are from the same placenta. In another specific embodiment, the method further comprises the step of selecting CD200$^+$ or HLA-G$^+$ placental stem cells from said plurality of said placental stem cells from said Working Cell Bank to form individual doses. In another specific embodiment, said individual doses comprise from about $10^4$ to about $10^5$ placental stem cells. In another specific embodiment, said individual doses comprise from about $10^5$ to about $10^6$ placental stem cells. In another specific embodiment, said individual doses comprise from about $10^6$ to about $10^7$ placental stem cells. In another specific embodiment, said individual doses comprise from about $10^7$ to about $10^8$ placental stem cells.

In a preferred embodiment, the donor from which the placenta is obtained (e.g., the mother) is tested for at least one pathogen. If the mother tests positive for a tested pathogen, the entire lot from the placenta is discarded. Such testing can be performed at any time during production of placental stem cell lots, including before or after establishment of Passage 0 cells, or during expansion culture. Pathogens for which the presence is tested can include, without limitation, hepatitis A, hepatitis B, hepatitis C, hepatitis D, hepatitis E, human immunodeficiency virus (types I and II), cytomegalovirus, herpesvirus, and the like.

5.5 Differentiation of Placental Stem Cells 5.5.1 Induction of Differentiation into Neuronal or Neurogenic Cells Neuronal differentiation of placental stem cells can be accomplished, for example, by placing placental stem cells in cell culture conditions that induce differentiation into neurons. In an example method, a neurogenic medium comprises DMEM/20% FBS and 1 mM beta-mercaptoethanol; such medium can be replaced after culture for about 24 hours with medium consisting of DMEM and 1-10 mM betamercaptoethanol. In another embodiment, the cells are contacted with DMEM/2% DMSO/200 µM butylated hydroxyanisole. In a specific embodiment, the differentiation medium comprises serum-free DMEMIF-12, butylated hydroxyanisole, potassium chloride, insulin, forskolin, valproic acid, and hydrocortisone. In another embodiment, neuronal differentiation is accomplished by plating placental stem cells on laminin-coated plates in Neurobasal-A medium (Invitrogen, Carlsbad Calif.) containing B27 supplement and L-glutamine, optionally supplemented with bFGF and/or EGF. Placental stem cells can also be induced to neural differentiation by co-culture with neural cells, or culture in neuron-conditioned medium.

Neuronal differentiation can be assessed, e.g., by detection of neuron-like morphology (e.g., bipolar cells comprising extended processes) detection of the expression of e.g., nerve growth factor receptor and neurofilament heavy chain genes by RT-PCR; or detection of electrical activity, e.g., by patch-clamp. A placental stem cell is considered to have differentiated into a neuronal cell when the cell displays one or more of these characteristics.

5.5.2 Induction of Differentiation into Adipogenic Cells

Adipogenic differentiation of placental stem cells can be accomplished, for example, by placing placental stem cells in cell culture conditions that induce differentiation into adipocytes. A preferred adipogenic medium comprises MSCGM (Cambrex) or DMEM supplemented with 15% cord blood serum. In one embodiment, placental stem cells are fed Adipogenesis Induction Medium (Cambrex) and cultured for 3 days (at 37° C., 5% $CO_2$), followed by 1-3 days of culture in Adipogenesis Maintenance Medium (Cambrex). After 3 complete cycles of induction/maintenance, the cells are cultured for an additional 7 days in adipogenesis maintenance medium, replacing the medium every 2-3 days.

In another embodiment, placental stem cells are cultured in medium comprising 1 µM dexamethasone, 0.2 mM indomethacin, 0.01 mg/ml insulin, 0.5 mM IBMX, DMEM-high glucose, FBS, and antibiotics. Placental stem cells can also be induced towards adipogenesis by culture in medium comprising one or more glucocorticoids (e.g., dexamethasone, indomethasone, hydrocortisone, cortisone), insulin, a compound which elevates intracellular levels of cAMP (e.g., dibutyryl-cAMP; 8-CPT-cAMP (8-(4)chlorophenylthio)-adenosine, 3',5' cyclic monophosphate); 8-bromo-cAMP; dioctanoyl-cAMP; forskolin) and/or a compound which inhibits degradation of cAMP (e.g., a phosphodiesterase inhibitor such as isobutylmethylxanthine (IBMX), methyl isobutylxanthine, theophylline, caffeine, indomethacin).

A hallmark of adipogenesis is the development of multiple intracytoplasmic lipid vesicles that can be easily observed using the lipophilic stain oil red O. Expression of lipase and/or fatty acid binding protein genes is confirmed by RT/PCR in placental stem cells that have begun to differentiate into adipocytes. A placental stem cell is considered to have differentiated into an adipocytic cell when the cell displays one or more of these characteristics.

5.5.3 Induction of Differentiation into Chondrocytic Cells

Chondrogenic differentiation of placental stem cells can be accomplished, for example, by placing placental stem cells in cell culture conditions that induce differentiation into chondrocytes. A preferred chondrocytic medium comprises MSCGM (Cambrex) or DMEM supplemented with 15% cord blood serum. In one embodiment, placental stem cells are aliquoted into a sterile polypropylene tube, centrifuged (e.g., at 150×g for 5 minutes), and washed twice in Incomplete Chondrogenesis Medium (Cambrex). The cells are resuspended in Complete Chondrogenesis Medium (Cambrex) containing 0.01 μg/ml TGF-beta-3 at a concentration of about $1\text{-}20\times10^5$ cells/ml. In other embodiments, placental stem cells are contacted with exogenous growth factors, e.g., GDF-5 or transforming growth factor beta3 (TGF-beta3), with or without ascorbate. Chondrogenic medium can be supplemented with amino acids including proline and glutamine, sodium pyruvate, dexamethasone, ascorbic acid, and insulin/transferrin/selenium. Chondrogenic medium can be supplemented with sodium hydroxide and/or collagen. The placental stem cells may be cultured at high or low density. Cells are preferably cultured in the absence of serum.

Chondrogenesis can be assessed by e.g., observation of production of esoinophilic ground substance, safranin-O staining for glycosaminoglycan expression; hematoxylin/eosin staining, assessing cell morphology, and/or RT/PCR confirmation of collagen 2 and collagen 9 gene expression. Chondrogenesis can also be observed by growing the stem cells in a pellet, formed, e.g., by gently centrifuging stem cells in suspension (e.g., at about 800 g for about 5 minutes). After about 1-28 days, the pellet of stem cells begins to form a tough matrix and demonstrates a structural integrity not found in non-induced, or non-chondrogenic, cell lines, pellets of which tend to fall apart when challenged. Chondrogenesis can also be demonstrated, e.g., in such cell pellets, by staining with a stain that stains collage, e.g., Sirius Red, and/or a stain that stains glycosaminoglycans (GAGs), such as, e.g., Alcian Blue. A placental stem cell is considered to have differentiated into a chondrocytic cell when the cell displays one or more of these characteristics.

5.5.4 Induction of Differentiation into Osteocytic Cells

Osteogenic differentiation of placental stem cells can be accomplished, for example, by placing placental stem cells in cell culture conditions that induce differentiation into osteocytes. A preferred osteocytic medium comprises MSCGM (Cambrex) or DMEM supplemented with 15% cord blood serum, followed by Osteogenic Induction Medium (Cambrex) containing 0.1 μM dexamethasone, 0.05 mM ascorbic acid-2-phosphate, 10 mM beta glycerophosphate. In another embodiment, placental stem cells are cultured in medium (e.g., DMEM-low glucose) containing about $10^{-7}$ to about $10^{-9}$ M dexamethasone, about 10-50 μM ascorbate phosphate salt (e.g., ascorbate-2-phosphate) and about 10 nM to about 10 mM β-glycerophosphate. Osteogenic medium can also include serum, one or more antibiotic/antimycotic agents, transforming growth factor-beta (e.g., TGF-β1) and/or bone morphogenic protein (e.g., BMP-2, BMP-4, or a combination thereof).

Differentiation can be assayed using a calcium-specific stain, e.g., von Kossa staining, and RT/PCR detection of, e.g., alkaline phosphatase, osteocalcin, bone sialoprotein and/or osteopontin gene expression. A placental stem cell is considered to have differentiated into an osteocytic cell when the cell displays one or more of these characteristics.

5.5.5 Induction of Differentiation into Pancreatic Cells

Differentiation of placental stem cells into insulin-producing pancreatic cells can be accomplished, for example, by placing placental stem cells in cell culture conditions that induce differentiation into pancreatic cells.

An example pancreagenic medium comprises DMEM/20% CBS, supplemented with basic fibroblast growth factor, 10 ng/ml; and transforming growth factor beta-1, 2 ng/ml. This medium is combined with conditioned media from nestin-positive neuronal cell cultures at 50/50 v/v. KnockOut Serum Replacement can be used in lieu of CBS. Cells are cultured for 14-28 days, refeeding every 3-4 days.

Differentiation can be confirmed by assaying for, e.g., insulin protein production, or insulin gene expression by RT/PCR. A placental stem cell is considered to have differentiated into a pancreatic cell when the cell displays one or more of these characteristics.

5.5.6 Induction of Differentiation into Cardiac Cells

Myogenic (cardiogenic) differentiation of placental stem cells can be accomplished, for example, by placing placental stem cells in cell culture conditions that induce differentiation into cardiomyocytes. A preferred cardiomyocytic medium comprises DMEM/20% CBS supplemented with retinoic acid, 1 μM; basic fibroblast growth factor, 10 ng/ml; and transforming growth factor beta-1, 2 ng/ml; and epidermal growth factor, 100 ng/ml. KnockOut Serum Replacement (Invitrogen, Carlsbad, Calif.) may be used in lieu of CBS. Alternatively, placental stem cells are cultured in DMEM/20% CBS supplemented with 50 ng/ml Cardiotropin-1 for 24 hours. In another embodiment, placental stem cells can be cultured 10-14 days in protein-free medium for 5-7 days, then stimulated with human myocardium extract, e.g., produced by homogenizing human myocardium in 1% HEPES buffer supplemented with 1% cord blood serum.

Differentiation can be confirmed by demonstration of cardiac actin gene expression, e.g., by RT/PCR, or by visible beating of the cell. A placental stem cell is considered to have differentiated into a cardiac cell when the cell displays one or more of these characteristics.

5.6 Preservation of Placental Stem Cells

Placental stem cells can be preserved, that is, placed under conditions that allow for long-term storage, or conditions that inhibit cell death by, e.g., apoptosis or necrosis.

Placental stem cells can be preserved using, e.g., a composition comprising an apoptosis inhibitor, necrosis inhibitor and/or an oxygen-carrying perfluorocarbon, as described in related U.S. Provisional Application No. 60/754,969, entitled "Improved Medium for Collecting Placental Stem Cells and Preserving Organs," filed on Dec. 25, 2005. In one embodiment, the invention provides a method of preserving a population of stem cells comprising contacting said population of stem cells with a stem cell collection composition comprising an inhibitor of apoptosis and an oxygen-carrying perfluorocarbon, wherein said inhibitor of apoptosis is present in an amount and for a time sufficient to reduce or prevent apoptosis in the population of stem cells, as compared to a population of stem cells not contacted with the inhibitor of apoptosis. In a specific embodiment, said inhibitor of apoptosis is a caspase inhibitor. In another specific embodiment, said inhibitor of apoptosis is a JNK inhibitor. In a more specific embodiment, said JNK inhibitor does not modulate differentiation or proliferation of said stem cells. In another embodiment, said stem cell collection composition comprises said inhibitor of apoptosis and said oxygen-carrying perfluorocarbon in separate phases. In another embodiment, said stem cell collection composition comprises said inhibitor of apoptosis and said oxygen-carrying perfluorocarbon in an emulsion. In another embodiment, the stem cell collection composition additionally comprises an emulsifier, e.g., lecithin. In another embodiment, said apoptosis inhibitor and said perfluorocarbon are between about 0° C. and about 25° C. at the time of contacting the stem cells. In another more specific embodiment, said apoptosis inhibitor and said perfluorocarbon are between about 2° C. and 10° C., or between about 2° C. and about 5° C., at the time of contacting the stem cells. In another more specific embodiment, said contacting is performed during transport of said population of stem cells. In another more specific embodiment, said contacting is performed during freezing and thawing of said population of stem cells.

In another embodiment, the invention provides a method of preserving a population of placental stem cells comprising contacting said population of stem cells with an inhibitor of apoptosis and an organ-preserving compound, wherein said inhibitor of apoptosis is present in an amount and for a time sufficient to reduce or prevent apoptosis in the population of stem cells, as compared to a population of stem cells not contacted with the inhibitor of apoptosis. In a specific embodiment, the organ-preserving compound is UW solution (described in U.S. Pat. No. 4,798,824; also known as ViaSpan; see also Southard et al., Transplantation 49(2):251-257 (1990)) or a solution described in Stern et al., U.S. Pat. No. 5,552,267. In another embodiment, said organ-preserving compound is hydroxyethyl starch, lactobionic acid, raffinose, or a combination thereof. In another embodiment, the stem cell collection composition additionally comprises an oxygen-carrying perfluorocarbon, either in two phases or as an emulsion.

In another embodiment of the method, placental stem cells are contacted with a stem cell collection composition comprising an apoptosis inhibitor and oxygen-carrying perfluorocarbon, organ-preserving compound, or combination thereof, during perfusion. In another embodiment, said stem cells are contacted during a process of tissue disruption, e.g., enzymatic digestion. In another embodiment, placental stem cells are contacted with said stem cell collection compound after collection by perfusion, or after collection by tissue disruption, e.g., enzymatic digestion.

Typically, during placental cell collection, enrichment and isolation, it is preferable to minimize or eliminate cell stress due to hypoxia and mechanical stress. In another embodiment of the method, therefore, a stem cell, or population of stem cells, is exposed to a hypoxic condition during collection, enrichment or isolation for less than six hours during said preservation, wherein a hypoxic condition is a concentration of oxygen that is less than normal blood oxygen concentration. In a more specific embodiment, said population of stem cells is exposed to said hypoxic condition for less than two hours during said preservation. In another more specific embodiment, said population of stem cells is exposed to said hypoxic condition for less than one hour, or less than thirty minutes, or is not exposed to a hypoxic condition, during collection, enrichment or isolation. In another specific embodiment, said population of stem cells is not exposed to shear stress during collection, enrichment or isolation.

The placental stem cells of the invention can be cryopreserved, e.g., in cryopreservation medium in small containers, e.g., ampoules. Suitable cryopreservation medium includes, but is not limited to, culture medium including, e.g., growth medium, or cell freezing medium, for example commercially available cell freezing medium, e.g., C2695, C2639 or C6039 (Sigma). Cryopreservation medium preferably comprises DMSO (dimethylsulfoxide), at a concentration of, e.g., about 10% (v/v). Cryopreservation medium may comprise additional agents, for example, methylcellulose and/or glycerol. Placental stem cells are preferably cooled at about 1° C./min during cryopreservation. A preferred cryopreservation temperature is about −80° C. to about −180° C., preferably about −125° C. to about −140° C. Cryopreserved cells can be transferred to liquid nitrogen prior to thawing for use. In some embodiments, for example, once the ampoules have reached about −90° C., they are transferred to a liquid nitrogen storage area. Cryopreservation can also be done using a controlled-rate freezer. Cryopreserved cells preferably are thawed at a temperature of about 25° C. to about 40° C., preferably to a temperature of about 37° C.

5.7 Uses of Placental Stem Cells

5.7.1 Placental Stem Cell Populations

Placental stem cell populations can be used to treat any disease, disorder or condition that is amenable to treatment by administration of a population of stem cells. As used herein, "treat" encompasses the cure of, remediation of, improvement of, lessening of the severity of, or reduction in the time course of, a disease, disorder or condition, or any parameter or symptom thereof.

Placental stem cells, and populations of placental stem cells, can be induced to differentiate into a particular cell type, either ex vivo or in vivo, in preparation for administration to an individual in need of stem cells, or cells differentiated from stem cells. For example, placental stem cells can be injected into a damaged organ, and for organ neogenesis and repair of injury in vivo. Such injury may be due to such conditions and disorders including, but not limited to, myocardial infarction, seizure disorder, multiple sclerosis, stroke, hypotension, cardiac arrest, ischemia, inflammation, thyroiditis, age-related loss of cognitive function, radiation damage, cerebral palsy, neurodegenerative disease, Alzheimer's disease, Parkinson's disease, Leigh disease, AIDS dementia, memory loss, amyotrophic lateral sclerosis, muscular dystrophy, ischemic renal disease, brain or spinal cord trauma, heart-lung bypass, glaucoma, retinal ischemia, or retinal trauma.

Placental stem cells can be used to treat autoimmune conditions such as juvenile diabetes, lupus, muscular dystrophy, rheumatoid arthritis, and the like.

Isolated populations of placental stem cells can be used, in specific embodiments, in autologous or heterologous enzyme replacement therapy to treat specific diseases or conditions, including, but not limited to lysosomal storage diseases, such as Tay-Sachs, Niemann-Pick, Fabry's, Gaucher's disease (e.g., glucocerbrosidase deficiency), Hunter's, and Hurler's syndromes, Maroteaux-Lamy syndrome, fucosidosis (fucosidase deficiency), Batten disease (CLN3), as well as other gangliosidoses, mucopolysaccharidoses, and glycogenoses.

Isolated populations of placental stem cells, alone or in combination with stem or progenitor cell populations, may be used alone, or as autologous or heterologous transgene carriers in gene therapy, to correct inborn errors of metabolism, cystic fibrosis, adrenoleukodystrophy (e.g., co-A ligase deficiency), metachromatic leukodystrophy (arylsulfatase A deficiency) (e.g., symptomatic, or presymptomatic late infantile or juvenile forms), globoid cell leukodystrophy (Krabbe's disease; galactocerebrosidase deficiency), acid lipase deficiency (Wolman disease), glycogen storage disease, hypothyroidism, anemia (e.g., aplastic anemia, sickle cell anemia, etc.), Pearson syndrome, Pompe's disease, phenylketonuria (PKU), porphyrias, maple syrup urine disease, homocystinuria, mucopolysaccharidenosis, chronic granulomatous disease and tyrosinemia and Tay-Sachs disease or to treat cancer (e.g., a hematologic malignancy), tumors or other pathological conditions. The placental stem cells can be used to treat skeletal dysplasia. In one embodiment, placental stem cells transformed to express tissue plasminogen activator (tPA) can be administered to an individual to treat thrombus.

In other embodiments, isolated populations of placental stem cells may be used in autologous or heterologous tissue regeneration or replacement therapies or protocols, including, but not limited to treatment of corneal epithelial defects, treatment of osteogenesis imperfecta, cartilage repair, facial dermabrasion, mucosal membranes, tympanic membranes, intestinal linings, neurological structures (e.g., retina, auditory neurons in basilar membrane, olfactory neurons in olfactory epithelium), burn and wound repair for traumatic injuries of the skin, or for reconstruction of other damaged or diseased organs or tissues.

In a preferred embodiment, an isolated population of placental stem cells is used in hematopoietic reconstitution in an individual that has suffered a partial or total loss of hematopoietic stem cells, e.g., individuals exposed to lethal or sublethal doses of radiation (whether industrial, medical or military); individuals that have undergone myeloablation as part of, e.g., cancer therapy, and the like, in the treatment of, e.g., a hematologic malignancy. Placental stem cells can be used in hematopoietic reconstitution in individuals having anemia (e.g., aplastic anemia, sickle cell anemia, etc.). Preferably, the placental stem cells are administered to such individuals with a population of hematopoietic stem cells. Isolated populations of placental-derived stem cells can be used in place of, or to supplement, bone marrow or populations of stem cells derived from bone marrow. Typically, approximately $1 \times 10^8$ to $2 \times 10^8$ bone marrow mononuclear cells per kilogram of patient weight are infused for engraftment in a bone marrow transplantation (i.e., about 70 ml of marrow for a 70 kg donor). To obtain 70 ml requires an intensive donation and significant loss of donor blood in the donation process. An isolated population of placental stem cells for hematopoietic reconstitution can comprise, in various embodiments, about, at least, or no more than $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$ or more placental stem cells.

In one embodiment, therefore, placental stem cells can be used to treat patients having a blood cancer, such as a lymphoma, leukemia (such as chronic or acute myelogenous leukemia, acute lymphocytic leukemia, Hodgkin's disease, etc.), myelodysplasia, myelodysplastic syndrome, and the like. In another embodiment, the disease, disorder or condition is chronic granulomatous disease.

Because hematopoietic reconstitution can be used in the treatment of anemias, the present invention further encompasses the treatment of an individual with a stem cell combination of the invention, wherein the individual has an anemia or disorder of the blood hemoglobin. The anemia or disorder may be natural (e.g., caused by genetics or disease), or may be artificially-induced (e.g., by accidental or deliberate poisoning, chemotherapy, and the like). In another embodiment, the disease or disorder is a marrow failure syndrome (e.g., aplastic anemia, Kostmann syndrome, Diamond-Blackfan anemia, amegakaryocytic thrombocytopenia, and the like), a bone marrow disorder or a hematopoietic disease or disorder.

Placental stem cells can also be used to treat severe combined immunodeficiency disease, including, but not limited to, combined immunodeficiency disease (e.g., Wiskott-Aldrich syndrome, severe DiGeorge syndrome, and the like).

The placental stem cells of the invention, alone or in combination with other stem cell or progenitor cell populations, can be used in the manufacture of a tissue or organ in vivo. The methods of the invention encompass using cells obtained from the placenta, e.g., stem cells or progenitor cells, to seed a matrix and to be cultured under the appropriate conditions to allow the cells to differentiate and populate the matrix. The tissues and organs obtained by the methods of the invention can be used for a variety of purposes, including research and therapeutic purposes.

In a preferred embodiment of the invention, placental stem cells and placental stem cell populations may be used for autologous and allogenic transplants, including matched and mismatched HLA type hematopoietic transplants. In one embodiment of the use of placental stem cells as allogenic hematopoietic transplants, the host is treated to reduce immunological rejection of the donor cells, or to create immunotolerance (see, e.g., U.S. Pat. Nos. 5,800,539 and 5,806,529). In another embodiment, the host is not treated to reduce immunological rejection or to create immunotolerance.

Placental stem cells, either alone or in combination with one or more other stem cell populations, can be used in therapeutic transplantation protocols, e.g., to augment or replace stem or progenitor cells of the liver, pancreas, kidney, lung, nervous system, muscular system, bone, bone marrow, thymus, spleen, mucosal tissue, gonads, or hair. Additionally, placental stem cells may be used instead of specific classes of progenitor cells (e.g., chondrocytes, hepatocytes, hematopoietic cells, pancreatic parenchymal cells, neuroblasts, muscle progenitor cells, etc.) in therapeutic or research protocols in which progenitor cells would typically be used.

In one embodiment, the invention provides for the use of placental stem cells, particularly $CD200^+$ placental stem cells, as an adjunct to hair replacement therapy. For example, in one embodiment, placental stem cells, e.g., $CD200^+$ placental stem cells, are injected subcutaneously or intradermally at a site in which hair growth or regrowth is desired. The number of stem cells injected can be, e.g., between about 100 and about 10,000 per injection, in a volume of about 0.1 to about 1.0 µL, though more ore fewer cells in a greater or lesser volume can also be used. Administration of placental stem cells to facilitate hair regrowth can comprise a single injection or multiple injections in, e.g., a regular or a random pattern in an area in which hair regrowth is desired. Known hair regrowth therapies can be used in conjunction with the placental stem cells, e.g., topical minoxidil. Hair loss that can be treated using placental stem cells can be naturally-occurring (e.g., male pattern baldness) or induced (e.g., resulting from toxic chemical exposure).

Placental stem cells and placental stem cell populations of the invention can be used for augmentation, repair or replacement of cartilage, tendon, or ligaments. For example, in certain embodiments, prostheses (e.g., hip prostheses) can be coated with replacement cartilage tissue constructs grown from placental stem cells of the invention. In other embodiments, joints (e.g., knee) can be reconstructed with cartilage tissue constructs grown from placental stem cells. Cartilage tissue constructs can also be employed in major reconstructive surgery for different types of joints (see, e.g., Resnick & Niwayama, eds., 1988, Diagnosis of Bone and Joint Disorders, 2d ed., W. B. Saunders Co.).

The placental stem cells of the invention can be used to repair damage to tissues and organs resulting from, e.g., trauma, metabolic disorders, or disease. The trauma can be, e.g., trauma from surgery, e.g., cosmetic surgery. In such an embodiment, a patient can be administered placental stem cells, alone or combined with other stem or progenitor cell populations, to regenerate or restore tissues or organs which have been damaged as a consequence of disease.

5.7.2 Compositions Comprising Placental Stem Cells

The present invention provides compositions comprising placental stem cells, or biomolecules therefrom. The placental stem cells of the present invention can be combined with any physiologically-acceptable or medically-acceptable compound, composition or device for use in, e.g., research or therapeutics.

5.7.2.1 Cryopreserved Placental Stem Cells

The placental stem cell populations of the invention can be preserved, for example, cryopreserved for later use. Methods for cryopreservation of cells, such as stem cells, are well known in the art. Placental stem cell populations can be prepared in a form that is easily administrable to an individual. For example, the invention provides a placental stem cell population that is contained within a container that is suitable for medical use. Such a container can be, for example, a sterile plastic bag, flask, jar, or other container from which the placental stem cell population can be easily dispensed. For example, the container can be a blood bag or other plastic, medically-acceptable bag suitable for the intravenous administration of a liquid to a recipient. The container is preferably one that allows for cryopreservation of the combined stem cell population.

The cryopreserved placental stem cell population can comprise placental stem cells derived from a single donor, or from multiple donors. The placental stem cell population can be completely HLA-matched to an intended recipient, or partially or completely HLA-mismatched.

Thus, in one embodiment, the invention provides a composition comprising a placental stem cell population in a container. In a specific embodiment, the stem cell population is cryopreserved. In another specific embodiment, the container is a bag, flask, or jar. In more specific embodiment, said bag is a sterile plastic bag. In a more specific embodiment, said bag is suitable for, allows or facilitates intravenous administration of said placental stem cell population. The bag can comprise multiple lumens or compartments that are interconnected to allow mixing of the placental stem cells and one or more other solutions, e.g., a drug, prior to, or during, administration. In another specific embodiment, the composition comprises one or more compounds that facilitate cryopreservation of the combined stem cell population. In another specific embodiment, said placental stem cell population is contained within a physiologically-acceptable aqueous solution. In a more specific embodiment, said physiologically-acceptable aqueous solution is a 0.9% NaCl solution. In another specific embodiment, said placental stem cell population comprises placental cells that are HLA-matched to a recipient of said stem cell population. In another specific embodiment, said combined stem cell population comprises placental cells that are at least partially HLA-mismatched to a recipient of said stem cell population. In another specific embodiment, said placental stem cells are derived from a plurality of donors.

5.7.2.2 Pharmaceutical Compositions

Populations of placental stem cells, or populations of cells comprising placental stem cells, can be formulated into pharmaceutical compositions for use in vivo. Such pharmaceutical compositions comprise a population of placental stem cells, or a population of cells comprising placental stem cells, in a pharmaceutically-acceptable carrier, e.g., a saline solution or other accepted physiologically-acceptable solution for in vivo administration. Pharmaceutical compositions of the invention can comprise any of the placental stem cell populations, or placental stem cell types, described elsewhere herein. The pharmaceutical compositions can comprise fetal, maternal, or both fetal and maternal placental stem cells. The pharmaceutical compositions of the invention can further comprise placental stem cells obtained from a single individual or placenta, or from a plurality of individuals or placentae.

The pharmaceutical compositions of the invention can comprise any number of placental stem cells. For example, a single unit dose of placental stem cells can comprise, in various embodiments, about, at least, or no more than $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more placental stem cells.

The pharmaceutical compositions of the invention comprise populations of cells that comprise 50% viable cells or more (that is, at least 50% of the cells in the population are functional or living). Preferably, at least 60% of the cells in the population are viable. More preferably, at least 70%, 80%, 90%, 95%, or 99% of the cells in the population in the pharmaceutical composition are viable.

The pharmaceutical compositions of the invention can comprise one or more compounds that, e.g., facilitate engraftment (e.g., anti-T-cell receptor antibodies, an immunosuppressant, or the like); stabilizers such as albumin, dextran 40, gelatin, hydroxyethyl starch, and the like.

When formulated as an injectable solution, in one embodiment, the pharmaceutical composition of the invention comprises about 1.25% HSA and about 2.5% dextran. Other injectable formulations, suitable for the administration of cellular products, may be used.

In one embodiment, the composition of the invention comprises placental stem cells that are substantially, or completely, non-maternal in origin. For example, the invention provides in one embodiment a composition comprising a population of placental stem cells that are $CD200^+$ and HLA-$G^+$; $CD73^+$, $CD105^+$, and $CD200^+$; $CD200^+$ and $OCT-4^+$; $CD73^+$, $CD105^+$ and HLA-$G^+$; $CD73^+$ and $CD105^+$ and facilitate the formation of one or more embryoid-like bodies in a population of placental cells comprising said population of placental stem cell when said population of placental cells is cultured under conditions that allow the formation of an embryoid-like body; or $OCT-4^+$ and facilitate the formation of one or more embryoid-like bodies in a population of placental cells comprising said population of placental stem cell when said population of placental cells is cultured under conditions that allow the formation of an embryoid-like body; or a combination of the foregoing, wherein at least 70%, 80%, 90%, 95% or 99% of said placental stem cells are non-maternal in origin. In a specific embodiment, the composition additionally comprises a stem cell that is not obtained from a placenta.

5.7.2.3 Placental Stem Cell Conditioned Media

The placental stem cells of the invention can be used to produce conditioned medium, that is, medium comprising one or more biomolecules secreted or excreted by the stem cells. In various embodiments, the conditioned medium comprises medium in which placental stem cells have grown for at least 1, 2, 3, 4, 5, 6, 7, 8, 9, 10, 11, 12, 13, 14 or more days. In other embodiments, the conditioned medium comprises medium in which placental stem cells have grown to at least 30%, 40%, 50%, 60%, 70%, 80%, 90% confluence, or up to 100% confluence. Such conditioned medium can be used to support the culture of a separate population of placental stem cells, or stem cells of another kind. In another embodiment, the conditioned medium comprises medium in which placental stem cells have been differentiated into an adult cell type. In another embodiment, the conditioned medium of the invention comprises medium in which placental stem cells and non-placental stem cells have been cultured.

5.7.2.4 Matrices Comprising Placental Stem Cells

The invention further comprises matrices, hydrogels, scaffolds, and the like that comprise a placental stem cell, or a population of placental stem cells.

Placental stem cells of the invention can be seeded onto a natural matrix, e.g., a placental biomaterial such as an amniotic membrane material. Such an amniotic membrane material can be, e.g., amniotic membrane dissected directly from a mammalian placenta; fixed or heat-treated amniotic membrane, substantially dry (i.e., <20% $H_2O$) amniotic membrane, chorionic membrane, substantially dry chorionic membrane, substantially dry amniotic and chorionic membrane, and the like. Preferred placental biomaterials on which placental stem cells can be seeded are described in Hariri, U.S. Application Publication No. 2004/0048796.

Placental stem cells of the invention can be suspended in a hydrogel solution suitable for, e.g., injection. Suitable hydrogels for such compositions include self-assembling peptides, such as RAD16. In one embodiment, a hydrogel solution comprising the cells can be allowed to harden, for instance in a mold, to form a matrix having cells dispersed therein for implantation. Placental stem cells in such a matrix can also be cultured so that the cells are mitotically expanded prior to implantation. The hydrogel is, e.g., an organic polymer (natural or synthetic) that is cross-linked via covalent, ionic, or hydrogen bonds to create a three-dimensional open-lattice structure that entraps water molecules to form a gel. Hydrogel-forming materials include polysaccharides such as alginate and salts thereof, peptides, polyphosphazines, and polyacrylates, which are crosslinked ionically, or block polymers such as polyethylene oxide-polypropylene glycol block copolymers which are crosslinked by temperature or pH, respectively. In some embodiments, the hydrogel or matrix of the invention is biodegradable.

In some embodiments of the invention, the formulation comprises an in situ polymerizable gel (see., e.g., U.S. Patent Application Publication 2002/0022676; Anseth et al., *J. Control Release*, 78(1-3):199-209 (2002); Wang et al., *Biomaterials*, 24(22):3969-80 (2003).

In some embodiments, the polymers are at least partially soluble in aqueous solutions, such as water, buffered salt solutions, or aqueous alcohol solutions, that have charged side groups, or a monovalent ionic salt thereof. Examples of polymers having acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

The placental stem cells of the invention or co-cultures thereof can be seeded onto a three-dimensional framework or scaffold and implanted in vivo. Such a framework can be implanted in combination with any one or more growth factors, cells, drugs or other components that stimulate tissue formation or otherwise enhance or improve the practice of the invention.

Examples of scaffolds that can be used in the present invention include nonwoven mats, porous foams, or self assembling peptides. Nonwoven mats can be formed using fibers comprised of a synthetic absorbable copolymer of glycolic and lactic acids (e.g., PGA/PLA) (VICRYL, Ethicon, Inc., Somerville, N.J.). Foams, composed of, e.g., poly(ε-caprolactone)/poly(glycolic acid) (PCL/PGA) copolymer, formed by processes such as freeze-drying, or lyophilization (see, e.g., U.S. Pat. No. 6,355,699), can also be used as scaffolds.

Placental stem cells of the invention can also be seeded onto, or contacted with, a physiologically-acceptable ceramic material including, but not limited to, mono-, di-, tri-, alpha-tri-, beta-tri-, and tetra-calcium phosphate, hydroxyapatite, fluoroapatites, calcium sulfates, calcium fluorides, calcium oxides, calcium carbonates, magnesium calcium phosphates, biologically active glasses such as BIOGLASS®, and mixtures thereof. Porous biocompatible ceramic materials currently commercially available include SURGIBONE® (Canmedica Corp., Canada), ENDOBON® (Merck Biomaterial France, France), CEROS® (Mathys, AG, Bettlach, Switzerland), and mineralized collagen bone grafting products such as HEALOS™ (DePuy, Inc., Raynham, Mass.) and VITOSS®, RHAKOSS™, and CORTOSS® (Orthovita, Malvern, Pa.). The framework can be a mixture, blend or composite of natural and/or synthetic materials.

In another embodiment, placental stem cells can be seeded onto, or contacted with, a felt, which can be, e.g., composed of a multifilament yarn made from a bioabsorbable material such as PGA, PLA, PCL copolymers or blends, or hyaluronic acid.

The placental stem cells of the invention can, in another embodiment, be seeded onto foam scaffolds that may be composite structures. Such foam scaffolds can be molded into a useful shape, such as that of a portion of a specific structure in the body to be repaired, replaced or augmented. In some embodiments, the framework is treated, e.g., with 0.1M acetic acid followed by incubation in polylysine, PBS, and/or collagen, prior to inoculation of the cells of the invention in order to enhance cell attachment. External surfaces of a matrix may be modified to improve the attachment or growth of cells and differentiation of tissue, such as by plasma-coating the matrix, or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate, etc.), a cellular matrix, and/or other materials such as, but not limited to, gelatin, alginates, agar, agarose, and plant gums, and the like.

In some embodiments, the scaffold comprises, or is treated with, materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as EPTFE, and segmented polyurethaneurea silicones, such as PURSPAN™ (The Polymer Technology Group, Inc., Berkeley, Calif.). The scaffold can also comprise anti-thrombotic agents such as heparin; the scaffolds can also be treated to alter the surface charge (e.g., coating with plasma) prior to seeding with placental stem cells.

5.7.3 Immortalized Placental Stem Cell Lines

Mammalian placental cells can be conditionally immortalized by transfection with any suitable vector containing a growth-promoting gene, that is, a gene encoding a protein that, under appropriate conditions, promotes growth of the transfected cell, such that the production and/or activity of the growth-promoting protein is regulatable by an external factor. In a preferred embodiment the growth-promoting gene is an oncogene such as, but not limited to, v-myc, N-myc, c-myc, p53, SV40 large T antigen, polyoma large T antigen, E1a adenovirus or E7 protein of human papillomavirus.

External regulation of the growth-promoting protein can be achieved by placing the growth-promoting gene under the control of an externally-regulatable promoter, e.g., a promoter the activity of which can be controlled by, for example, modifying the temperature of the transfected cells or the composition of the medium in contact with the cells. in one embodiment, a tetracycline (tet)-controlled gene expression system can be employed (see Gossen et al., *Proc. Natl. Acad. Sci. USA* 89:5547-5551, 1992; Hoshimaru et al., *Proc. Natl. Acad. Sci. USA* 93:1518-1523, 1996). In the absence of tet, a tet-controlled transactivator (tTA) within this vector strongly activates transcription from $ph_{CMV^{*}-1}$, a minimal promoter from human cytomegalovirus fused to tet operator sequences.

tTA is a fusion protein of the repressor (tetR) of the transposon-10-derived tet resistance operon of *Escherichia coli* and the acidic domain of VP16 of herpes simplex virus. Low, non-toxic concentrations of tet (e.g., 0.01-1.0 µg/mL) almost completely abolish transactivation by tTA.

In one embodiment, the vector further contains a gene encoding a selectable marker, e.g., a protein that confers drug resistance. The bacterial neomycin resistance gene (neo$^R$) is one such marker that may be employed within the present invention. Cells carrying neo$^R$ may be selected by means known to those of ordinary skill in the art, such as the addition of, e.g., 100-200 µg/mL G418 to the growth medium.

Transfection can be achieved by any of a variety of means known to those of ordinary skill in the art including, but not limited to, retroviral infection. In general, a cell culture may be transfected by incubation with a mixture of conditioned medium collected from the producer cell line for the vector and DMEM/F12 containing N2 supplements. For example, a placental cell culture prepared as described above may be infected after, e.g., five days in vitro by incubation for about 20 hours in one volume of conditioned medium and two volumes of DMEM/F12 containing N2 supplements. Transfected cells carrying a selectable marker may then be selected as described above.

Following transfection, cultures are passaged onto a surface that permits proliferation, e.g., allows at least 30% of the cells to double in a 24 hour period. Preferably, the substrate is a polyornithine/laminin substrate, consisting of tissue culture plastic coated with polyornithine (10 µg/mL) and/or laminin (10 µg/mL), a polylysine/laminin substrate or a surface treated with fibronectin. Cultures are then fed every 3-4 days with growth medium, which may or may not be supplemented with one or more proliferation-enhancing factors. Proliferation-enhancing factors may be added to the growth medium when cultures are less than 50% confluent.

The conditionally-immortalized placental stem cell lines can be passaged using standard techniques, such as by trypsinization, when 80-95% confluent. Up to approximately the twentieth passage, it is, in some embodiments, beneficial to maintain selection (by, for example, the addition of G418 for cells containing a neomycin resistance gene). Cells may also be frozen in liquid nitrogen for long-term storage.

Clonal cell lines can be isolated from a conditionally-immortalized human placental stem cell line prepared as described above. In general, such clonal cell lines may be isolated using standard techniques, such as by limit dilution or using cloning rings, and expanded. Clonal cell lines may generally be fed and passaged as described above.

Conditionally-immortalized human placental stem cell lines, which may, but need not be, clonal, may generally be induced to differentiate by suppressing the production and/or activity of the growth-promoting protein under culture conditions that facilitate differentiation. For example, if the gene encoding the growth-promoting protein is under the control of an externally-regulatable promoter, the conditions, e.g., temperature or composition of medium, may be modified to suppress transcription of the growth-promoting gene. For the tetracycline-controlled gene expression system discussed above, differentiation can be achieved by the addition of tetracycline to suppress transcription of the growth-promoting gene. In general, 1 µg/mL tetracycline for 4-5 days is sufficient to initiate differentiation. To promote further differentiation, additional agents may be included in the growth medium.

5.7.4 Assays

The placental stem cells for the present invention can be used in assays to determine the influence of culture conditions, environmental factors, molecules (e.g., biomolecules, small inorganic molecules. etc.) and the like on stem cell proliferation, expansion, and/or differentiation, compared to placental stem cells not exposed to such conditions.

In a preferred embodiment, the placental stem cells of the present invention are assayed for changes in proliferation, expansion or differentiation upon contact with a molecule. In one embodiment, for example, the invention provides a method of identifying a compound that modulates the proliferation of a plurality of placental stem cells, comprising contacting said plurality of stem cells with said compound under conditions that allow proliferation, wherein if said compound causes a detectable change in proliferation of said plurality of stem cells compared to a plurality of stem cells not contacted with said compound, said compound is identified as a compound that modulates proliferation of placental stem cells. In a specific embodiment, said compound is identified as an inhibitor of proliferation. In another specific embodiment, said compound is identified as an enhancer of proliferation.

In another embodiment, the invention provides a method of identifying a compound that modulates the expansion of a plurality of placental stem cells, comprising contacting said plurality of stem cells with said compound under conditions that allow expansion, wherein if said compound causes a detectable change in expansion of said plurality of stem cells compared to a plurality of stem cells not contacted with said compound, said compound is identified as a compound that modulates expansion of placental stem cells. In a specific embodiment, said compound is identified as an inhibitor of expansion. In another specific embodiment, said compound is identified as an enhancer of expansion.

In another embodiment, the invention provides a method of identifying a compound that modulates the differentiation of a placental stem cell, comprising contacting said stem cells with said compound under conditions that allow differentiation, wherein if said compound causes a detectable change in differentiation of said stem cells compared to a stem cell not contacted with said compound, said compound is identified as a compound that modulates proliferation of placental stem cells. In a specific embodiment, said compound is identified as an inhibitor of differentiation. In another specific embodiment, said compound is identified as an enhancer of differentiation.

6. EXAMPLES

6.1 Example 1

Culture of Placental Stem Cells

Placental stem cells are obtained from a post-partum mammalian placenta either by perfusion or by physical disruption, e.g., enzymatic digestion. The cells are cultured in a culture medium comprising 60% DMEM-LG (Gibco), 40% MCDB-201 (Sigma), 2% fetal calf serum (FCS) (Hyclone Laboratories), 1× insulin-transferrin-selenium (ITS), 1× lenolenic-acid-bovine-serum-albumin (LA-BSA), $10^{-9}$M dexamethasone (Sigma), $10^{-4}$M ascorbic acid 2-phosphate (Sigma), epidermal growth factor (EGF) 10 ng/ml (R&D Systems), platelet derived-growth factor (PDGF-BB) 10 ng/ml (R&D Systems), and 100 U penicillin/1000 U streptomycin.

The culture flask in which the cells are cultured is prepared as follows. T75 flasks are coated with fibronectin (FN), by adding 5 ml PBS containing 5 ng/ml human FN (Sigma F0895) to the flask. The flasks with FN solution are left at 37° C. for 30 min. The FN solution is then removed prior to cell culture. There is no need to dry the flasks following treatment. Alternatively, the flasks are left in contact with the FN solution at 4° C. overnight or longer; prior to culture, the flasks are warmed and the FN solution is removed.

Placental Stem Cells Isolated by Perfusion

Cultures of placental stem cells from placental perfusate are established as follows. Cells from a Ficoll gradient are seeded in FN-coated T75 flasks, prepared as above, at 50-100×10$^6$ cells/flask in 15 ml culture medium. Typically, 5 to 10 flasks are seeded. The flasks are incubated at 37° C. for 12-18 hrs to allow the attachment of adherent cells. 10 ml of warm PBS is added to each flask to remove cells in suspension, and mixed gently. 15 mL of the medium is then removed and replaced with 15 ml fresh culture medium. All medium is changed 3-4 days after the start of culture. Subsequent culture medium changes are performed, during which 50% or 7.5 ml of the medium is removed.

Starting at about day 12, the culture is checked under a microscope to examine the growth of the adherent cell colonies. When cell cultures become approximately 80% confluent, typically between day 13 to day 18 after the start of culture, adherent cells are harvested by trypsin digestion. Cells harvested from these primary cultures are designated passage 0 (zero).

Placental Stem Cells Isolated by Physical Disruption and Enzymatic Digestion

Placental stem cell cultures are established from digested placental tissue as follows. The perfused placenta is placed on a sterile paper sheet with the maternal side up. Approximately 0.5 cm of the surface layer on maternal side of placenta is scraped off with a blade, and the blade is used to remove a placental tissue block measuring approximately 1×2×1 cm. This placenta tissue is then minced into approximately 1 mm$^3$ pieces. These pieces are collected into a 50 ml Falcon tube and digested with collagenase IA (2 mg/ml, Sigma) for 30 minutes, followed by trypsin-EDTA (0.25%, GIBCO BRL) for 10 minutes, at 37° C. in water bath. The resulting solution is centrifuged at 400 g for 10 minutes at room temperature, and the digestion solution is removed. The pellet is resuspended to approximately 10 volumes with PBS (for example, a 5 ml pellet is resuspended with 45 ml PBS), and the tubes are centrifuged at 400 g for 10 minutes at room temperature. The tissue/cell pellet is resuspended in 130 mL culture medium, and the cells are seeded at 13 ml per fibronectin-coated T-75 flask. Cells are incubated at 37° C. with a humidified atmosphere with 5% $CO_2$. Placental Stem Cells are optionally cryopreserved at this stage.

Subculturing and Expansion of Placental Stem Cells

Cryopreserved cells are quickly thawed in a 37° C. water bath. Placental stem cells are immediately removed from the cryovial with 10 ml warm medium and transferred to a 15 ml sterile tube. The cells are centrifuged at 400 g for 10 minutes at room temperature. The cells are gently resuspended in 10 ml of warm culture medium by pipetting, and viable cell counts are determined by Trypan blue exclusion. Cells are then seeded at about 6000-7000 cells per cm$^2$ onto FN-coated flasks, prepared as above (approximately 5×10$^5$ cells per T-75 flask). The cells are incubated at 37° C., 5% $CO_2$ and 90% humidity. When the cells reached 75-85% confluency, all of the spent media is aseptically removed from the flasks and discarded. 3 ml of 0.25% trypsin/EDTA (w/v) solution is added to cover the cell layer, and the cells are incubated at 37° C., 5% $CO_2$ and 90% humidity for 5 minutes. The flask is tapped once or twice to expedite cell detachment. Once >95% of the cells are rounded and detached, 7 ml of warm culture medium is added to each T-75 flask, and the solution is dispersed by pipetting over the cell layer surface several times.

After counting the cells and determining viability as above, the cells are centrifuged at 1000 RPM for 5 minutes at room temperature. Cells are passaged by gently resuspending the cell pellet from one T-75 flask with culture medium, and evenly plating the cells onto two FN-coated T-75 flasks.

Using the above methods, exemplary populations of adherent placental stem cells are identified that express markers CD105, CD33, CD73, CD29, CD44, CD10, and CD90. These populations of cells typically does not express CD34, CD45, CD117 or CD133. Some, but not all cultures of these placental stem cells expressed HLA-ABC and/or HLA-DR.

6.2 Example 2

Isolation of Placental Stem Cells from Placental Structures 6.2.1 Materials & Methods 6.2.1.1 Isolation of Populations of Placental Cells Comprising Placental Stem Cells Distinct populations of placental cells were obtained from the placentas of normal, full-term pregnancies. All donors provided full written consent for the use of their placentas for research purposes. Placental stem cells were obtained from the following sources: (1) placental perfusate (from perfusion of the placental vasculature); and enzymatic digestions of (2) amnion, (3) chorion, (4) amnion-chorion plate, and (5) umbilical cord. The various placental tissues were cleaned in sterile PBS (Gibco-Invitrogen Corporation, Carlsbad, Calif.) and placed on separate sterile Petri dishes. The various tissues were minced using a sterile surgical scalpel and placed into 50 mL Falcon Conical tubes. The minced tissues were digested with 1× Collagenase (Sigma-Aldrich, St. Louis, Mo.) for 20 minutes in a 37° C. water bath, centrifuged, and then digested with 0.25% Trypsin-EDTA (Gibco-Invitrogen Corp) for 10 minutes in a 37° C. water bath. The various tissues were centrifuged after digestion and rinsed once with sterile PBS (Gibco-Invitrogen Corp). The reconstituted cells were then filtered twice, once with 100 μm cell strainers and once with 30 μm separation filters, to remove any residual extracellular matrix or cellular debris.

6.2.1.2 Cellular Viability Assessment and Cell Counts

The manual trypan blue exclusion method was employed post digestion to calculate cell counts and assess cellular viability. Cells were mixed with Trypan Blue Dye (Sigma-Aldrich) at a ratio of 1:1, and the cells were read on hemacytometer.

6.2.1.3 Cell Surface Marker Characterization

Cells that were HLA ABC$^-$/CD45$^-$/CD34$^-$/CD133$^+$ were selected for characterization. Cells having this phenotype were identified, quantified, and characterized by two of Becton-Dickinson flow cytometers, the FACSCalibur and the FACS Aria (Becton-Dickinson, San Jose, Calif., USA). The various placental cells were stained, at a ratio of about 10 μL of antibody per 1 million cells, for 30 minutes at room temperature on a shaker. The following anti-human antibodies were used: Fluorescein Isothiocyanate (FITC) conjugated monoclonal antibodies against HLA-G (Serotec, Raleigh, N.C.), CD10 (BD Immunocytometry Systems, San Jose, Calif.), CD44 (BD Biosciences Pharmingen, San Jose, Calif.), and CD105 (R&D Systems Inc., Minneapolis, Minn.); Phycoerythrin (PE) conjugated monoclonal antibodies against CD44, CD200, CD117, and CD13 (BD Biosciences Pharmingen); Phycoerythrin-Cy5 (PE Cy5) conjugated Streptavidin and monoclonal antibodies against CD117 (BD Biosciences Pharmingen); Phycoerythrin-Cy7 (PE Cy7) conjugated monoclonal antibodies against CD33 and CD10

(BD Biosciences); Allophycocyanin (APC) conjugated streptavidin and monoclonal antibodies against CD38 (BD Biosciences Pharmingen); and Biotinylated CD90 (BD Biosciences Pharmingen). After incubation, the cells were rinsed once to remove unbound antibodies and were fixed overnight with 4% paraformaldehyde (USB, Cleveland, Ohio) at 4° C. The following day, the cells were rinsed twice, filtered through a 30 μm separation filter, and were run on the flow cytometer(s).

Samples that were stained with anti-mouse IgG antibodies (BD Biosciences Pharmingen) were used as negative controls and were used to adjust the Photo Multiplier Tubes (PMTs). Samples that were single stained with anti-human antibodies were used as positive controls and were used to adjust spectral overlaps/compensations.

6.2.1.4 Cell Sorting and Culture

One set of placental cells (from perfusate, amnion, or chorion), prior to any culture, was stained with 7-Amino-Actinomycin D (7AAD; BD Biosciences Pharmingen) and monoclonal antibodies specific for the phenotype of interest. The cells were stained at a ratio of 10 μL of antibody per 1 million cells, and were incubated for 30 minutes at room temperature on a shaker. These cells were then positively sorted for live cells expressing the phenotype of interest on the BD FACS Aria and plated into culture. Sorted (population of interest) and "All" (non-sorted) placental cell populations were plated for comparisons. The cells were plated onto a fibronectin (Sigma-Aldrich) coated 96 well plate at the cell densities listed in Table 1 (cells/cm$^2$). The cell density, and whether the cell type was plated in duplicate or triplicate, was determined and governed by the number of cells expressing the phenotype of interest.

TABLE 1

Cell plating densities

| Conditions | Sorted | All | All Max. Density |
|---|---|---|---|
| Cell Source | | Perfusate | |
| Set #1: | 40.6 K/cm$^2$ | 40.6 K/cm$^2$ | 93.8 K/cm$^2$ |
| Set #2 | 40.6 K/cm$^2$ | 40.6 K/cm$^2$ | 93.8 K/cm$^2$ |
| Set #3: | 40.6 K/cm$^2$ | 40.6 K/cm$^2$ | 93.8 K/cm$^2$ |
| Cell Source | | Amnion | |
| Set #1: | 6.3 K/cm$^2$ | 6.3 K/cm$^2$ | 62.5 K/cm$^2$ |
| Set #2 | 6.3 K/cm$^2$ | 6.3 K/cm$^2$ | 62.5 K/cm$^2$ |
| Cell Source | | Chorion | |
| Set #1: | 6.3 K/cm$^2$ | 6.3 K/cm$^2$ | 62.5 K/cm$^2$ |
| Set #2 | 6.3 K/cm$^2$ | 6.3 K/cm$^2$ | 62.5 K/cm$^2$ |

Complete medium (60% DMEM-LG (Gibco) and 40% MCDB-201 (Sigma); 2% fetal calf serum (Hyclone Labs.); 1× insulin-transferrin-selenium (ITS); 1× linoleic acid-bovine serum albumin (LA-BSA); 10$^{-9}$ M dexamethasone (Sigma); 10$^{-4}$ M ascorbic acid 2-phosphate (Sigma); epidermal growth factor 10 ng/mL (R&D Systems); and platelet-derived growth factor (PDGF-BB) 10 ng/mL (R&D Systems)) was added to each well of the 96 well plate and the plate was placed in a 5% CO$_2$/37° C. incubator. On day 7, 100 μL of complete medium was added to each of the wells. The 96 well plate was monitored for about two weeks and a final assessment of the culture was completed on day 12. This is very early in the placental stem cell culture, and represents passage 0 cells.

6.2.1.5 Data Analysis

FACSCalibur data was analyzed in FlowJo (Tree star, Inc) using standard gating techniques. The BD FACS Aria data was analyzed using the FACSDiva software (Becton-Dickinson). The FACS Aria data was analyzed using doublet discrimination gating to minimize doublets, as well as, standard gating techniques. All results were compiled in Microsoft Excel and all values, herein, are represented as average±standard deviation (number, standard error of mean).

6.2.2 Results 6.2.2.1 Cellular Viability

Post-digestion viability was assessed using the manual trypan blue exclusion method (FIG. 1). The average viability of cells obtained from the majority of the digested tissue (from amnion, chorion or amnion-chorion plate) was around 70%. Amnion had an average viability of 74.35%±10.31% (n=6, SEM=4.21), chorion had an average viability of 78.18%±12.65% (n=4, SEM=6.32), amnion-chorion plate had an average viability of 69.05%±10.80% (n=4, SEM=5.40), and umbilical cord had an average viability of 63.30%±20.13% (n=4, SEM=10.06). Cells from perfusion, which did not undergo digestion, retained the highest average viability, 89.98±6.39% (n=5, SEM=2.86).

6.2.2.2 Cell Quantification

The populations of placental cells and umbilical cord cells were analyzed to determine the numbers of HLA ABC$^-$/CD45$^-$/CD34$^-$/CD133$^+$ cells. From the analysis of the BD FACSCalibur data, it was observed that the amnion, perfusate, and chorion contained the greatest total number of these cells, 30.72±21.80 cells (n=4, SEM=10.90), 26.92±22.56 cells (n=3, SEM=13.02), and 18.39±6.44 cells (n=2, SEM=4.55) respectively (data not shown). The amnion-chorion plate and umbilical cord contained the least total number of cells expressing the phenotype of interest, 4.72±4.16 cells (n=3, SEM=2.40) and 3.94±2.58 cells (n=3, SEM=1.49) respectively (data not shown).

Similarly, when the percent of total cells expressing the phenotype of interest was analyzed, it was observed that amnion and placental perfusate contained the highest percentages of cells expressing this phenotype (0.0319%±0.0202% (n=4, SEM=0.0101) and 0.0269%±0.0226% (n=3, SEM=0.0130) respectively (FIG. 2). Although umbilical cord contained a small number of cells expressing the phenotype of interest (FIG. 2), it contained the third highest percentage of cells expressing the phenotype of interest, 0.020±0.0226% (n=3, SEM=0.0131) (FIG. 2). The chorion and amnion-chorion plate contained the lowest percentages of cells expressing the phenotype of interest, 0.0184±0.0064% (n=2, SEM=0.0046) and 0.0177±0.0173% (n=3, SEM=0.010) respectively (FIG. 2).

Consistent with the results of the BD FACSCalibur analysis, the BD FACS Aria data also identified amnion, perfusate, and chorion as providing higher numbers of HLA ABC$^-$/CD45$^-$/CD34$^-$/CD133$^+$ cells than the remaining sources. The average total number of cells expressing the phenotype of interest among amnion, perfusate, and chorion was 126.47±55.61 cells (n=15, SEM=14.36), 81.65±34.64 cells (n=20, SEM=7.75), and 51.47±32.41 cells (n=15, SEM=8.37), respectively (data not shown). The amnion-chorion plate and umbilical cord contained the least total number of cells expressing the phenotype of interest, 44.89±37.43 cells (n=9, SEM=12.48) and 11.00±4.03 cells (n=9, SEM=1.34) respectively (data not shown).

BD FACS Aria data revealed that the perfusate and amnion produced the highest percentages of HLA ABC$^-$/CD45$^-$/CD34$^-$/CD133$^+$ cells, 0.1523±0.0227% (n=15, SEM=0.0059) and 0.0929±0.0419% (n=20, SEM=0.0094) respectively (FIG. 3). The amnion-chorion plate contained the third highest percentage of cells expressing the phenotype of interest, 0.0632±0.0333% (n=9, SEM=0.0111) (FIG. 3). The chorion and umbilical cord contained the lowest percentages of cells expressing the phenotype of interest, 0.0623±0.0249% (n=15, SEM=0.0064) and 0.0457±0.0055% (n=9, SEM=0.0018) respectively (FIG. 3).

After HLA ABC⁻/CD45⁻/CD34⁻/CD133⁺ cells were identified and quantified from each cell source, its cells were further analyzed and characterized for their expression of cell surface markers HLA-G, CD10, CD13, CD33, CD38, CD44, CD90, CD105, CD117, CD200, and CD105.

6.2.2.3 Placental Perfusate-Derived Cells

Perfusate-derived cells were consistently positive for HLA-G, CD33, CD117, CD10, CD44, CD200, CD90, CD38, CD105, and CD13 (FIG. 4). The average expression of each marker for perfusate-derived cells was the following: 37.15%±38.55% (n=4, SEM=19.28) of the cells expressed HLA-G; 36.37%±21.98% (n=7, SEM=8.31) of the cells expressed CD33; 39.39%±39.91% (n=4, SEM=19.96) of the cells expressed CD117; 54.97%±33.08% (n=4, SEM=16.54) of the cells expressed CD10; 36.79%±11.42% (n=4, SEM=5.71) of the cells expressed CD44; 41.83%±19.42% (n=3, SEM=11.21) of the cells expressed CD200; 74.25%±26.74% (n=3, SEM=15.44) of the cells expressed CD90; 35.10%±23.10% (n=3, SEM=13.34) of the cells expressed CD38; 22.87%±6.87% (n=3, SEM=3.97) of the cells expressed CD105; and 25.49%±9.84% (n=3, SEM=5.68) of the cells expressed CD13.

6.2.2.4 Amnion-Derived Cells

Amnion-derived cells were consistently positive for HLA-G, CD33, CD117, CD10, CD44, CD200, CD90, CD38, CD105, and CD13 (FIG. 5). The average expression of each marker for amnion-derived was the following: 57.27%±41.11% (n=3, SEM=23.73) of the cells expressed HLA-G; 16.23%±15.81% (n=6, SEM=6.46) of the cells expressed CD33; 62.32%±37.89% (n=3, SEM=21.87) of the cells expressed CD117; 9.71%±13.73% (n=3, SEM=7.92) of the cells expressed CD10; 27.03%±22.65% (n=3, SEM=13.08) of the cells expressed CD44; 6.42%±0.88% (n=2, SEM=0.62) of the cells expressed CD200; 57.61%±22.10% (n=2, SEM=15.63) of the cells expressed CD90; 63.76%±4.40% (n=2, SEM=3.11) of the cells expressed CD38; 20.27%±5.88% (n=2, SEM=4.16) of the cells expressed CD105; and 54.37%±13.29% (n=2, SEM=9.40) of the cells expressed CD13.

6.2.2.5 Chorion-Derived Cells

Chorion-derived cells were consistently positive for HLA-G, CD117, CD10, CD44, CD200, CD90, CD38, and CD13, while the expression of CD33, and CD105 varied (FIG. 6). The average expression of each marker for chorion cells was the following: 53.25%±32.87% (n=3, SEM=18.98) of the cells expressed HLA-G; 15.44%±11.17% (n=6, SEM=4.56) of the cells expressed CD33; 70.76%±11.87% (n=3, SEM=6.86) of the cells expressed CD117; 35.84%±25.96% (n=3, SEM=14.99) of the cells expressed CD10; 28.76%±6.09% (n=3, SEM=3.52) of the cells expressed CD44; 29.20%±9.47% (n=2, SEM=6.70) of the cells expressed CD200; 54.88%±0.17% (n=2, SEM=0.12) of the cells expressed CD90; 68.63%±44.37% (n=2, SEM=31.37) of the cells expressed CD38; 23.81%±33.67% (n=2, SEM=23.81) of the cells expressed CD105; and 53.16%±62.70% (n=2, SEM=44.34) of the cells expressed CD13.

6.2.2.6 Amnion-Chorion Plate-Derived Cells

Cells from amnion-chorion plate were consistently positive for HLA-G, CD33, CD117, CD10, CD44, CD200, CD90, CD38, CD105, and CD13 (FIG. 7). The average expression of each marker for amnion-chorion plate-derived cells was the following: 78.52%±13.13% (n=2, SEM=9.29) of the cells expressed HLA-G; 38.33%±15.74% (n=5, SEM=7.04) of the cells expressed CD33; 69.56%±26.41% (n=2, SEM=18.67) of the cells expressed CD117; 42.44%±53.12% (n=2, SEM=37.56) of the cells expressed CD10; 32.47%±31.78% (n=2, SEM=22.47) of the cells expressed CD44; 5.56% (n=1) of the cells expressed CD200; 83.33% (n=1) of the cells expressed CD90; 83.52% (n=1) of the cells expressed CD38; 7.25% (n=1) of the cells expressed CD105; and 81.16% (n=1) of the cells expressed CD13.

6.2.2.7 Umbilical Cord-Derived Cells

Umbilical cord-derived cells were consistently positive for HLA-G, CD33, CD90, CD38, CD105, and CD13, while the expression of CD117, CD10, CD44, and CD200 varied (FIG. 8). The average expression of each marker for umbilical cord-derived cells was the following: 62.50%±53.03% (n=2, SEM=37.50) of the cells expressed HLA-G; 25.67%±11.28% (n=5, SEM=5.04) of the cells expressed CD33; 44.45%±62.85% (n=2, SEM=44.45) of the cells expressed CD117; 8.33%±11.79% (n=2, SEM=8.33) of the cells expressed CD10; 21.43%±30.30% (n=2, SEM=21.43) of the cells expressed CD44; 0.0% (n=1) of the cells expressed CD200; 81.25% (n=1) of the cells expressed CD90; 64.29% (n=1) of the cells expressed CD38; 6.25% (n=1) of the cells expressed CD105; and 50.0% (n=1) of the cells expressed CD13.

A summary of all marker expression averages is shown in FIG. 9.

6.2.2.8 BD FACS Aria Sort Report

The three distinct populations of placental cells that expressed the greatest percentages of HLA ABC, CD45, CD34, and CD133 (cells derived from perfusate, amnion and chorion) were stained with 7AAD and the antibodies for these markers. The three populations were positively sorted for live cells expressing the phenotype of interest. The results of the BD FACS Aria sort are listed in table 2.

TABLE 2

BD FACS Aria Sort Report

| Cell Source | Events Processed | Events Sorted (Phenotype of Interest) | % Of Total |
|---|---|---|---|
| Perfusate | 135540110 | 51215 | 0.037786 |
| Amnion | 7385933 | 4019 | 0.054414 |
| Chorion | 108498122 | 4016 | 0.003701 |

The three distinct populations of positively sorted cells ("sorted") and their corresponding non-sorted cells were plated and the results of the culture were assessed on day 12 (Table 3). Sorted perfusate-derived cells, plated at a cell density of 40,600/cm², resulted in small, round, non-adherent cells. Two out of the three sets of non-sorted perfusate-derived cells, each plated at a cell density of 40,600/cm², resulted in mostly small, round, non-adherent cells with several adherent cells located around the periphery of well. Non-sorted perfusate-derived cells, plated at a cell density of 93,800/cm², resulted in mostly small, round, non-adherent cells with several adherent cells located around the well peripheries.

Sorted amnion-derived cells, plated at a cell density of 6,300/cm², resulted in small, round, non-adherent cells. Non-sorted amnion-derived cells, plated at a cell density of 6,300/cm², resulted in small, round, non-adherent cells. Non-sorted amnion-derived cells plated at a cell density of 62,500/cm² resulted in small, round, non-adherent cells.

Sorted chorion-derived cells, plated at a cell density of 6,300/cm², resulted in small, round, non-adherent cells. Non-sorted chorion-derived cells, plated at a cell density of 6,300/cm², resulted in small, round, non-adherent cells. Non-sorted chorion-derived cells plated at a cell density of 62,500/cm², resulted in small, round, non-adherent cells.

Subsequent to the performance of the experiments related above, and further culture of the placental stem cells, it was determined that the labeling of the antibodies for CD117 and CD133, in which a streptavidin-conjugated antibody was labeled with biotin-conjugated phycoerythrin (PE), produced background significant enough to resemble a positive reading. This background had initially resulted in the placental stem cells being deemed to be positive for both markers. When a different label, APC or PerCP was used, the background was reduced, and the placental stem cells were correctly determined to be negative for both CD117 and CD133.

6.3 Example 3

Characterization of Placental Stem Cells and Umbilical Cord Stem Cells

This Example demonstrates an exemplary cell surface marker profile of placental stem cells.

Placental stem cells or umbilical cord stem cells, obtained by enzymatic digestion, in culture medium were washed once by adding 2 mL 2% FBS-PBS and centrifuging at 400 g for 5 minutes. The supernatant was decanted, and the pellet was resuspended in 100-200 μL 2% FBS-PBS. 4 tubes were prepared with BD™ CompBeads (Cat #552843) by adding 100 μl of 2% FBS-PBS to each tube, adding 1 full drop (approximately 60 μl) of the BD™ CompBeads Negative Control and 1 drop of the BD™ CompBeads Anti-Mouse beads to each tube, and vortexing. To the 4 tubes of BD™ CompBeads, the following antibodies were added:

| Tube# | Antibody | Cat# | Clone | Volume μL |
|---|---|---|---|---|
| 1 | CD105 FITC | FAB10971F | 166707 | 10 |
| 2 | CD200 PE | 552475 | MRC-OX-104 | 20 |
| 3 | CD10 PE-Cy7 | 341102 | HI10a | 5 |
| 4 | CD34 APC | 340667 | 8G12 | 5 |

Control tubes were prepared as follows:

| Tube# | Antibody | Cat# | Clone | Volume μL |
|---|---|---|---|---|
| 1 | Unstained | — | — | — |
| 2 | IgG FITC/IgG PE//IgG APC | 555787, 555786, 550931 | G18-145 | 10 ea |

The following antibodies were added to the sample tubes:

| Antibody | Cat# | Clone | Volume μL |
|---|---|---|---|
| CD105 FITC | FAB10971F | 166707 | 10 |
| CD200 PE | 552475 | MRC-OX-104 | 20 |
| CD10 PE-Cy7 | 341102 | HI10a | 5 |
| CD34 APC | 340667 | 8G12 | 5 |

The control and sample tubes were incubated in the dark at room temperature for 30 minutes. After incubation, the tubes were washed by adding 2 mL 2% FBS-PBS and centrifuging at 400 g for 5 minutes. The supernatant was decanted, and the pellet was resuspended in 100-200 μL 2% FBS-PBS and acquire on flow cytometer. All other antibodies were used following this procedure.

Matched placental stem cells from amniotic membrane and umbilical cord stem cells were analyzed using fluorescently-labeled antibodies and flow cytometry to identify cell surface markers that were present or absent. Markers analyzed included CD105 (proliferation related endothelial specific marker); CD200 (marker associated with regulatory function); CD34 (expressed on endothelial cells and on hematopoietic stem cells); CD10 (stem cell/precursor cell marker); cytokeratin K (epithelial marker); CD44 (cell migration, lymphocyte homing, hematopoiesis); CD45 (lineage marker); CD133 (marker for hematopoietic progenitor cells); CD117 (stem cell factor (c-Kit)); CD90 (expressed on primitive hematopoietic stem cells in normal bone marrow, cord blood and fetal liver cells); HLA ABC (pan MHC I, antigen presentation, immunogenicity); β-2-microglobulin (associates with MHC I, antigen presentation, immunogenicity); HLA DR, DQ, DP (pan MHC II, antigen presentation, immunogenicity); and CD80/86 (co-stimulatory molecules for antigen presentation).

Flow cytometry results showed that for the placental stem cells that were tested, 93.83% of cells were CD105$^+$, 90.76% of cells were CD200$^+$, and 86.93% of cells were both CD105$^+$ and CD200$^+$. 99.97% of cells were CD10$^+$, 99.15% of cells were CD34$^-$, and 99.13% of cells were both CD10$^+$ and CD34$^-$. 98.71% of cells were cytokeratin positive, 99.95% of cells were CD44$^+$, and 98.71% of cells were positive for both cytokeratin and CD44. 99.51% of cells were CD45$^-$, 99.78% of cells were negative for CD133, and 99.39% of cells were negative for both CD45 and CD133. 99.31% of cells were positive for CD90, 99.7% were negative for CD117, and 99.01% were positive for CD90 and negative for CD117. 95.7% of cells were negative for both CD80 and CD86.

Flow cytometry results for umbilical cord stem cells showed that 95.95% of cells were CD200$^+$, 94.71% were CD105$^+$, and 92.69% were CD105$^+$ and CD200$^+$. 99.93% of the cells were CD10$^+$, 99.99% of the cells were CD34$^-$, and 99.6% of the cells were both CD10$^+$ and CD34$^-$. 99.45% of the cells were cytokeratin positive, 99.78% of the cells were CD44$^+$, and 99.3% of the cells were positive for both cytokeratin and CD44. 99.33% of the cells were CD45$^-$, 99.74% were CD133$^-$, and 99.15% of the cells were both CD45$^-$ and CD133$^-$. 99.84% of the cells were CD117$^-$, 98.78% of the cells were CD90$^+$, and 98.64% of the cells were both CD90$^+$ and CD117$^-$.

One phenotype (CD200$^+$, CD105$^+$, CD10$^+$, CD34$^-$ appears to be consistent over numerous such analyses. This phenotype is additionally positive for CD90, CD44, HLA ABC (weak), β-2-microglobulin (weak), and cytokeratin K, and negative for HLA DR, DQ, DP, CD117, CD133, and CD45.

6.4 Example 4

Determination of Aldehyde Dehydrogenase Activity in Placental Stem Cells

The level of aldehyde dehydrogenase (ALDH) activity, a potential marker of stem cell engraftment capability, was determined using and ALDEFLUOR® Assay Kit from Stem Cell Technologies, Inc. Typically, more primitive, undifferentiated stem cells demonstrate less ALDH activity than more differentiated stem cells.

The assay uses ALDEFLUOR®, a fluorescent ALDH substrate (Aldagen, Inc., Durham, N.C.). The manufacturer's protocol was followed. The dry ALDEFLUOR® reagent is provided in a stable, inactive form. The ALDEFLUOR® was activated by dissolving the dry compound in dimethylsulfoxide (DMSO) and adding 2N HCl, and was added immediately to the cells. A control tube was also established by combing the cells with ALDEFLUOR® plus DEAB, a specific inhibitor of ALDH.

Cells analyzed included four umbilical cord stem cell lines and three placental stem cell lines from amnion-chorion plate, a bone marrow-derived mesenchymal stem cell line (BM-MSC), an adipose-derived stem cell line (ADSC), a human villous trophoblast cell line (HVT), and $CD34^+$ stem cells purified from cord blood.

The assay proceeded as follows. Sample concentration was adjusted to $1 \times 10^6$ cells/ml with Assay buffer provided with the ALDEFLUOR® Assay Kit. 1 mL of adjusted cell suspension into experimental and control tube for each of the cell lines tested, and 5 µl of DEAB was additionally added to the control tube labeled as control.

ALDEFLUOR® substrate was activated by adding 25 µl of DMSO to the dry ALDEFLUOR® Reagent, and let stand for 1 minute at RT. 25 µl of 2N HCL was added and mixed well. This mixture was incubated for 15 min at RT. 360 µl of ALDEFLUOR® Assay Buffer was added to the vial and mixed. The resulting mixture was stored at 2-8° C. during use.

5 µl of the activated ALDEFLUOR® reagent was added per 1 milliliter of sample to the experimental tubes, and 0.5 ml of this mixture was immediately transferred into the control tubes. The experimental and control tubes for each cell line were incubated for 30 minutes at 37° C. After incubation, the tubes were centrifuged at 400×g, and the supernatant was discarded. The cells in the resulting pellet were resuspended in 0.5 ml Assay Buffer and analyze by flow cytometry. Data was analyzed using FLOWJO™ software (Tree Star, Ashland, Oreg.). SSC vs FSC and SSC vs FL1 plots were created in the FLOWJO™ workspace. Control and experimental data files were opened for each sample, and the appropriate gates were determined based on control samples. Positive cells were calculated as a percent ALDEFLUOR® positive out of the total number of events counted.

Placental stem cell lines demonstrated ALDH activity of from about 3% to about 25% (3.53%, 8.76% and 25.26%). Umbilical cord stem cell lines demonstrated ALDH activity of from about 16% to about 20% (16.59%, 17.01%, 18.44% and 19.83%). In contrast, BM-MSC and HVT were negative and 1.5% respectively for ALDH, but the adipose derived MSC is close to 30% $ALDH^+$. The positive control $CD34^+$ cells purified from umbilical cord blood were, as expected, highly positive (75%) for ALDH.

6.5 Example 5

Collection of Placental Stem Cells by Closed-Circuit Perfusion

This Example demonstrates one method of collecting placental stem cells by perfusion.

A post-partum placenta is obtained within 24 hours after birth. The umbilical cord is clamped with an umbilical cord clamp approximately 3 to 4 inches about the placental disk, and the cord is cut above the clamp. The umbilical cord is either discarded, or processed to recover, e.g., umbilical cord stem cells, and/or to process the umbilical cord membrane for the production of a biomaterial. Excess amniotic membrane and chorion is cut from the placenta, leaving approximately ¼ inch around the edge of the placenta. The trimmed material is discarded.

Starting from the edge of the placental membrane, the amniotic membrane is separated from the chorion using blunt dissection with the fingers. When the amniotic membrane is entirely separated from the chorion, the amniotic membrane is cut around the base of the umbilical cord with scissors, and detached from the placental disk. The amniotic membrane can be discarded, or processed, e.g., to obtain stem cells by enzymatic digestion, or to produce, e.g., an amniotic membrane biomaterial.

The fetal side of the remaining placental material is cleaned of all visible blood clots and residual blood using sterile gauze, and is then sterilized by wiping with an iodine swab than with an alcohol swab. The umbilical cord is then clamped crosswise with a sterile hemostat beneath the umbilical cord clamp, and the hemostat is rotated away, pulling the cord over the clamp to create a fold. The cord is then partially cut below the hemostat to expose a cross-section of the cord supported by the clamp. Alternatively, the cord is clamped with a sterile hemostat. The cord is then placed on sterile gauze and held with the hemostat to provide tension. The cord is then cut straight across directly below the hemostat, and the edge of the cord near the vessel is re-clamped.

The vessels exposed as described above, usually a vein and two arteries, are identified, and opened as follows. A closed alligator clamp is advanced through the cut end of each vessel, taking care not to puncture the clamp through the vessel wall. Insertion is halted when the tip of the clamp is slightly above the base of the umbilical cord. The clamp is then slightly opened, and slowly withdrawn from the vessel to dilate the vessel.

Plastic tubing, connected to a perfusion device or peristaltic pump, is inserted into each of the placental arteries. Plastic tubing, connected to a 250 mL collection bag, is inserted into the placental vein. The tubing is taped into place.

A small volume of sterile injection grade 0.9% NaCl solution to check for leaks. If no leaks are present, the pump speed is increased, and about 750 mL of the injection grade 0.9% NaCl solution is pumped through the placental vasculature. Perfusion can be aided by gently massaging the placental disk from the outer edges to the cord. When a collection bag is full, the bag is removed from the coupler connecting the tubing to the bag, and a new bag is connected to the tube.

When collection is finished, the collection bags are weighed and balanced for centrifugation. After centrifugation, each bag is placed inside a plasma extractor without disturbing the pellet of cells. The supernatant within the bags is then removed and discarded. The bag is then gently massaged to resuspend the cells in the remaining supernatant. Using a sterile 1 mL syringe, about 300-500 µL of cells is withdrawn from the collection bag, via a sampling site coupler, and transferred to a 1.5 mL centrifuge tube. The weight and volume of the remaining perfusate are determined, and ⅓ volume of hetastarch is added to the perfusate and mixed thoroughly. The number of cells per mL is determined. Red blood cells are removed from the perfusate using a plasma extractor.

Placental cells are then immediately cultured to isolate placental stem cells, or are cryopreserved for later use.

6.6 Example 6

Differentiation of Placental Stem Cells

6.6.1 Induction of Differentiation into Neurons

Neuronal differentiation of placental stem cells can also be accomplished as follows:

1. Placental stem cells are grown for 24 hr in preinduction medium consisting of DMEM/20% FBS and 1 mM beta-mercaptoethanol.
2. The preinduction medium is removed and cells are washed with PBS.
3. Neuronal induction medium consisting of DMEM and 1-10 mM betamercaptoethanol is added to the cells. Alternatively, induction media consisting of DMEM/2% DMSO/200 µM butylated hydroxyanisole may be used.
4. In certain embodiments, morphologic and molecular changes may occur as early as 60 minutes after exposure to serum-free media and betamercaptoethanol. RT/PCR may be used to assess the expression of e.g., nerve growth factor receptor and neurofilament heavy chain genes.

6.6.2 Induction of Differentiation into Adipocytes

Several cultures of placental stem cells derived from enzymatic digestion of amnion, at 50-70% confluency, were induced in medium comprising (1) DMEM/MCDB-201 with 2% FCS, 0.5% hydrocortisone, 0.5 mM isobutylmethylxanthine (IBMX), 60 µM indomethacin; or (2) DMEM/MCDB-201 with 2% FCS and 0.5% linoleic acid. Cells were examined for morphological changes; after 3-7 days, oil droplets appeared. Differentiation was also assessed by quantitative real-time PCR to examine the expression of specific genes associated with adipogenesis, i.e., PPAR-γ2, aP-2, lipoprotein lipase, and osteopontin. Two cultures of placental stem cells showed an increase of 6.5-fold and 24.3-fold in the expression of adipocyte-specific genes, respectively. Four other cultures showed a moderate increase (1.5-2.0-fold) in the expression of PPAR-γ2 after induction of adipogenesis.

In another experiment, placental stem cells obtained from perfusate were cultured in DMEM/MCDB-201 (Chick fibroblast basal medium) with 2% FCS. The cells were trypsinized and centrifuged. The cells were resuspended in adipo-induction medium (AIM) 1 or 2. AIM1 comprised MesenCult Basal Medium for human Mesenchymal Stem Cells (StemCell Technologies) supplemented with Mesenchymal Stem Cell Adipogenic Supplements (StemCell Technologies). AIM2 comprised DMEM/MCDB-201 with 2% FCS and LA-BSA (1%). About $1.25 \times 10^5$ placental stem cells were grown in 5 mL AIM1 or AIM2 in T-25 flasks. The cells were cultured in incubators for 7-21 days. The cells developed oil droplet vacuoles in the cytoplasm, as confirmed by oil-red staining, suggesting the differentiation of the stem cells into adipocytes.

Adipogenic differentiation of placental stem cells can also be accomplished as follows:

1. Placental stem cells are grown in MSCGM (Cambrex) or DMEM supplemented with 15% cord blood serum.
2. Three cycles of induction/maintenance are used. Each cycle consists of feeding the placental stem cells with Adipogenesis Induction Medium (Cambrex) and culturing the cells for 3 days (at 37° C., 5% $CO_2$), followed by 1-3 days of culture in Adipogenesis Maintenance Medium (Cambrex). An alternate induction medium that can be used contains 1 µM dexamethasone, 0.2 mM indomethacin, 0.01 mg/ml insulin, 0.5 mM IBMX, DMEM-high glucose, FBS, and antibiotics.
3. After 3 complete cycles of induction/maintenance, the cells are cultured for an additional 7 days in adipogenesis maintenance medium, replacing the medium every 2-3 days.
4. A hallmark of adipogenesis is the development of multiple intracytoplasmic lipid vesicles that can be easily observed using the lipophilic stain oil red O. Expression of lipase and/or fatty acid binding protein genes is confirmed by RT/PCR in placental stem cells that have begun to differentiate into adipocytes.

6.6.3 Induction of Differentiation into Osteocytes

Osteogenic medium was prepared from 185 mL Cambrex Differentiation Basal Medium—Osteogenic and SingleQuots (one each of dexamethasone, 1-glutamine, ascorbate, pen/strep, MCGS, and β-glycerophosphate). Placental stem cells from perfusate were plated, at about $3 \times 10^3$ cells per $cm^2$ of tissue culture surface area in 0.2-0.3 mL MSCGM per $cm^2$ tissue culture area. Typically, all cells adhered to the culture surface for 4-24 hours in MSCGM at 37° C. in 5% $CO_2$. Osteogenic differentiation was induced by replacing the medium with Osteogenic Differentiation medium. Cell morphology began to change from the typical spindle-shaped appearance of the adherent placental stem cells, to a cuboidal appearance, accompanied by mineralization. Some cells delaminated from the tissue culture surface during differentiation.

Osteogenic differentiation can also be accomplished as follows:

1. Adherent cultures of placental stem cells are cultured in MSCGM (Cambrex) or DMEM supplemented with 15% cord blood serum.
2. Cultures are cultured for 24 hours in tissue culture flasks.
3. Osteogenic differentiation is induced by replacing MSCGM with Osteogenic Induction Medium (Cambrex) containing 0.1 µM dexamethasone, 0.05 mM ascorbic acid-2-phosphate, 10 mM beta glycerophosphate.
4. Cells are fed every 3-4 days for 2-3 weeks with Osteogenic Induction Medium.
5. Differentiation is assayed using a calcium-specific stain and RT/PCR for alkaline phosphatase and osteopontin gene expression.

6.6.4 Induction of Differentiation into Pancreatic Cells

Pancreatic differentiation is accomplished as follows:

1. Placental stem cells are cultured in DMEM/20% CBS, supplemented with basic fibroblast growth factor, 10 ng/ml; and transforming growth factor beta-1,2 ng/ml. KnockOut Serum Replacement may be used in lieu of CBS.
2. Conditioned media from nestin-positive neuronal cell cultures is added to media at a 50/50 concentration.
3. Cells are cultured for 14-28 days, refeeding every 3-4 days.
4. Differentiation is characterized by assaying for insulin protein or insulin gene expression by RT/PCR.

6.6.5 Induction of Differentiation into Cardiac Cells

Myogenic (cardiogenic) differentiation is accomplished as follows:

1. Placental stem cells are cultured in DMEM/20% CBS, supplemented with retinoic acid, 1 µM; basic fibroblast growth factor, 10 ng/ml; and transforming growth factor beta-1, 2 ng/ml; and epidermal growth factor, 100 ng/ml. KnockOut Serum Replacement (Invitrogen, Carlsbad, Calif.) may be used in lieu of CBS.
2. Alternatively, placental stem cells are cultured in DMEM/20% CBS supplemented with 50 ng/ml Cardiotropin-1 for 24 hours.

3. Alternatively, placental stem cells are maintained in protein-free media for 5-7 days, then stimulated with human myocardium extract (escalating dose analysis). Myocardium extract is produced by homogenizing 1 gm human myocardium in 1% HEPES buffer supplemented with 1% cord blood serum. The suspension is incubated for 60 minutes, then centrifuged and the supernatant collected.
4. Cells are cultured for 10-14 days, refeeding every 3-4 days.
5. Differentiation is confirmed by demonstration of cardiac actin gene expression by RT/PCR.

6.6.6 Induction of Differentiation into Chondrocytes
6.6.6.1 General Method

Chondrogenic differentiation of placental stem cells is generally accomplished as follows:
1. Placental stem cells are maintained in MSCGM (Cambrex) or DMEM supplemented with 15% cord blood serum.
2. Placental stem cells are aliquoted into a sterile polypropylene tube. The cells are centrifuged (150×g for 5 minutes), and washed twice in Incomplete Chondrogenesis Medium (Cambrex).
3. After the last wash, the cells are resuspended in Complete Chondrogenesis Medium (Cambrex) containing 0.01 µg/ml TGF-beta-3 at a concentration of 5×10(5) cells/ml.
4. 0.5 ml of cells is aliquoted into a 15 ml polypropylene culture tube. The cells are pelleted at 150×g for 5 minutes. The pellet is left intact in the medium.
5. Loosely capped tubes are incubated at 37° C., 5% $CO^2$ for 24 hours.
6. The cell pellets are fed every 2-3 days with freshly prepared complete chondrogenesis medium.
7. Pellets are maintained suspended in medium by daily agitation using a low speed vortex.
8. Chondrogenic cell pellets are harvested after 14-28 days in culture.
9. Chondrogenesis is characterized by e.g., observation of production of esoinophilic ground substance, assessing cell morphology, an/or RT/PCR confirmation of collagen 2 and/or collagen 9 gene expression and/or the production of cartilage matrix acid mucopolysaccharides, as confirmed by Alcian blue cytochemical staining.

6.6.6.2 Differentiation of Placental and Umbilical Cord Stem Cells into Chondrogenic Cells The Example demonstrates the differentiation of placental stem cells into chondrogenic cells and the development of cartilage-like tissue from such cells.

Cartilage is an avascular, alymphatic tissue that lacks a nerve supply. Cartilage has a low chondrocyte density (<5%), however these cells are surprisingly efficient at maintaining the extracellular matrix around them. Three main types of cartilage exist in the body: (1) articular cartilage, which facilitates joint lubrication in joints; (2) fibrocartilage, which provides shock absorption in, e.g., meniscus and intervertebral disc; and (3) elastic cartilage, which provides anatomical structure in, e.g., nose and ears. All three types of cartilage are similar in biochemical structure.

Joint pain is a major cause of disability and provides an unmet need of relief in the area of orthopedics. Primary osteoarthritis (which can cause joint degeneration), and trauma are two common causes of pain. Approximately 9% of the U.S. population has osteoarthritis of hip or knee, and more than 2 million knee surgeries are performed yearly. Unfortunately, current treatments are more geared towards treatment of symptoms rather than repairing the cartilage. Natural repair occurs when fibroblast-like cells invade the area and fill it with fibrous tissue which is neither as resilient or elastic as the normal tissue, hence causing more damage. Treatment options historically included tissue grafts, subchondral drilling, or total joint replacement. More recent treatments however include CARTICEL®, an autologous chondrocyte injection; SYNVISC® and ORTHOVISC®, which are hyaluronic acid injections for temporary pain relief; and CHONDROGEN™, an injection of adult mesenchymal stem cells for meniscus repair. In general, the trend seems to be lying more towards cellular therapies and/or tissue engineered products involving chondrocytes or stem cells.

Materials and Methods.

Two placental stem cell lines, designated AC61665, P3 (passage 3) and AC63919, P5, and two umbilical cord stem cell lines, designated UC67249, P2 and UC67477, P3 were used in the studies outlined below. Human mesenchymal stem cells (MSC) were used as positive controls, and an osteosarcoma cell line, MC3T3, and human dermal fibroblasts (HDF) were used as negative controls.

Placental and umbilical cord stem cells were isolated and purified from full term human placenta by enzymatic digestion. Human MSC cells and HDF cells were purchased from Cambrex, and MC3T3 cells were purchased from American Type Culture Collection. All cell lines used were centrifuged into pellets in polypropylene centrifuge tubes at 800 RPM for 5 minutes and grown in both chondrogenic induction media (Cambrex) and non-inducing basal MSC media (Cambrex). Pellets were harvested and histologically analyzed at 7, 14, 21 and 28 days by staining for glycosaminoglycans (GAGs) with Alcian Blue, and/or for collagens with Sirius Red. Collagen type was further assessed with immunostaining. RNA analysis for cartilage-specific genes was performed at 7 and 14 days.

Results

Experiment 1: Chondrogenesis studies were designed to achieve three main objectives: (1) to demonstrate that placental and umbilical cord stem cells can differentiate and form cartilage tissue; (2) to demonstrate that placental and umbilical cord stem cells can differentiate functionally into chondrocytes; and (3) to validate results obtained with the stem cells by evaluating control cell lines.

For objective 1, in a preliminary study, one placental stem cell line was cultured in chondrogenic induction medium in the form of cell pellets, either with or without bone morphogenic protein (BMP) at a final concentration of 500 ng/mL. Pellets were assessed for evidence of chondrogenic induction every week for 4 weeks. Results indicated that the pellets do increase in size over time. However, no visual differences were noted between the $BMP^+$ and $BMP^-$ samples. Pellets were also histologically analyzed for GAG's, an indicator of cartilage tissue, by staining with Alcian Blue. $BMP^+$ cells generally appeared more metabolically active with pale vacuoles whereas $BMP^-$ cells were smaller with dense-stained nuclei and less cytoplasm (reflects low metabolic activity). At 7 days, $BMP^+$ cells had stained heavily blue, while $BMP^-$ had stained only faintly. By 28 days of induction, both $BMP^+$ and $BMP^-$ cells were roughly equivalently stained with Alcian Blue. Overall, cell density decreased over time, and matrix overtook the pellet. In contrast, the MC3T3 negative cell line did not demonstrate any presence of GAG when stained with Alcian Blue.

Experiment 2: Based on the results of Experiment 1, a more detailed study was designed to assess the chondrogenic differentiation potential of two placental stem cell and two umbilical cord stem cell lines. In addition to the Alcian Blue histology, cells were also stained with Sirius Red, which is specific for type II collagen. Multiple pellets were made for each cell line, with and without induction media.

The pelleted, cultured cell lines were first assessed by gross observation for macroscopic generation of cartilage. Overall, the stem cell lines were observed to make pellets as early as day 1. These pellets grew over time and formed a tough matrix, appearing white, shining and cartilage-like, and became mechanically tough. By visual inspection, pellets from placental stem cells or umbilical cord stem cells were much larger than the MSC controls. Control pellets in non-induction media started to fall apart by Day 11, and were much smaller at 28 days than pellets developed by cells cultured in chondrogenic induction medium. Visually, there were no differences between pellets formed by placental stem cells or umbilical cord. However, the UC67249 stem cell line, which was initiated in dexamethasone-free media, formed larger pellets. Negative control MC3T3 cells did not form pellets; however, HDFs did form pellets.

Representative pellets from all test groups were then subjected to histological analysis for GAG's and collagen. Generally, pellets formed by the stem cells under inducing conditions were much larger and stayed intact better than pellets formed under non-inducing conditions. Pellets formed under inducing conditions showed production of GAGs and increasing collagen content over time, and as early as seven days, while pellets formed under non-inducing conditions showed little to no collagen production, as evidenced by weak Alcian Blue staining. In general, the placental stem cells and umbilical cord stem cells appeared, by visual inspection, to produce tougher, larger pellets, and appeared to be producing more collagen over time, than the hMSCs. Moreover, over the course of the study, the collagen appeared to thicken, and the collagen type appeared to change, as evidenced by changes in the fiber colors under polarized light (colors correlate to fiber thickness which may be indicative of collagen type). Non-induced placental stem cells produced much less type II collagen, if any, compared to the induced stem cells. Over the 28-day period, cell density decreased as matrix production increased, a characteristic of cartilage tissue.

These studies confirm that placental and umbilical cord stem cells can be differentiated along a chondrogenic pathway, and can easily be induced to form cartilage tissue. Initial observations indicate that such stem cells are preferable to MSCs for the formation of cartilage tissue.

6.7 Example 7

Hanging Drop Culture of Placental Stem Cells

Placental adherent stem cells in culture are trypsinized at 37° C. for about 5 minutes, and loosened from the culture dish by tapping. 10% FBS is added to the culture to stop trypsinization. The cells are diluted to about $1 \times 10^4$ cells per mL in about 5 mL of medium. Drops (either a single drop or drops from a multi-channel micropipette are placed on the inside of the lid of a 100 mL Petri dish. The lid is carefully inverted and placed on top of the bottom of the dish, which contains about 25 ml of sterile PBS to maintain the moisture content in the dish atmosphere. Cells are grown for 6-7 days.

6.8 Example 8

Placental Tissue Digestion to Obtain Placental Stem Cells

This Example demonstrates a scaled up isolation of placental stem cells by enzymatic digestion.

Approximately 10 grams of placental tissue (amnion and chorion) is obtained, macerated, and digested using equal volumes of collagenase A (1 mg/ml) (Sigma) and Trypsin-EDTA (0.25%) (Gibco-BRL) in a total volume of about 30 ml for about 30 minutes at 37° C. Cells liberated by the digestion are washed 3× with culture medium, distributed into four T-225 flasks and cultured as described in Example 1. Placental stem cell yield is between about $4 \times 10^8$ and $5 \times 10^8$ cells per 10 g starting material. Cells, characterized at passage 3, are predominantly $CD10^+$, $CD90^+$, $CD105^+$, $CD200^+$, $CD34^-$ and $CD45^-$.

6.9 Example 9

Production of Cryopreserved Stem Cell Product and Stem Cell Bank

This Example demonstrates the isolation of placental stem cell and the production of a frozen stem cell-based product.

Summary: Placental tissue is dissected and digested, followed by primary and expansion cultures to achieve an expanded cell product that produces many cell doses. Cells are stored in a two-tiered cell bank and are distributed as a frozen cell product. All cell doses derived from a single donor placenta are defined as a lot, and one placenta lot is processed at a time using sterile technique in a dedicated room and Class 100 laminar flow hood. The cell product is defined as being $CD105^+$, $CD200^+$, $CD10^+$, and $CD34^-$, having a normal karyotype and no or substantially no maternal cell content.

6.9.1 Obtaining Stem Cells

Tissue Dissection and Digestion: A placenta is obtained less than 24 hours after expulsion. Placental tissue is obtained from amnion, a combination of amnion and chorion, or chorion. The tissue is minced into small pieces, about 1 mm in size. Minced tissue is digested in 1 mg/ml Collagenase 1A for 1 hour at 37° C. followed by Trypsin-EDTA for 30 minutes at 37° C. After three washes in 5% FBS in PBS, the tissue is resuspended in culture medium.

Primary Culture: The purpose of primary culture is to establish cells from digested placental tissue. The digested tissue is suspended in culture medium and placed into Corning T-flasks, which are incubated in a humidified chamber maintained at 37° C. with 5% $CO_2$. Half of the medium is replenished after 5 days of culture. High-density colonies of cells form by 2 weeks of culture. Colonies are harvested with Trypsin-EDTA, which is then quenched with 2% FBS in PBS. Cells are centrifuged and resuspended in culture medium for seeding expansion cultures. These cells are defined as Passage 0 cells having doubled 0 times.

Expansion Culture: Cells harvested from primary culture, harvested from expansion culture, or thawed from the cell bank are used to seed expansion cultures. Cell Factories (NUNC™) are treated with 5% $CO_2$ in air at 50 ml/min/tray for 10 min through a sterile filter and warmed in a humidified incubator maintained at 37° C. with 5% $CO_2$. Cell seeds are counted on a hemacytometer with trypan blue, and cell number, viability, passage number, and the cumulative number of doublings are recorded. Cells are suspended in culture medium to about $2.3 \times 10^4$ cells/ml and 110 ml/tray are seeded in the Cell Factories. After 3-4 days and again at 5-6 days of culture, culture medium is removed and replaced with fresh medium, followed by another treatment with 5% $CO_2$ in air. When cells reach approximately $10^5$ cells/cm$^2$, cells are harvested with Trypsin-EDTA, followed by quenching with 2% FBS in PBS. Cell are then centrifuged and resuspended in culture medium.

Cryopreservation: Cells to be frozen down are harvested from culture with Trypsin-EDTA, quenched with 2% FBS in PBS, and counted on a hemacytometer. After centrifugation, cells are resuspended with 10% DMSO in FBS to a concentration of about 1 million cells/ml for cells to be used for assembly of a cell bank, and 10 million cells/ml for individual frozen cell doses. The cell solution is transferred to a freezing container, which is placed in an isopropyl alcohol bath in a −80° C. freezer. The following day, cells are transferred to liquid nitrogen.

6.9.2 Design of a Stem Cell Bank

A "lot" is defined as all cell doses derived from a single donor placenta. Cells maintained normal growth, karyotype, and cell surface maker phenotype for over 8 passages and 30 doublings during expansion culture. Given this limitation, doses comprise cells from 5 passages and about 20 doublings. To generate a supply of equivalent cells, a single lot is expanded in culture and is stored in a two-tiered cell bank and frozen doses. In particular, cells harvested from the primary culture, which are defined as Passage 0 cells having undergone 0 doublings, are used to initiate an expansion culture. After the first passage, approximately 4 doublings occur, and cells are frozen in a Master Cell Bank (MCB). Vials from the MCB are used to seed additional expansion cultures. After two additional passages of cells thawed from the MCB, cells are frozen down in a Working Cell Bank (WCB), approximately 12 cumulative doublings. Vials from the WCB are used to seed an expansion culture for another 2 passages, resulting in Passage 5 cells at approximately 20 doublings that are frozen down into individual doses.

6.9.3 Thawing Cells for Culture

Frozen containers of cells are placed into a sealed plastic bag and immersed in a 37° C. water bath. Containers are gently swirled until all of the contents are melted except for a small piece of ice. Containers are removed from the sealed plastic bag and a 10× volume of culture medium is slowly added to the cells with gentle mixing. A sample is counted on the hemacytometer and seeded into expansion cultures.

6.9.4 Thawing Cells for Injection

Frozen containers of cells are transferred to the administration site in a dry nitrogen shipper. Prior to administration, containers are placed into a sealed plastic bag and immersed in a 37° C. water bath. Containers are gently swirled until all of the contents are melted except for a small piece of ice. Containers are removed from the sealed plastic bag and an equal volume of 2.5% HSA/5% Dextran is added. Cells are injected with no further washing.

6.9.5 Testing and Specifications

A maternal blood sample accompanies all donor placentas. The sample is screened for Hepatitis B core antibody and surface antigen, Hepatitis C Virus antibody and nucleic acid, and HIV I and II antibody and nucleic acid. Placental processing and primary culture begins prior to the receipt of test results, but continues only for placentas associated with maternal blood samples testing negative for all viruses. A lot is rejected if the donor tests positive for any pathogen. In addition, the tests described in Table 3 are performed on the MCB, the WCB, and a sample of the cell dose material derived from a vial of the WCB. A lot is released only when all specifications are met.

TABLE 3

Cell testing and specifications

| Test | Methods | Required Result |
|---|---|---|
| Sterility | BD BACTEC PEDS PLUS/F and BACTEC Myco/F Lytic | Negative |
| Endotoxin | LAL gel clot | ≦5 EU/ml* |
| Viability | Trypan Blue | >70% viable |
| Mycoplasma | Direct culture, DNA-fluorochrome (FDA PTC 1993) | Negative |
| Identity | Flow cytometry (see below) | $CD105^+$, $CD200^{+,}$ $CD10^+$, $CD34^-$ |
| Cell Purity | Microsatellite | No contaminating cell detected |
| Karyotype | G-banding and chromosome count on metaphase cells | Normal |

*For the product designed to be 40 ml of frozen cells/dose and a maximum of 5 EU/ml, the cell product is below the upper limit of 5 EU/kg/dose for recipients over 40 kg in body weight.

6.9.6 Surface Marker Phenotype Analysis

Cells are placed in 1% paraformaldehyde (PFA) in PBS for 20 minutes and stored in a refrigerator until stained (up to a week). Cells are washed with 2% FBS, 0.05% sodium azide in PBS (Staining Buffer) and then resuspended in staining buffer. Cells are stained with the following antibody conjugates: CD105-FITC, CD200-PE, CD34-PECy7, CD10-APC. Cells are also stained with isotype controls. After 30 minute incubation, the cells are washed and resuspended with Staining Buffer, followed by analysis on a flow cytometer. Cells having an increased fluorescence compared to isotype controls are counted as positive for a marker.

6.10 Example 10

Identification of Placental Stem Cell-Specific Genes

Gene expression patterns from placental stem cells from amnion-chorion (AC) and umbilical cord (UC) were compared to gene expression patterns of multipotent bone marrow-derived mesenchymal stem cells (BM) and dermal fibroblasts (DF), the latter of which is considered to be terminally differentiated. Cells were grown for a single passage, an intermediate number of passages, and large number of passages (including until senescence). Results indicate that the number of population doublings has a major impact on gene expression. A set of genes was identified that are up-regulated in AC and UC, and either down-regulated or absent in BM and DF, and that are expressed independent of passage number. This set of placental stem cell- or umbilical cord stem cell-specific genes encodes a number of cytoskeleton and cell-to-cell adhesion proteins associated with epithelial cells and an immunoglobulin-like surface protein, CD200, implicated in maternal-fetal immune tolerance. Placental stem cells and umbilical cord stem cells will be referred to collectively hereinafter in this Example as AC/UC stem cells.

6.10.1 Methods and Materials
6.10.1.1 Cells and Cell Culture

BM (Cat #PT-2501) and DF (Cat #CC-2511) were purchased from Cambrex. AC and UC originated from passage 0 tissue culture flasks. AC and UC in the flasks were obtained by digestion from a donor placenta designated 2063919. T-75 culture flasks were seeded at 6000 cells/cm$^2$ and cells were passaged when they became confluent. Population doublings were estimated from trypan blue cell counts. Cultures were assayed for gene expression after 3, 11-14, and 24-38 population doublings.

6.10.1.2 RNA, Microarrays, and Analysis

Cells were lysed directly in their tissue culture flasks, with the exception of one culture that was trypsinized prior to lysis. Total RNA was isolated with the RNeasy kit from QIAGEN. RNA integrity and concentrations were determined with an Agilent 2100 Bioanalyzer. Ten micrograms of total RNA from each culture were hybridized on an Affymetrix GENE-CHIP® platform. Total RNA was converted to labeled cRNAs and hybridized to oligonucleotide Human Genome U133A 2.0 arrays according to the manufacture's methods. Image files were processed with the Affymetrix MAS 5.0 software, and normalized and analyzed with Agilent Gene-Spring 7.3 software.

6.10.2 Results

6.10.2.1 Selection of BM-MSC, AC/UC Stem Cell, and DF Culture Time-Points for Microarray Analyses To establish a gene expression pattern unique to AC/UC stem cells, two stem cell lines, AC(6) and UC(6), were cultured in parallel with BM-MSC and DF. To maximize identifying a gene expression profile attributable to cellular origin and minimize exogenous influences all cells were grown in the same medium, seeded, and sub-cultured using the same criteria. Cells were harvested after 3 population doublings, 11-14 doublings, or 35 doublings or senescence, whichever came first. Genes whose expression in AC/UC stem cells are unchanged by time-in-culture and are up-regulated relative to BM and DF are candidates for AC/UC stem cell-specific genes.

FIG. 10 shows growth profiles for the four cell lines in the study; circles indicate which cultures were harvested for RNA isolation. In total twelve samples were collected. BM, AC(6), and UC(6) were harvested after three population doublings; these samples were regarded as being in culture for a "short" period of time. A short-term DF sample was not collected. Intermediate length cultures, 11 to 14 doublings, were collected for all cell types. Long-term cultures were collected from all cell lines at about 35 population doublings or just prior to senescence, whichever came first. Senescence occurred before 15 doublings for BM and at 25 doublings for DF. The purchased BM and DF cells were expanded many times prior to gene analysis, and cannot be considered early-stage. However, operationally, BM grown for three doublings (BM-03) are deemed a short-term culture. Likewise, BM-11 is operationally referred to as an intermediate length culture, but because senescence occurred at 14 doublings, BM-11 is most likely a long-term culture biologically.

6.10.2.2 Hierarchical Clustering Shows Relatedness between BM, AC/UC Stem Cells, and DF Microarray analysis identifies patterns of gene expression, and hierarchical clustering (HC) attempts to find similarities in the context of two dimensions—genes in the first dimension and different conditions (different RNA samples) in the second. The GeneChips used in this experiment contained over 22,000 probe sets (referred to as the "all genes list"), but many of these sets interrogate genes that are not expressed in any condition. To reduce the all genes list, genes not expressed or expressed at low levels (raw values below 250) in all samples were eliminated to yield a list of 8,215 genes.

6.10.2.3 Gene Expression Analysis Using the Line Graph View

Gene expression patterns of the 8215 genes were displayed using the line graph view in GeneSpring (FIG. 11). The x-axis shows the twelve experimental conditions and the y-axis shows the normalized probe set expression values on a log scale. The y-axis covers a 10,000-fold range, and genes that are not expressed or expressed at very low levels are set to a value of 0.01. By default the normalized value is set to 1. Each line represents a single gene (actually a probe set, some genes have multiple probe sets) and runs across all twelve conditions as a single color. Colors depict relative expression levels, as described for the heatmaps, but the coloring pattern is determined by selecting one condition. AC-03 is the selected condition in FIG. 11. Genes up-regulated relative to the normalized value are displayed by the software as red, and those that are down-regulated, are displayed as blue. The obvious upward and downward pointing spikes in AC-03 through UC-11 indicate that many genes are differentially expressed across these conditions. The striking similarity in the color patterns between AC-03 and UC-03 show that many of the same genes are up or down-regulated in these two samples. Horizontal line segments indicate that a gene's expression level is unchanged across a number of conditions. This is most notable by comparing UC-36, UC-38, and UC-38-T. There are no obvious spikes, but there is a subtle trend in that a number of red lines between UC-36 and UC-38-T are below the normalized value of 1. This indicates that these genes, which are up-regulated in AC-03 and UC-03, are down-regulated in the later cultures. The fact that the expression patterns between UC-38 and UC-38-T are so similar indicates that trypsinizing cells just prior to RNA isolation has little effect on gene expression.

In addition to the computationally intensive HC method, by visual inspection the two BM samples are more similar to each other than to the other conditions. The same is true for the two DF cultures. And despite the large number of differentially expressed genes present in the BM and DF samples, the general appearance suggests that two BMs and the two DFs are more similar to each other than to AC/UC stem cells. This is confirmed by the HC results described above.

When the above process is applied using AC-11 as the selected condition, it is clear that AC-11 and UC-11 share many of the same differentially expressed genes, but the total number of genes in common between these two conditions appears less than the number of differentially expressed genes shared by AC-03 and UC-03. FIG. 12 shows genes differentially over-expressed, by six-fold or more relative to the baseline, in AC-03. The majority of genes up-regulated in AC-03 are also up-regulated in UC-03, and more divergent in BM and DF.

6.10.2.4 Filtering Methods Used to Identify AC/UC Stem Cell-Specific Genes

Genes that remain constant across all AC/UC samples, and are down-regulated in BM and DF, are considered AC/UC stem cell-specific. Two filtering methods were combined to create a list of 58 AC/UC stem cell-specific genes (Table 4).

TABLE 4

58 Placental stem cell or Umbilical cord stem cell-specific genes

| Symbol | Gene | Biological Process, Description, and Additional Annotation |
|---|---|---|
| ACTG2 | actin, gamma 2, smooth muscle, enteric | muscle development, cytoskeleton, expressed in umbilical cord artery and prostate epithelia |
| ADARB1 | adenosine deaminase, RNA-specific, B1 (RED1 homolog rat) | RNA processing, central nervous system development |

TABLE 4-continued

58 Placental stem cell or Umbilical cord stem cell-specific genes

| Symbol | Gene | Biological Process, Description, and Additional Annotation |
|---|---|---|
| AMIGO2 | amphoterin induced gene 2 | homophilic and heterophilic cell adhesion, adhesion molecule with Ig like domain 2 |
| ARTS-1 | type 1 tumor necrosis factor receptor shedding aminopeptidase regulator | proteolysis, antigen processing, angiogenesis, expressed in placenta |
| B4GALT6 | UDP-Gal:betaGlcNAc beta 1,4-galactosyltransferase, polypeptide 6 | carbohydrate metabolism, integral to membrane, may function in intercellular recognition and/or adhesion |
| BCHE | butyrylcholinesterase | cholinesterase activity, serine esterase activity, hydrolase activity |
| C11orf9 | chromosome 11 open reading frame 9 | hypothetical protein, p53-like transcription factor, expressed in retinal pigment epithelium |
| CD200 | CD200 antigen | immunoglobulin-like, surface protein, inhibits macrophage |
| COL4A1 | collagen, type IV, alpha I | ECM, basement membrane, afibrillar collagen, contains arresten domain |
| COL4A2 | collagen, type IV, alpha 2 | ECM, biogenesis, basement membrane, coexpressed with COL 4A1, down-reg. in dysplastic epithelia |
| CPA4 | carboxypeptidase A4 | proteolytic, histone acetylation, maternal imprinted, high expression in prostate cancer cell lines |
| DMD | dystrophin (muscular dystrophy, Duchenne and Becker types) | muscle contraction, cell shape and cell size control, muscle development |
| DSC3 | desmocollin 3 | homophilic cell-cell adhesion, localized to desmosomes |
| DSG2 | desmoglein 2 | homophilic cell-cell adhesion, localized to desmosomes |
| ELOVL2 | elongation of very long chain fatty acids (FEN1/Elo2, SUR4/Elo3, yeast)-like 2 | fatty acid biosynthesis, lipid biosynthesis |
| F2RL1 | coagulation factor II (thrombin) receptor-like 1 | G-protein coupled receptor protein signaling pathway, highly expressed in colon epithelia and neuronal elements |
| FLJ10781 | hypothetical protein FLJ10781 | — |
| GATA6 | GATA binding protein 6 | transcription factor, muscle development |
| GPR 126 | G protein-coupled receptor 126 | signal transduction, neuropeptide signaling pathway |
| GPRC5B | G protein-coupled receptor, family C, group 5, member B | G-protein coupled receptor protein signaling pathway, |
| ICAM1 | intercellular adhesion molecule 1 (CD54), human rhinovirus receptor | cell-cell adhesion, cell adhesion, transmembrane receptor activity, expressed in conjunctival epithelium |
| IER3 | immediate early response 3 | anti-apoptosis, embryogenesis and morphogenesis, cell growth and/or maintenance |
| IGFBP7 | insulin-like growth factor binding protein 7 | negative regulation of cell proliferation, overexpressed in senescent epithelial cells |
| IL1A | interleukin 1, alpha | immune response, signal transduction, cytokine activity, cell proliferation, differentiation, apoptosis |
| IL1B | interleukin 1, beta | immune response, signal transduction, cytokine activity, cell proliferation, differentiation, apoptosis |
| 1L6 | interleukin 6 (interferon, beta 2) | cell surface receptor linked signal transduction, immune response |
| KRT18 | keratin 18 | morphogenesis, intermediate filament, expressed in placenta, fetal, and epithelial tissues |
| KRT8 | keratin 8 | cytoskeleton organization and biogenesis, phosphorylation, intermediate filament, coexpressed with KRT1B |
| LIPG | lipase, endothelial | lipid metabolism, lipoprotein lipase activity, lipid transporter, phospholipase activity, involved in vascular biology |
| LRAP | leukocyte-derived arginine aminopeptidase | antigen processing, endogenous antigen via MHC class I; N-terminal aminopeptidase activity |
| MATN2 | matrilin 2 | widely expressed in cell lines of fibroblastic or epithelial origin, nonarticular cartilage ECM |

TABLE 4-continued

58 Placental stem cell or Umbilical cord stem cell-specific genes

| Symbol | Gene | Biological Process, Description, and Additional Annotation |
|---|---|---|
| MEST | mesoderm specific transcript homolog (mouse) | paternally imprinted gene, development of mesodermal tissues, expressed in fetal tissues and fibroblasts |
| NFE2L3 | nuclear factor (erythroid-derived 2)-like 3 | transcription co-factor, highly expressed in primary placental cytotrophoblasts but not in placental fibroblasts |
| NUAK1 | NUAK family, SNF1-like kinase, I | protein amino acid phosphorylation, protein serine-threonine kinase activity |
| PCDH7 | BH-protocadherin (brain-heart) | cell-cell adhesion and recognition, containing 7 cadherin repeats |
| PDLIM3 | PDZ and LIM domain 3 | alpha-actinin-2-associated LIM protein, cytoskeleton protein binding, expressed in skeletal muscle |
| PKP2 | plakophilin 2 | cell-cell adhesion, localized to desmosomes, found in epithelia, binds cadherins and intermediate filament |
| RTN1 | reticulon 1 | signal transduction; neuron differentiation, neuroendocrine secretion, membrane trafficking in neuroendocrine cells |
| SERPINB9 | serpin peptidase inhibitor, ciade B (ovalbumin), member 9 | seine protease inhibitor, coagulation, fibrinolysis, complement fixation, matrix remodeling, expressed in placenta |
| ST3GAL6 | sialyltransferase 10 | amino sugar metabolism, protein amino acid glycosylation, glycolipid metabolism, protein-lipoylation |
| ST6GALNAC5 | sialyltransferase 7E | protein amino acid glycosylation, ganglioside biosynthesis |
| SLC12A8 | solute carrier family 12 (sodium/potassium/chloride transporters), member 8 | amino acid-polyamine transporter activity, cation-chloride cotransporter 9, possible role in epithelial immunity (psoriasis) |
| TCF21 | transcription factor 21 | regulation of transcription, mesoderm development, found in epithelial cells of the kidney |
| TGFB2 | transforming growth factor, beta 2 | regulation of cell cycle, signal transduction, cell-cell signaling, cell proliferation, cell growth |
| VTN | vitronectin (serum spreading factor, somatomedin B, complement S-protein) | immune response, cell adhesion, secreted protein, binds ECM |
| ZC3H12A | zinc finger CCCM-type containing 12A | MCP-I treatment-induced protein, nucleic acid binding, hypothetical zinc finger protein |

First, 58 genes were identified by selecting those genes over-expressed ≧three-fold in at least seven of eight AC/UC stem cell conditions relative to all BM and DF samples (FIG. 13). Filtering on eight of the eight AC/UC stem cell conditions yielded a similar list. The second filtering method used "absent" and "present" calls provided by the Affymetrix MAS 5.0 software. A list was created by identifying genes absent in all BM and DF conditions and present in AC-03, AC-11, UC-03, and UC-11. Gene calls in the later AC/UC stem cell conditions were not stipulated.

The two lists overlapped significantly and were combined. The combined list was trimmed further by eliminating (1) several genes expressed at very low levels in most or all AC/UC stem cell conditions, and (2) genes carried on the Y chromosome. AC and UC cells used in this study were confirmed to be male by FISH analysis, and the BM and DF were derived from a female donor. The resulting list of 46 AC/UC stem cell-specific genes is shown in Table 5.

TABLE 5

AC/UC-Specific Genes Listed by Ontology

| Cell Adhesion | Cytoskeletal | Development | ECM | Implicated in Epithelia |
|---|---|---|---|---|
| AMIGO2 | ACTG2 | ADARB1 | COL4A1 | ACTG2 |
| B4GALT6 | DMD | IER3 | COL4A2 | C11orf9 |
| DSC3 | KRT18 | IGFBP7 | MATN2 | COL4A1 |
| DSG2 | KRT8 | IL1A | VTN | COL4A2 |
| ICAM1 | PDLIM3 | IL1B | | DSC3 |
| PCDH7 | | MEST | | DSG2 |
| PKP2 | | TGFB2 | | F2RL1 |
| VTN | | | | ICAM1 |
| | | | | IGFBP7 |
| | | | | IL6 |
| | | | | KRT18 |
| | | | | KRT8 |
| | | | | MATN2 |
| | | | | PKP2 |
| | | | | SLC12A8 |

TABLE 5-continued

AC/UC-Specific Genes Listed by Ontology

| | | | | TCF21 |
|---|---|---|---|---|
| Glycosylation | Response Immune | Proteolysis | Signaling | Transcription |
| B4GALT6 | ARTS-1 | ARTS-1 | F2RL1 | C11orf9? |
| ST3GAL6 | CD200 | CPA4 | GPR126 | GATA6 |
| ST6GALNAC5 | IL1A | LRAP | GPRC5B | NFE2L3 |
| | IL1B | | IL1A | TCF21 |
| | IL6 | | IL1B | |
| | LRAP | | IL6 | |
| | SLC12A8 | | RTN1 | |
| | VTN | | TGFB2 | |

This list of 46 genes encodes a collection of proteins presenting a number of ontology groups. The most highly represented group, cell adhesion, contains eight genes. No genes encode proteins involved in DNA replication or cell division. Sixteen genes with specific references to epithelia are also listed.

6.10.3 Discussion

An expression pattern specific to placental stem cells, and distinguishable from bone marrow-derived mesenchymal cells, was identified. Operationally, this pattern includes 46 genes that are over expressed in all placental stem cell samples relative to all BM and DF samples.

The experimental design compared cells cultured for short, medium, and long periods of time in culture. For AC and UC cells, each culture period has a characteristic set of differentially expressed genes. During the short-term or early phase (AC-03 and UC-03) two hundred up-regulated genes regress to the mean after eight population doublings. Without being bound by theory, it is likely that this early stage gene expression pattern resembles the expression profile of AC and UC while in the natural placental environment. In the placenta these cells are not actively dividing, they are metabolizing nutrients, signaling between themselves, and securing their location by remodeling the extracellular surroundings.

Gene expression by the intermediate length cultures is defined by rapid cell division and genes differentially expressed at this time are quite different from those differentially expressed during the early phase. Many of the genes up-regulated in AC-11 and UC-11, along with BM-03 and DF-14, are involved in chromosome replication and cell division. Based on gene expression, BM-03 appears biologically to be a mid-term culture. In this middle stage cell type-specific gene expression is overshadowed by cellular proliferation. In addition, almost every gene over expressed in the short-term AC or UC cultures is down-regulated in the middle and later stage conditions. 143 genes were up-regulated ≧five-fold during this highly proliferative phase, constituting approximately 1.7% of the expressed genes.

The long-term cultures represent the final or senescent phase. In this phase, cells have exhausted their ability to divide, and, especially for AC and UC, the absolute number of differentially expressed genes is noticeably reduced. This may be the result of cells being fully adapted to their culture environment and a consequently reduced burden to biosynthesize. Surprisingly, late BM and DF cultures do not display this same behavior; a large number of genes are differentially expressed in BM-11 and DF-24 relative to AC and UC and the normalized value of 1. AC and UC are distinguishable from BM and DF most notably in the long-term cultures.

The placental stem cell-specific gene list described here is diverse. COL4A1 and COL4A2 are coordinately regulated, and KRT18 and KRT8 also appear to be co-expressed. Eight of the genes encode proteins involved in cell to cell contact, three of which (DSC3, DSG2, and PKP2) are localized to desmosomes, intercellular contact points anchored to intermediate filament cytoskeleton proteins such as keratin 18 and keratin 8. Tight cell-to-cell contact is characteristic of epithelial and endothelial cells and not typically associated with fibroblasts. Table 3 lists 16 genes, of the 46 total, characteristic to epithelial cells. Placental stem cells are generally described as fibroblast-like small spindle-shaped cells. This morphology is typically distinct from BM and DF, especially at lower cell densities. Also of note is the expression pattern of CD200, which is present in AC/UC stem cell and absent in all BM and DF samples. Moreover, CD200 has been shown to be associated with immune tolerance in the placenta during fetal development (see, e.g., Clark et al., *Am. J. Reprod. Immunol.* 50(3):187-195 (2003)).

This subset of genes of 46 genes constitutes a set of molecular biomarkers that distinguishes AC/UC stem cells from bone marrow-derived mesenchymal stem cells or fibroblasts.

What is claimed is:

1. Isolated human placental stem cells that are $CD34^-$, $CD10^+$ and $SH2^+$ as detected by flow cytometry, wherein said cells can be expanded.

2. The isolated human cells of claim 1, wherein the cells are $HLA-DR^-$.

3. The isolated human cells of claim 1, wherein said cells have the potential to differentiate into cells having one or more characteristics of osteogenic cells or chondrogenic cells.

4. The isolated human cells of claim 1, wherein said cells have been expanded.

5. The isolated human cells of claim 1 that are $CD90^+$ or $CD45^-$, as detected by flow cytometry.

6. The isolated human cells of claim 1 that are $CD90^+$ and $CD45^-$, as detected by flow cytometry.

7. The isolated human cells of claim 5 that are one or more of $CD29^+$, $CD38^-$, $CD44^+$, $CD54^+$, $SH3^+$ or $SH4^+$, as detected by flow cytometry.

8. The isolated human cells of claim 6 that are one or more of $CD29^+$, $CD38^-$, $CD44^+$, $CD54^+$, $SH3^+$ or $SH4^+$, as detected by flow cytometry.

9. The isolated human cells of claim 5 that are $CD44^+$, as detected by flow cytometry.

10. The isolated human cells of claim 6 that are $CD44^+$, as detected by flow cytometry.

11. The isolated human cells of claim 3, wherein said characteristics of osteogenic cells are at least one of cuboidal appearance, exhibition of mineralization, or expression of mRNA for alkaline phosphatase or osteopontin as assessed by RT-PCR.

12. The isolated human cells of claim 3, wherein said characteristics of chondrogenic cells are at least one of production of glycosaminoglycans, production of type II collagen, production of cartilage matrix acid mucopolysaccharides, or production of mRNA for type II collagen or type IX collagen as determined by RT-PCR.

13. The isolated human cell of claim 1, wherein said cells have the potential to differentiate into cells having characteristics of neurons or adipocytes.

14. The isolated human cells of claim 13, wherein said characteristics of neurons are at least one of expression of mRNA for nerve growth factor receptor or neurofilament heavy chain as determined by RT-PCR.

15. The isolated human cell of claim 13, wherein said characteristics of adipocytes are at least one of production of oil droplet vacuoles that stain with Oil Red, or expression of mRNA for lipase, fatty acid binding protein, PPAR-γ2, lipoprotein lipase or osteopontin as determined by RT-PCR.

16. The isolated human cells of claim 1 that are tissue culture plastic adherent.

17. An isolated population of cells enriched for the cells of claim 1.

18. An isolated population of cells enriched for the cells of claim 2.

19. An isolated population of cells enriched for the cells of claim 5.

20. An isolated population of cells enriched for the cells of claim 6.

21. An isolated population of cells enriched for the cells of claim 7.

22. An isolated population of cells enriched for the cells of claim 8.

23. An isolated population of cells enriched for the cells of claim 9.

24. An isolated population of cells enriched for the cells of claim 10.

* * * * *